(12) United States Patent
Johnson et al.

(10) Patent No.: US 7,524,655 B2
(45) Date of Patent: Apr. 28, 2009

(54) SYNTHESIS OF OLIGOSACCHARIDES, GLYCOLIPIDS, AND GLYCOPROTEINS USING BACTERIAL GLYCOSYLTRANSFERASES

(75) Inventors: Karl F. Johnson, Hatboro, PA (US); Daniel James Bezila, Philadelphia, PA (US); Diane E. Taylor, Edmonton (CA); Joanne Simala-Grant, Edmonton (CA); David Rasko, Arlington, VA (US)

(73) Assignees: Neose Technologies, Inc., Horsham, PA (US); Governors of the University of Alberta, Edmonton, Alberta (CA)

( * ) Notice: Subject to any disclaimer, the term of this patent is extended or adjusted under 35 U.S.C. 154(b) by 182 days.

(21) Appl. No.: 10/521,138

(22) Filed: Dec. 6, 2005

(65) Prior Publication Data

US 2007/0148728 A1    Jun. 28, 2007

Related U.S. Application Data

(63) Continuation of application No. PCT/US03/23155, filed on Jul. 23, 2003, and a continuation of application No. PCT/US03/23057, filed on Jul. 23, 2003.

(60) Provisional application No. 60/424,894, filed on Nov. 8, 2002, provisional application No. 60/398,156, filed on Jul. 23, 2002.

(51) Int. Cl.
  *C12P 19/18* (2006.01)
  *C12N 9/10* (2006.01)
  *C12N 9/52* (2006.01)
(52) U.S. Cl. .................. 435/97; 435/193; 435/220; 435/68.1; 435/69.1
(58) Field of Classification Search .......... None
See application file for complete search history.

(56) References Cited

U.S. PATENT DOCUMENTS

| 6,399,337 | B1 | 6/2002 | Taylor et al. |
| 6,534,298 | B2 | 3/2003 | Taylor et al. |
| 2002/0164749 | A1 | 11/2002 | Taylor et al. |
| 2003/0166211 | A1 | 9/2003 | Taylor et al. |
| 2003/0166212 | A1 | 9/2003 | Taylor et al. |

OTHER PUBLICATIONS

Dumon, Claire, et al., "In Vivo Fucosylation of Lacto-N-Neotetraose and Lacto-N-Neohexaose by Heterologous Expression of *Helicobacter pylori* α -1,3 Fucosyltransferase in Engineered *Escherichia Coli*;" 2001, *Glycoconjugate Journal*; vol. 18; pp. 465-474.
Johnson, Karl F.; "Synthesis of Oligosaccharides by Bacterial Enzymes;" 1999; *Glycoconjugate Journal*; vol. 16; pp. 141-146.
Johnson, Karl F., et al.; "Synthesis of Oligosaccharides and Glycolipids Using Bacterial Glycosyltransferases;" Oct. 2002; *Glycobiology*; vol. 12; No. 10; p. 706 Abstract.
Priem, Bernard, et al., "A New Fermentation Process Allows Large-Scale Production of Human Milk Oligosaccharides by Metabolically Engineered Bacteria;" 2002; *Glycobiology*; vol. 12, No. 4; pp. 235-240.
Rasko, David A., et al., "Cloning and Characterization of the α(1,3/4) Fucosyltransferase of *Helicobacter pylon*;" Feb. 18, 2000; *The Journal of Biological Chemistry*; vol. 275; No. 7; pp. 4988-4994.

*Primary Examiner*—Nashaat T Nashed
*Assistant Examiner*—Mohammad Younus Meah
(74) *Attorney, Agent, or Firm*—Townsend and Townsend and Crew LLP

(57) ABSTRACT

This invention provides nucleic acid and amino acid sequences of fucosyltransferases from *Helicobactor pylori*. The invention also provides methods to use the fucosyltransferases to synthesize oligosaccharides, glycoproteins, and glycolipids.

17 Claims, 22 Drawing Sheets

FIGURE 1

Fucosyltransferase nucleotide sequence from strain 1182 FutB (SEQ ID NO:1)

atgttccaaccccctattagacgcttatatagaaagcgcttccattgaaaaaattacctctaaatctccccccccctaaaaatcgctg
tggcgaattggtggggagatgaagaggttgaagaatttaaaaagaacattctttattttattctcagtcagcattacacaatcaccct
ccaccaaaaccccaacgaaccctccgatctcgtctttggcagtcctattggatcagccagaaaaatcttatcctatcaaaacgcaa
aaagagtgttttacaccggtgaaaacgaatcgcctaatttcaacctctttgattacgccataggctttgatgaattggattttagagat
cgttatttaagaatgcctttatattatgatagactacaccataaagccgagagcgtgaatgacaccacttcgccttacaaactcaaac
ctgacagcctttatgctttaaaaaaaccctcccatcattttaaagaaaaccaccccaatttatgcgcagtagtgaacaatgagagcg
atcctttgaaaagagggtttgcgagttttgtagcgagcaaccctaacgctcctaaaaggaatgctttctatgacgttttaaattctata
gagccagttattgggggagggagcgtgaaaaacactttaggctataacattaaaaacaagagcgagttttaagccaatacaaat
tcaatctgtgttttgaaaactcacaaggctatggctatgtaactgaaaaaatcattgacgcttactttagccataccattcctatttattg
ggggagtcctagcgtggcacaagattttaaccctaagagttttgtgaatgtttgtgattttaaagattttgatgaagcgattgatcatgt
gcgatacttgcacacgcacccaaacgcttatttagacatgctttatgaaaacccttttaaacacccttgatgggaaagcttactttac
caaaatttgagttttaaaaaaatcctagatttttttaaaaacgattttagaaaacgacacgatttatcacgataaccctttatttttttatcgt
gatttgaatgagccgttaatatctattgatgatgatttgagggttaattatgatgatttgagggttaattatgatgatttgagggttaatta
tgatgatttgagggttaattatgatgatttgagggttaattatgatgatttgagggttaattatgatgatttgagggttaattatgatgattt
gagggttaattatgatgatttgagggttaattatgatgatttgagggttaattatgatgatttgagggttaattatgagcggctcttaca
aaacgcctcgcctttattagaactctctcaaaacaccacttttaaaatctatcgcaaagcttatcaaaaatccttacctttgttgcgtgc
ggcgagaaagttgattaaaaaattgggtttgtaa Protein sequence from strain 1182 FutB (SEQ ID NO:2)

mfqplldayiesasiekitsksppplkiavanwwgdeeveefkknilyfilsqhytitlhqnpnepsdlvfgspigsarkilsy
qnakrvfytgenespnfnlfdyaigfdeldfrdrylrmplyydrlhhkaesvndttspyklkpdslyalkkpshhfkenhpnl
cavvnnesdplkrgfasfvasnpnapkrnafydvlnsiepvigggsvkntlgyniknkseflsqykfnlcfensqgygyvte
kiidayfshtipiywgspsvaqdfnpksfvnvcdfkdfdeaidhvrylhthpnayldmlyenplntldgkayfyqnlsfkki
ldffktilendtiyhdnpfifyrdlneplisidddlrvnyddlrvnyddlrvnyddlrvnyddlrvnyddlrvnyddlrvnydd
lrvnyddlrvnyddlrvnyddlrvnyerllqnasplelsqnttfkiyrkayqkslpllraarklikklgl*

FIGURE 2

Fucosyltransferase from strain 1111 FutA

Nucleotide coding sequence (SEQ ID NO:3)

atgttccaacccctattagatgcctttatagaaagcgctccattgaaaaaatggcctctaaatctcccccccctaaaaatcgctgtgg
cgaattggtggggagatgaagaaattaaaaaatttaaaaagagcgttctttatttttatcctaagccagcattacacaatcactttaca
ccgaaaccctgataaacctgcggacatcgtctttggtaaccccttggatcagccagaaaaatcttatcctatcaaaacgcaaaaa
gggtgttttacaccggtgaaaatgaagtccctaacttcaacctctttgattacgccataggctttgatgaattggactttagagatcgt
tatttgagaatgcctttgtattatgcctatttgcattataaagccgagcttgttaatgacaccacttcgccttataaactccaacctgaca
gcctttatgctttaaaaaaaccctcccatcattttaaagaaaaccaccccaatttgtgcgcagtagtgaataatgagagtgatcctttg
aaaagagggtttgcgagctttgtcgcaagcaaccctaacgctcctagaaggaacgcttttatgaggctttaaacgctattgagcc
agttgctgggggagggagcgtgaaaaacactttaggctataatgtcaaaaacaagagcgagttttttaagccaatacaaattcaat
ctgtgttttgaaaacactcaaggctatggctatgtaactgaaaagatcattgacgcttatttcagccataccattcctatttattggggg
agtcccagcgtggcgaaagattttaaccctaagagtttttgtgaatgtccatgatttcaacaactttgatgaagcgattgactatatca
gatacttgcacacgcacccaaacgcttatttagacatgcactatgaaaacccttttaaacacattgatgggaaagcttacttttacca
aaatttgagttttaaaaaaaatcctagatttttttaaaacgattttagaaaacgacacgatctatcacgataacccctttcattttctatcgtg
atttgaatgagccttcagtatctattgatggtttgagggttaattatgatgatttgagggttaattatgatgatttgagggttaattatgat
gatttgagggttaattatgagcgccttttacaaaacgcctcgcctttattagaactctctcaaaacaccacttttaaaatctatcgcaaa
gcttatcaaaaatccttgcctttgttgcgtgccataaggagatgggttaaaaagtaa

Protein sequence (SEQ ID NO:4)

mfqplldafiesaplkkwplnlpplkiavanwwgdeeikkfkksvlyfilsqhytitlhrnpdkpadivfgnplgsarkilsy
qnakrvfytgenevpnfnlfdyaigfdeldfrdrylrmplyyaylhykaelvndttspyklqpdslyalkkpshhfkenhpn
lcavvnnesdplkrgfasfvasnpnaprrnafyealnaiepvagggsvkntlgynvknkseflsqykfnlcfentqgygyvt
ekiidayfshtipiywgspsvakdfnpksfvnvhdfnnfdeaidyirylhthpnayldmhyenplntidgkayfyqnlsfk
kildffktilendtiyhdnpfifyrdlnepsvsidglrvnyddlrvnyddlrvnyddlrvnyerllqnaspllelsqnttfkiyrka
yqkslpllrairrwvkk*

FIGURE 3

Strain 1218 FutB nucleotide sequence (SEQ ID NO:5)

atgttccaaccccctattagacgcttatatagaaagcgcttccattgaaaaaattacctctaaatctccccccccccctaaaaatcgctg
tggcgaattggtggggagatgaagaggttgaagaatttaaaaagaacattctttattttattctcagtcagcattacacaatcaccct
ccaccaaaaccccaacgaaccctccgatctcgtctttggcagtcctattggatcagccagaaaaatcttatcctatcaaaacgcaa
aaagagtgttttacaccggtgaaaacgaatcgcctaatttcaacctctttgattacgccataggctttgatgaattggatttagagat
cgttatttaagaatgcctttatattatgatagactacaccataaagccgagagcgtgaatgacaccacttcgccttacaaactcaaac
ctgacagcctttatgctttaaaaaaaccctcccatcattttaaagaaaaccaccccaatttatgcgcagtagtgaacaatgagagcg
atcctttgaaaagagggtttgcgagttttgtagcgagcaaccctaacgctcctaaaaggaatgctttctatgacgctttaaattctata
gagccagttattgggggagggagcgtgaaaaacactttaggctataacattaaaaacaagagcgagtttttaagccaatacaaat
tcaatctgtgttttgaaaactcacaaggctatggctatgtaactgaaaaaatcattgacgcttacttagccataccattcctatttattg
ggggagtcctagcgtggcacaagattttaaccctaagagttttgtgaatgtttgtgattttaaagattttgatgaagcgattgatcatgt
gcgatacttgcacacgcacccaaacgcttatttagacatgctttatgaaaaccctttaaacacccttgatgggaaagcttacttttac
caaaatttgagttttaaaaaaaatcctagatttttttaaaacgatcttagaaaacgacacgatttatcacgataacccttttatttttatcgt
gatttgaatgagccgttaatatctattgatgatttgagggttaattatgatgatttgagggttaattatgatgatttgagggttaattatga
tgatttgagggttaattatgatgatttgagggttaattatgatgatttgagggttaattatgatgatttgagggttaattatgatgatttga
gggttaattatgatgatttgagggttaattgtgatgatttgagggttaattatgatgatttgagggttaattatgagcggctcttacaaa
acgcctcgcctttattagaactctctcaaaacaccacttttaaaatctatcgcaaagcttatcaaaaatccttacctttgttgcgtgcgg
cgagaaagttgattaaaaaattgggtttgtaa

Predicted protein strain 1218 FutB (SEQ ID NO:6)

mfqplldayiesasiekitskspppplkiavanwwgdeeveefkknilyfilsqhytitlhqnpnepsdlvfgspigsarkilsy
qnakrvfytgenespnfnlfdyaigfdeldfrdrylrmplyydrlhhkaesvndttspyklkpdslyalkkpshhfkenhpnl
cavvnnesdplkrgfasfvasnpnapkrnafydalnsiepvigggsvkntlgyniknkseflsqykfnlcfensqgygyvte
kiidayfshtipiywgspsvaqdfnpksfvnvcdfkdfdeaidhvrylhthpnayldmlyenplntldgkayfyqnlsfkki
ldffktilendtiyhdnpfifyrdlneplisiddlrvnyddlrvnyddlrvnyddlrvnyddlrvnyddlrvnyddlrvnyddlr
vnyddlrvncddlrvnyddlrvnyerllqnaspllelsqnttfkiyrkayqkslpllraarklikklgl*

FIGURE 4

Fucosyltransferase strain 19C2 FutB nucleotide sequence (SEQ ID NO:7)

atgttccaaccccctattagacgcttatatagacagcacccgtttagatgaaaccgattataagcccccattaaatatagccctagcg
aattggtggcctttggataaaagagaaagcaaagggtttagaaaaaaatttatcttacatttcattttaagtcagcattacacaatcgc
tctccaccgaaaccctgataaacctgcggacatcgttttggtaaccccttggatcagccagaaaaatcctatcctatcaaaacg
ctaaaagggtgttttacaccggtgaaaacgaagtccctaatttcaacctctttgattacgccataggctttgatgaattggactttaga
gatcgttatttgagaatgcctttatattatgatagactacaccataaagccgagagcgtgaatgacaccaccgcaccttacaagatt
aaatctgacagcctttatgctttaaaaaagccctcccatcattttaaagaaaaccacccacatttatgcgcgctaatcaataatgaga
tcgatcctttgaaaagagggtttgcgagctttgtcgcaagcaaccctaacgcccctataaggaacgctttctatgaggctttaaattc
tattgagccagttactgggggagggagcgtgagaaacactttaggctataacgtcaaaaacaaaaacgaatttttgagccaatac
aagttcaatctgtgctttgaaaacactcaaggctatggctatgttactgaaaaaatcattgacgcttacttcagccacaccattcctat
ttattggggggggagtccctagcgtggcgaaagattttaacccc Strain 19C2 FutB protein sequence (SEQ ID NO:8)

mfqplldayidstrldetdykpplnialanwwpldkreskgfrkkfilhfilsqhytialhrnpdkpadivfgnplgsarkilsy
qnakrvfytgenevpnfnlfdyaigfdeldfrdrylrmplyydrlhhkaesvndttapykiksdslyalkkpshhfkenhph
lcalinneidplkrgfasfvasnpnapirnafyealnsiepvtgggsvmtlgynvknkneflsqykfnlcfentqgygyvtek
iidayfshtipiywggvpsvakdfnp

FIGURE 5

Strain 915 FutA fucosyltransferase nucleotide coding sequence (SEQ ID NO:9)

atggcctctaaatctccccccctaaaaatcgctgtggcgaattggtggggagatgaagaaattaaaaaatttaaaaagagcgttct
ttattttatcctaagccagcattacacaatcactttacaccgaaaccctgataaacctgcggacatcgtctttggtaaccccttggat
cagccagaaaaatcttatcctatcaaaacgcaaaaagggtgttttacaccggtgaaaatgaagtccctaacttcaacctctttgatta
cgccataggcttt Protein sequence from Strain 915 FutA (SEQ ID NO:10)

maskspplkiavanwwgdeeikkfkksvlyfilsqhytitlhrnpdkpadivfgnplgsarkilsyqnakrvfytgenevpn
fnlfdyaigf

FIGURE 6

Strain 26695 FutA fucosyltransferase nucleotide coding sequence (SEQ ID NO:11)

atgttccaaccccctattagacgcctttatagaaagcgcttccattgaaaaaatggcctctaaatctccccccccccccctaaaaatc
gctgtggcgaattggtggggagatgaagaaattaaagaatttaaaaagagcgttctttattttatcctaagccaacgctacgcaatc
accctccaccaaaaccccaatgaattttcagatctagttttagcaatcctcttggagcggctagaaagatttatcttatcaaaacac
taaacgagtgttttacaccggtgaaaacgaatcacctaatttcaacctctttgattacgccataggctttgatgaattggatttaatga
tcgttatttgagaatgcctttgtattatgcccatttgcactataaagccgagcttgttaatgacaccactgcgccctacaaactcaaag
acaacagcctttatgctttaaaaaaaccctctcatcattttaaagaaaaccaccctaatttgtgcgcagtagtgaatgatgagagcg
atcttttaaaaagagggtttgccagttttgtagcgagcaacgctaacgctcctatgaggaacgcttttttatgacgctctaaattccata
gagccagttactgggggaggaagtgtgagaaacactttaggctataaggttggaaacaaaagcgagttttttaagccaatacaagt
tcaatctctgttttgaaaactcgcaaggttatggctatgtaaccgaaaaaatccttgatgcgtattttagccataccattcctatttattg
ggggagtcccagcgtggcgaaagattttaaccctaaaagttttgtgaatgtgcatgatttcaacaactttgatgaagcgattgattat
atcaaatacctgcacacgcacccaaacgcttatttagacatgctctatgaaaacccttttaaacacccttgatgggaaagcttactttt
accaagatttgagttttaaaaaaatcctagatttttttaaaacgattttagaaaacgatacgatttatcacaaattctcaacatctttcatg
tgggagtacgatctgcataagccgttagtatccattgatgatttgagggttaattatgatgatttgagggttaattatgaccggctttta
caaaacgcttcgcctttattagaactctctcaaaacaccacttttaaaatctatcgcaaagcttatcaaaaatccttgcctttgttgcgc
gcggtgagaaagttggttaaaaaattgggtttgtaa Protein coding sequence Strain 26695 FutA (SEQ ID NO:12)

mfqplldafiesasiekmaskspppplkiavanwwgdeeikefkksvlyfilsqryaitlhqnpnefsdlvfsnplgaarkil
syqntkrvfytgenespnfnlfdyaigfdeldfndrylrmplyyahlhykaelvndttapyklkdnslyalkkpshhfkenh
pnlcavvndesdlllkrgfasfvasnanapmrnafydalnsiepvtgggsvmtlgykvgnkseflsqykfnlcfensqgygy
vtekildayfshtipiywgspsvakdfnpksfvnvhdfnnfdeaidyikylhthpnayldmlyenplntldgkayfyqdlsf
kkildffktilendtiyhkfstsfmweydlhkplvsiddlrvnyddlrvnydrllqnaspllelsqnttfkiyrkayqkslpllrav
rklvkklgl*

FIGURE 7

19C2A fucosyltransferase nucleotide sequence (SEQ ID NO:13)

atgttccaacccttactagacgcctttatagaaagtgctccaatt

19C2A predicted protein sequence (SEQ ID NO:14)

mfqplldafiesapi

FIGURE 8

Protein sequence from strain 1182 FutB aligned with pfam00852, Glyco_transf_10, Glycosyltransferase family 10

```
Query:   23  PPPLKIAVANWWGDEEVEEFKKNILYFILSQHYTITLHQNPNEPSDLVFGS-PIGSARKI    81
Sbjct:   11  TVPLLLAIYTWWSLIEYKEWKKSPIYFIGSQAPQPPLR---ILLWTWPFNGNPLALSDCP   67

Query:   82  LSYQNAKRVFYTGEN---ESPNFNLF---DYAIGFDELDFRDRYLRMPLYYDRLHHKAES  135
Sbjct:   68  LSYQNTARCRLTANRSPLESADAVLFHHRDLSKGFPDLPPSPRPPGQPWVWASMESPSNS  127

Query:  136  -VNDTTSPYKLKPDSLYALKKPSHHFKENHPNLCAVVNNESDPLKRGPASFVASNPN-AP  193
Sbjct:  128  GLNDLRDGYFNWTLSYRADSDAFHPYGYLEPRLSQVVNAPLLSAKRKGAAWVVSNCNTRS  187

Query:  194  KRNAFYDVLNSIEPVIGGGSVKNTLGYNIKNKSEFLSQYKFNLCFENSQGYGYVTEKIID  253
Sbjct:  188  KRERFYKQLNKHLQVDVGGRVANPLPLKVGCLVETLSQYKFYLAFENSQHYDYVTEKLWK  247

Query:  254  -AYFSHTIPIYWGSPSVAQDFNP-KSFVNVCDFKDFDEAIDHVRYLHTHPNAYL       305
Sbjct:  248  NALQAGTIPVVLGPRAVYEDFVPPKSFIHVDDFKSPKELADYLLYLDTNPTAYS       301
```

FIGURE 9

Fucosyltransferase from strain 1111 FutA aligned with pfam00852, Glyco_transf_10, Glycosyltransferase family 10

```
Query:   27  IAVANWWGDEEIKKFKKSVLYFILSQHYTITLHRNPDKPADIVFG-NPLGSARKILSYQN   85
Sbjct:   16  LAIYTWWSLIEYKEWKKSPIYFIGSQAPQPPLR---ILLWTWPFNGNPLALSDCPLSYQN   72

Query:   86  AKRVFYTGEN---EVPNFNLF---DYAIGFDELDFRDRYLRMPLYYAYLHYKAEL-VNDT  138
Sbjct:   73  TARCRLTANRSPLESADAVLFHHRDLSKGFPDLPPSPRPPGQPWVWASMESPSNSGLNDL  132

Query:  139  TSPYKLQPDSLYALKKPSHHPKENHPNLCAVVNNESDPLKRGFASFVASNPN-APRRNAF  197
Sbjct:  133  RDGYFNWTLSYRADSDAFHPYGYLEPRLSQVVNAPLLSAKRKGAAWVVSNCNTRSKRERF  192

Query:  198  YEALNAIEPVAGGGSVKNTLGYNVKNKSEFLSQYKFNLCFENTQGYGYVTEKIID-AYFS  256
Sbjct:  193  YKQLNKHLQVDVGGRVANPLPLKVGCLVETLSQYKFYLAFENSQHYDYVTEKLWKNALQA  252

Query:  257  HTIPIYWGSPSVAKDFNP-KSFVNVHDFNNFDEAIDYIRYLHTHPNAYLDMHYENPLNTI  315
Sbjct:  253  GTIPVVLGPRAVYEDFVPPKSFIHVDDFKSPKELADYLLYLDTNPTAYS-----------  301

Query:  316  DGKAYFYQNLSFKKILDFFKTILENDTIYHDNPFIFYRDLNEPSVSIDGLRVNYDDLRVN  375
Sbjct:  302  -----------------------------EYFEWRYDLRVRLFSWDALR---------  321

Query:  376  YDDLRVNYDDLRVNYERLLQNASPLLELSQNTTFKIYRKAYQ  417
Sbjct:  322  -------YDEGFCRVCRLLQNAPD-----RYKTYPNIAKWFQ  351
```

FIGURE 10

Protein sequence from strain 1218 FutB aligned with pfam00852, Glyco_transf_10, Glycosyltransferase family 10

```
Query:   23  PPPLKIAVANWWGDEEVEEFKKNILYFILSQHYTITLHQNPNEPSDLVFGS-PIGSARKI  81
Sbjct:   11  TVPLLLAIYTWWSLIEYKEWKKSPIYFIGSQAPQPPLR---ILLWTWPFNGNPLALSDCP  67

Query:   82  LSYQNAKRVFYTGEN---ESPNFNLF---DYAIGFDELDFRDRYLRMPLYYDRLHHKAES  135
Sbjct:   68  LSYQNTARCRLTANRSPLESADAVLFHHRDLSKGFPDLPPSPRPPGQPWVWASMESPSNS  127

Query:  136  -VNDTTSPYKLKPDSLYALKKPSHHFKENHPNLCAVVNNESDPLKRGFASFVASNPN-AP  193
Sbjct:  128  GLNDLRDGYFNWTLSYRADSDAFHPYGYLEPRLSQVVNAPLLSAKRKGAAWVVSNCNTRS  187

Query:  194  KRNAFYDALNSIEPVIGGGSVKNTLGYNIKNKSEFLSQYKFNLCFENSQGYGYVTEKIID  253
Sbjct:  188  KRERFYKQLNKHLQVDVGGRVANPLPLKVGCLVETLSQYKFYLAFENSQHYDYVTEKLWK  247

Query:  254  -AYFSHTIPIYWGSPSVAQDFNP-KSFVNVCDFKDFDEAIDHVRYLHTHPNAYLDMLYEN  311
Sbjct:  248  NALQAGTIPVVLGPRAVYEDFVPPKSFIHVDDFKSPKELADYLLYLDTNPTAYS------  301

Query:  312  PLNTLDGKAYFYQNLSFKKILDFPKTILENDTIYHDNPFIPYRDLNEPLISIDDLRVNYD  371
Sbjct:  302  ---------------------------------EYFEWRYDLRVRLFSWDALR--YD  323

Query:  372  DLRVNYDDLRVNYDDLRVNYDDLRVNYD  399
Sbjct:  324  EGFCRVCRLLQNAPDRYKTYPNIAKWFQ  351
```

FIGURE 11

Protein sequence from strain 19C2 FutB aligned with pfam00852, Glyco_transf_10, Glycosyltransferase family 10

```
Query:   22  PPLNIALANWWPLDKRESKGFRKKFILHFILSQHYTIALHRNPDKPADIVFG-NPLGSAR   80
Sbjct:   12  VPLLLAIYTWWSL--IEYKEW-KKSPIYPIGSQAPQPPLR---ILLWTWPFNGNPLALSD. 65

Query:   81  KILSYQNAKRVFYTGEN---EVPNFNLF---DYAIGFDELDFRDRYLRMPLYYDRLHHKA  134
Sbjct:   66  CPLSYQNTARCRLTANRSPLESADAVLFHHRDLSKGFPDLPPSPRPPGQPWVWASMESPS  125

Query:  135  ES-VNDTTAPYKIKSDSLYALKKPSHHFKENHPHLCALINNEIDPLKRGFASFVASNPN-  192
Sbjct:  126  NSGLNDLRDGYFNWTLSYRADSDAFHPYGYLEPRLSQVVNAPLLSAKRKGAAWVVSNCNT  185

Query:  193  APIRNAFYEALNSIEPVTGGGSVRNTLGYNVKNKNEFLSQYKFNLCFENTQGYGYVTEKI  252
Sbjct:  186  RSKRERFYKQLNKHLQVDVGGRVANPLPLKVGCLVETLSQYKFYLAFENSQHYDYVTEKL  245

Query:  253  ID-AYFSHTIPIYWGGVPSVAKDFNP  277
Sbjct:  246  WKNALQAGTIPVVLGP-RAVYEDFVP  270
```

FIGURE 12

```
                    1                                                  50
1111FutA.pep   (1)  MFQPLLDAFIESAPIKKWPLN--LPPLKIAVANWWGDEEIKK---FKKSI
   19C2A.pep   (1)  MFQPLLDAFIESAPI-----------------------------------
915A.pepneose  (1)  ------------------MASK-SPPLKIAVANWWGDEEIKK---FKKSI
  26695A.pep   (1)  MFQPLLDAFIESASIEKMASKSPPPPLKIAVANWWGDEEIKE---FKKSI
   1182B.pep   (1)  MFQPLLDAYIESASIEKITSKS-PPPLKIAVANWWGDEEVBE---FKKNI
   1218B.pep   (1)  MFQPLLDAYIESASIEKITSKS-PPPLKIAVANWWGDEEVBE---FKKNI
 ORF19C2B.pep  (1)  MFQPLLDAVIDSTRLDETDYK---PPLNIALANWWPLDKRESKGFRKKFI
    Consensus  (1)  MFQPLLDAFIESA IEK  SK   PPLKIAVANWWGDEEI    FKK I 51                                                 100
1111FutA.pep  (46)  LYFILSQHYTITLHRNPDKPADIVFGNPLGSARKILSYQNAKRVFYTGEN
   19C2A.pep  (16)  --------------------------------------------------
915A.pepneose (29)  LYFILSQHYTITLHRNPDKPADIVFGNPLGSARKILSYQNAKRVFYTGEN
  26695A.pep  (48)  LYFILSQRYAITLHQNPNEFSDIVFSNPLGAARKILSYQNTKRVFYTGEN
   1182B.pep  (47)  LYFILSQHYTITLHQNPNEPSDIVFGSPIGSARKILSYQNAKRVFYTGEN
   1218B.pep  (47)  LYFILSQHYTITLHQNPNEPSDIVFGSPLGSARKILSYQNAKRVFYTGEN
 ORF19C2B.pep (48)  LHFILSQHYTIALHRNPDKPADIVFGNPLGSARKILSYQNAKRVFYTGEN
    Consensus (51)  LYFILSQHYTITLH NP  PADIVFGNPLGSARKILSYQNAKRVFYTGEN 101                                                 150
1111FutA.pep  (96)  EVPNFNLFDYAIGFDELDFRDRYLRMPLYYAYLHYKAELVNDTTSPYKLQ
   19C2A.pep  (16)  --------------------------------------------------
915A.pepneose (79)  EVPNFNLFDYAIGF------------------------------------
  26695A.pep  (98)  ESPNFNLFDYAIGFDELDFNDRYLRMPLYYAHLHYKAELVNDTTAPYKLK
   1182B.pep  (97)  ESPNFNLFDYAIGFDELDFRDRYLRMPLYYDRLHHKAESVNDTTSPYKLK
   1218B.pep  (97)  ESPNFNLFDYAIGFDELDFRDRYLRMPLYYDRLHHKAESVNDTTSPYKLK
 ORF19C2B.pep (98)  EVPNFNLFDYAIGFDELDFRDRYLRMPLYYDRLHHKAESVNDTTAPYKLK
    Consensus(101)  E PNFNLFDYAIGFDELDFRDRYLRMPLYY  LHHKAE VNDTTSPYKLK 151                                                 200
1111FutA.pep (146)  PDSLYALKKPSHHFKENHPNLCAVVNNESDPLKRGFASFVASNPNAPRRN
   19C2A.pep  (16)  --------------------------------------------------
915A.pepneose (93)  --------------------------------------------------
  26695A.pep (148)  DNSLYALKKPSHHFKENHPNLCAVVNDESDLLKRGFASFVASNANAPMRN
   1182B.pep (147)  PDSLYALKKPSHHFKENHPNLCAVVNNESDPLKRGFASFVASNPNABKRN
   1218B.pep (147)  PDSLYALKKPSHHFKENHPNLCAVVNNESDPLKRGFASFVASNPNABKRN
 ORF19C2B.pep(148)  SDSLYALKKPSHHFKENHPHLCALINNEIDPLKRGFASFVASNPNABIRN
    Consensus(151)  DSLYALKKPSHHFKENHPNLCAVVNNESDPLKRGFASFVASNPNAP RN 201                                                 250
1111FutA.pep (196)  AFYEALNAIEPVAGGGSVKNTLGYNVKNKSEFLSQYKFNLCRENTQGYGY
   19C2A.pep  (16)  --------------------------------------------------
915A.pepneose (93)  --------------------------------------------------
  26695A.pep (198)  AFYDALNSIEPVTGGGSVRNTLGYKVGNKSEFLSQYKFNLCFENSQGYGY
   1182B.pep (197)  AFYDVLNSIEPVIGGGSVKNTLGYNIKNKSEFLSQYKFNLCFENSQGYGY
   1218B.pep (197)  AFYDALNSIEPVIGGGSVKNTLGYNIKNKSEFLSQYKFNLCFENSQGYGY
 ORF19C2B.pep(198)  AFYEALNSIEPVTGGGSVRNTLGYNVKNKNEFLSQYKFNLCFENTQGYGY
    Consensus(201)  AFYDALNSIEPV GGGSVKNTLGYNVKNKSEFLSQYKFNLCFENSQGYGY
```

FIGURE 13

```
                        1                                                  50
1111FutA       (1)  ATGTTCCAACCCCTATTAGATGCCTTTATAGAAAGCGCT-CCATTGAAAA
915A.cod(MWG)  (1)  ATGTTCCAACCCCTATTAGATGCCTTTATAGAAAGCGCTTCCATTGAAAA
19C2FutA.cod   (1)  ATGTTCCAACCCTTACTAGACGCCTTTATAGAAAGTGCTCCAATT-----
26695A.cod     (1)  ATGTTCCAACCCCTATTAGACGCCTTTATAGAAAGCGCTTCCATTGAAAA
1182B          (1)  ATGTTCCAACCCCTATTAGACGCTTATATAGAAAGCGCTTCCATTGAAAA
1218B.nuc      (1)  ATGTTCCAACCCCTATTAGACGCTTATATAGAAAGCGCTTCCATTGAAAA
ORF19C2B       (1)  ATGTTCCAACCCCTATTAGACGCTTATATAGACAGCACCCGTTTAGATGA
Consensus      (1)  ATGTTCCAACCCCTATTAGACGCCTTTATAGAAAGCGCTTCCATTGAAAA 51                                                100
1111FutA       (50) AATGGCCTCTAAATCTCCCCCCCC-----TAAAAATCGCTGTGGCGAATT
915A.cod(MWG)  (51) AATGGCCTCTAAATCTCCCCCCC------TAAAAATCGCTGTGGCGAATT
19C2FutA.cod   (46) --------------------------------------------------
26695A.cod     (51) AATGGCCTCTAAATCTCCCCCCCCCCCCTAAAAATCGCTGTGGCGAATT
1182B          (51) AATTACCTCTAAATCTCCCCCCCCC---TAAAAATCGCTGTGGCGAATT
1218B.nuc      (51) AATTACCTCTAAATCTCCCCCCCCC---TAAAAATCGCTGTGGCGAATT
ORF19C2B       (51) AACCGATTATAA------GCCCCAT---TAAATATAGCCCTAGCGAATT
Consensus      (51) AAT GCCTCTAAATCTCCCCCCCC     TAAAAATCGCTGTGGCGAATT 101                                               150
1111FutA       (95) GGTGG-----GGAGATGA-AGAAATTAAAAAATTTAAAAAGAGCGTTCTT
915A.cod(MWG)  (95) GGTGG-----GGAGATGA-AGAAATTAAAAAATTTAAAAAGAGCGTTCTT
19C2FutA.cod   (46) --------------------------------------------------
26695A.cod    (101) GGTGG-----GGAGATGA-AGAAATTAAAGAATTTAAAAAGAGCGTTCTT
1182B         (98)  GGTGG-----GGAGATGA-AGAGGTTGAAGAATTTAAAAAGAACATTCTT
1218B.nuc     (98)  GGTGG-----GGAGATGA-AGAGGTTGAAGAATTTAAAAAGAACATTCTT
ORF19C2B      (92)  GGTGGCCTTTGGATAAAGAGAAAGCAAAGGGTTTAGAAAAAATTTATC
Consensus    (101)  GGTGG     GGAGATGA AGAAATTAAAGAATTTAAAAAGA C TTCTT 151                                               200
1111FutA      (139) T---ATTTTATCCTAAGCCAGCATTACACAATCAGTTTACACCGAAACCC
915A.cod(MWG) (139) T---ATTTTATCCTAAGCCAGCATTACACAATCAGTTTACACCGAAACCC
19C2FutA.cod   (46) --------------------------------------------------
26695A.cod    (145) T---ATTTTATCCTAAGCCAACGCTACGCAATCACCCTCCACCAAAACCG
1182B         (142) T---ATTTTATTCTCAGTCAGCATTACACAATCACCGTCCACCAAAACCC
1218B.nuc     (142) T---ATTTTATTGTCAGTCAGCATTACACAATCACCCTCCACCAAAACCC
ORF19C2B      (142) TTACATTTCATTTTAAGTCAGCATTACAGAATCGGTCTCCACCGAAACCC
Consensus     (151) T   ATTTTAT CTAAG CAGCATTACACAATCAC CTCCACC AAACCC 201                                               250
1111FutA      (186) TGATAAACCTGCGGACATCGTCTTTGGTAACCCCCTTGGATCAGCCAGAA
915A.cod(MWG) (186) TGATAAACCTGCGGACATCGTCTTTGGTAACCCCCTTGGATCAGCCAGAA
19C2FutA.cod   (46) --------------------------------------------------
26695A.cod    (192) CAATGAATTTTCAGATCTAGTTTTTAGCAATCCTCTTGGAGCGGCTAGAA
1182B         (189) CAACGAACCCTCCGATCTCGTCTTTGGCAGTCCTATTGGATCAGCCAGAA
1218B.nuc     (189) CAACGAACCCTCCGATCTCGTCTTTGGCAGTCCTATTGGATCAGCCAGAA
ORF19C2B      (192) TGATAAACCTGCGGACATCGTTTTTGGTAACCCCCTTGGATCAGCCAGAA
Consensus     (201)    AT AACCT C GA  TCGTCTTTGG AA CC CTTGGATCAGCCAGAA
```

FIG. 13 (CONT)

```
                         251                                                300
1111FutA       (236)  AAATCTTATCCTATCAAAACGCAAAAAGGGTGTTTTACACCGGTGAAAAT
915A.cod(MWG)  (236)  AAATCTTATCCTATCAAAACGCAAAAAGGGTGTTTTACACCGGTGAAAAT
19C2FutA.cod    (46)  --------------------------------------------------
26695A.cod     (242)  AGATTTATCTTATCAAAACACTAAACGAGTGTTTTACACCGGTGAAAAC
1182B          (239)  AAATCTTATCCTATCAAAACGCAAAAAGAGTGTTTTACACCGGTGAAAAC
1218B.nuc      (239)  AAATCTTATCCTATCAAAACGCAAAAAGAGTGTTTTACACCGGTGAAAAC
ORF19C2B       (242)  AAATCCTATCCTATCAAAACGGTAAAAGGGTGTTTTACACCGGTGAAAAC
Consensus      (251)  AAATCTTATCCTATCAAAACGCAAAAAG GTGTTTTACACCGGTGAAAAC 301                                                350
1111FutA       (286)  GAAGTCCCTAACTTCAACCTCTTTGATTACGCCATAGGCTTT-GATGAAT
915A.cod(MWG)  (286)  GAAGTCCCTAACTTCAACCTCTTTGATTACGCCATAGGCTTTTGATGA--
19C2FutA.cod    (46)  --------------------------------------------------
26695A.cod     (292)  GAATCACCTAATTTCAACCTCTTTGATTACGCCATAGGCTTT-GATGAAT
1182B          (289)  GAATCGCCTAATTTCAACCTCTTTGATTACGCCATAGGCTTT-GATGAAT
1218B.nuc      (289)  GAATCGCCTAATTTCAACCTCTTTGATTACGCCATAGGCTTT-GATGAAT
ORF19C2B       (292)  GAAGTCCCTAATTTCAACCTCTTTGATTACGCCATAGGCTTT-GATGAAT
Consensus      (301)  GAA   CCTAATTTCAACCTCTTTGATTACGCCATAGGCTTT GATGAAT 351                                                400
1111FutA       (335)  TGGACTTTAGAGATCGTTATTTGAGAATGCCTTTGTATTATGCCTATTTG
915A.cod(MWG)  (334)  --------------------------------------------------
19C2FutA.cod    (46)  --------------------------------------------------
26695A.cod     (341)  TGGATTTTAATGATCGTTATTTGAGAATGCCTTTGTATTATGCCCATTTG
1182B          (338)  TGGATTTTAGAGATCGTTATTTAAGAATGCCTTTATATTATGATAGACTA
1218B.nuc      (338)  TGGATTTTAGAGATCGTTATTTAAGAATGCCTTTATATTATGATAGACTA
ORF19C2B       (341)  TGGACTTTAGAGATCGTTATTTGAGAATGCCTTTATATTATGATAGACTA
Consensus      (351)  TGGA TTTAGAGATCGTTATTT AGAATGCCTTT TATTATG        T 401                                                450
1111FutA       (385)  CATTATAAAGCCGAGCTTGTTAATGACACCACTTCGCCTTATAAACTCCA
915A.cod(MWG)  (334)  --------------------------------------------------
19C2FutA.cod    (46)  --------------------------------------------------
26695A.cod     (391)  CACTATAAAGCCGAGCTTGTTAATGACACCACTGCGCCCTACAAACTCAA
1182B          (388)  CACCATAAAGCCGAGAGCGTGAATGACACCACTTCGCCTTACAAACTCAA
1218B.nuc      (388)  CACCATAAAGCCGAGAGCGTGAATGACACCACTTCGCGTTACAAACTCAA
ORF19C2B       (391)  CACCATAAAGCCGAGAGCGTGAATGACACCACCGCACGTTACAAGATTAA
Consensus      (401)  CAC ATAAAGCCGAG  GT AATGACACCACT CGCCTTACAAACTCAA 451                                                500
1111FutA       (435)  ACCTGACAGCCTTTATGCTTTAAAAAAACCCTCCATCATTTTAAAGAAA
915A.cod(MWG)  (334)  --------------------------------------------------
19C2FutA.cod    (46)  --------------------------------------------------
26695A.cod     (441)  AGACAACAGCCTTTATGCTTTAAAAAAACCCTCTCATCATTTTAAAGAAA
1182B          (438)  ACCTGACAGCCTTTATGCTTTAAAAAAACCCTCCATCATTTTAAAGAAA
1218B.nuc      (438)  ACCTGACAGCCTTTATGCTTTAAAAAAACCCTCCATCATTTTAAAGAAA
ORF19C2B       (441)  ATCTGACAGCCTTTATGCTTTAAAAAGCCGTCCATCATTTTAAAGAAA
Consensus      (451)  A CTGACAGCCTTTATGCTTTAAAAAAACCCTCCATCATTTTAAAGAAA
```

FIG. 13 (CONT)

```
                        501                                               550
1111FutA       (485)    ACCACCCCAATTTGTGCGCAGTAGTGAATAATGAGAGTGATCCTTTGAAA
915A.cod(MWG)  (334)    --------------------------------------------------
19C2FutA.cod   (46)     --------------------------------------------------
26695A.cod     (491)    ACCACCCTAATTTGTGCGCAGTAGTGAATGATGAGAGCGATCTTTTAAAA
1182B          (488)    ACCACCCCAATTTATGCGCAGTAGTGAACAATGAGAGCGATCCTTTGAAA
1218B.nuc      (488)    ACCACCCCAATTTATGCGCAGTAGTGAACAATGAGAGCGATCCTTTGAAA
ORF19C2B       (491)    ACCACCCACATTTATGCGCGCTAATCAATAATGAGATCGATCCTTTGAAA
Consensus      (501)    ACCACCC AATTT TGCGCAGTAGTGAA AATGAGAGCGATCCTTTGAAA 551                                               600
1111FutA       (535)    AGAGGGTTTGCGAGCTTTGTCGCAAGCAACCCTAACGCTCCTAGAAGGAA
915A.cod(MWG)  (334)    --------------------------------------------------
19C2FutA.cod   (46)     --------------------------------------------------
26695A.cod     (541)    AGAGGGTTTGCCAGTTTTGTAGCGAGCAACGCTAACGCTCCTATGAGGAA
1182B          (538)    AGAGGGTTTGCGAGTTTTGTAGCGAGCAACCCTAACGCTCCTAAAAGGAA
1218B.nuc      (538)    AGAGGGTTTGCGAGTTTTGTAGCGAGCAACCCTAACGCTCCTAAAAGGAA
ORF19C2B       (541)    AGAGGGTTTGCGAGCTTTGTCGCAAGCAACCCTAACGCCCTATAAGGAA
Consensus      (551)    AGAGGGTTTGCGAG TTTGT GC AGCAACCCTAACGCTCCTA AAGGAA 601                                               650
1111FutA       (585)    CGCTTTTTATGAGGCTTTAAACGCTATTGAGCCAGTTGCTGGGGGAGGGA
915A.cod(MWG)  (334)    --------------------------------------------------
19C2FutA.cod   (46)     --------------------------------------------------
26695A.cod     (591)    CGCTTTTTTATGACGCTCTAAATTCCATAGAGCCAGTTACTGGGGGAGGAA
1182B          (588)    TGCTTTCTATGACGTTTTAAATTCTATAGAGCCAGTTATTGGGGGAGGGA
1218B.nuc      (588)    TGCTTTCTATGACGCTTTAAATTCTATAGAGCCAGTTATTGGGGGAGGGA
ORF19C2B       (591)    CGCTTTCTATGAGGCTTTAAATTCTATTGAGCCAGTTACTGGGGGAGGGA
Consensus      (601)     GCTTT TATGA GCTTTAAATTCTAT GAGCCAGTTA TGGGGGAGGGA 651                                               700
1111FutA       (635)    GCGTGAAAAACACTTTAGGCTATAATGTCAAAAACAAGAGCGAGTTTTTA
915A.cod(MWG)  (334)    --------------------------------------------------
19C2FutA.cod   (46)     --------------------------------------------------
26695A.cod     (641)    GTGTGAGAAACACTTTAGGCTATAAGGTTGGAAACAAAAGCGAGTTTTTA
1182B          (638)    GCGTGAAAAACACTTTAGGCTATAACATTAAAAACAAGAGCGAGTTTTTA
1218B.nuc      (638)    GCGTGAAAAACACTTTAGGCTATAACATTAAAAACAAGAGCGAGTTTTTA
ORF19C2B       (641)    GCGTGAGAAACACTTTAGGCTATAACGTCAAAAACAAAAGCGAATTTTTG
Consensus      (651)    GCGTGA AAACACTTTAGGCTATAA  T AAAAACAA AGCGAGTTTTTA 701                                               750
1111FutA       (685)    AGCCAATACAAATTCAATCTGTGTTTTGAAAACAGTCAAGGCTATGGCTA
915A.cod(MWG)  (334)    --------------------------------------------------
19C2FutA.cod   (46)     --------------------------------------------------
26695A.cod     (691)    AGCCAATACAAGTTCAATCTCTGTTTTGAAAACTCGCAAGGTTATGGCTA
1182B          (688)    AGCCAATACAAATTCAATCTGTGTTTTGAAAAGTCACAAGGCTATGGCTA
1218B.nuc      (688)    AGCCAATACAAATTCAATCTGTGTTTTGAAAACTCACAAGGCTATGGCTA
ORF19C2B       (691)    AGCCAATACAAGTTCAATCTGTGCTTTGAAAACACTCAAGGCTATGGCTA
Consensus      (701)    AGCCAATACAA TTCAATCTGTGTTTTGAAAAC C CAAGGCTATGGCTA
```

FIG. 13 (CONT)

```
                          751                                                800
       1111FutA    (735)  TGTAACTGAAAAGATCATTGACGGTTATTTCAGCCATACCATTCCTATTT
    915A.cod(MWG)  (334)  --------------------------------------------------
      19C2FutA.cod  (46)  --------------------------------------------------
        26695A.cod (741)  TGTAACCGAAAAAATCCTTGATGCGTATTTTAGCCATACCATTCCTATTT
             1182B (738)  TGTAACTGAAAAAATCATTGACGCTTACTTTAGCCATACCATTCCTATTT
          1218B.nuc (738)  TGTAACTGAAAAAATCATTGACGCTTACTTTAGCCATACCATTCCTATTT
          ORF19C2B (741)  TGTTACTGAAAAAATCATTGACGCTTACTTCAGCCACACCATTCCTATTT
         Consensus (751)  TGTAACTGAAAAAATCATTGACGCTTA TT AGCCATACCATTCCTATTT 801                                                850
       1111FutA    (785)  ATTGGGGG--AGTCC-CAGCGTGGCGAAAGATTTTAACCCTAAGAGTTTT
    915A.cod(MWG)  (334)  --------------------------------------------------
      19C2FutA.cod  (46)  --------------------------------------------------
        26695A.cod (791)  ATTGGGGG--AGTCC-CAGCGTGGCGAAAGATTTTAACCCTAAAAGTTTT
             1182B (788)  ATTGGGGG--AGTCC-TAGCGTGGCACAAGATTTTAACCCTAAGAGTTTT
          1218B.nuc (788)  ATTGGGGG--AGTCC-TAGCGTGGCACAAGATTTTAACCCTAAGAGTTTT
          ORF19C2B (791)  ATTGGGGGGGAGTCCCTAGCGTGGCGAAAGATTTTAACCCC---------
         Consensus (801)  ATTGGGGG  AGTCC AGCGTGGC AAGATTTTAACCCTAA AGTTTT 851                                                900
       1111FutA    (832)  GTGAATGTCCATGATTTCAACAACTTTGATGAAGCGATTGACTATATCAG
    915A.cod(MWG)  (334)  --------------------------------------------------
      19C2FutA.cod  (46)  --------------------------------------------------
        26695A.cod (838)  GTGAATGTGCATGATTTCAACAACTTTGATGAAGCGATTGATTATATCAA
             1182B (835)  GTGAATGTTTGTGATTTTAAAGATTTTGATGAAGCGATTGATCATGTGCG
          1218B.nuc (835)  GTGAATGTTTGTGATTTTAAAGATTTTGATGAAGCGATTGATCATGTGCG
          ORF19C2B (832)  --------------------------------------------------
         Consensus (851)  GTGAATGT  TGATTT AA A TTTGATGAAGCGATTGA  AT T 901                                                950
       1111FutA    (882)  ATACTTGCACACGCACCCAAACGCTTATTTAGACATGCACTATGAAAACG
    915A.cod(MWG)  (334)  --------------------------------------------------
      19C2FutA.cod  (46)  --------------------------------------------------
        26695A.cod (888)  ATACCTGCAGACGCACCGAAACGCTTATTTAGACATGCTCTATGAAAACG
             1182B (885)  ATACTTGCACACGCACCCAAACGCTTATTTAGACATGCTTTATGAAAACG
          1218B.nuc (885)  ATACTTGCACACGCACCCAAACGCTTATTTAGACATGCTTTATGAAAACG
          ORF19C2B (832)  --------------------------------------------------
         Consensus (901)  ATAC TGCACACGCACCCAAACGCTTATTTAGACATGC  TATGAAAACC 951                                               1000
       1111FutA    (932)  CTTTAAACACTATTGATGGGAAAGCTTACTTTTACCAAAATTTGAGTTTT
    915A.cod(MWG)  (334)  --------------------------------------------------
      19C2FutA.cod  (46)  --------------------------------------------------
        26695A.cod (938)  CTTTAAACACCCTTGATGGGAAAGCTTACTTTTACCAAGATTTGAGTTTT
             1182B (935)  CTTTAAACACCCTTGATGGGAAAGCTTACTTTTACCAAAATTTGAGTTTT
          1218B.nuc (935)  CTTTAAACACCCTTGATGGGAAAGCTTACTTTTACCAAAATTTGAGTTTT
          ORF19C2B (832)  --------------------------------------------------
         Consensus (951)  CTTTAAACAC TTGATGGGAAAGCTTACTTTTACCAA ATTTGAGTTTT
```

FIG. 13 (CONT)

```
                         1001                                              1050
   1111FutA     (982)  AAAAAAATCCTAGATTTTTTTAAAACGATTTTAGAAAACGACACGATCTA
915A.cod(MWG)   (334)  --------------------------------------------------
 19C2FutA.cod    (46)  --------------------------------------------------
    26695A.cod  (988)  AAAAAAATCCTAGATTTTTTTAAAACGATTTTAGAAAACGATACGATTTA
          1182B (985)  AAAAAAATCCTAGATTTTTTTAAAACGATTTTAGAAAACGACACGATTTA
       1218B.nuc (985) AAAAAAATCCTAGATTTTTTTAAAACGATCTTAGAAAACGACACGATTTA
       ORF19C2B  (832) --------------------------------------------------
       Consensus (1001) AAAAAAATCCTAGATTTTTTTAAAACGAT TTAGAAAACGA ACGAT TA 1051                                              1100
   1111FutA    (1032)  TCACGATAACCC------TTTCATTTTCTATCGTGATTTGAATGAGCCTT
915A.cod(MWG)   (334)  --------------------------------------------------
 19C2FutA.cod    (46)  --------------------------------------------------
    26695A.cod (1038)  TCACAAATTCTAACATCTTTCATGTGGGAGTACGATCTGCATAAGCCGT
          1182B (1035) TCACGATAACCC------TTTTATTTTTTATCGTGATTTGAATGAGCCGT
       1218B.nuc (1035) TCACGATAACCC------TTTTATTTTTTATCGTGATTTGAATGAGCCGT
       ORF19C2B  (832) --------------------------------------------------
       Consensus (1051) TCAC A    C C        TTT AT T   A    GAT TG AT AGCC T 1101                                              1150
   1111FutA    (1076)  CAGTATCTATTGATGGT---TTGAGGGTTAATTATGATGATTTGAGGGTT
915A.cod(MWG)   (334)  --------------------------------------------------
 19C2FutA.cod    (46)  --------------------------------------------------
    26695A.cod (1088)  TAGTATCCATTGATGAT---TTGAGGGTTAATTATGATGATTTGAGGGTT
          1182B (1079) TAATATCTATTGATGATGATTTGAGGGTTAATTATGATGATTTGAGGGTT
       1218B.nuc (1079) TAATATCTATTGATGAT---TTGAGGGTTAATTATGATGATTTGAGGGTT
       ORF19C2B  (832) --------------------------------------------------
       Consensus (1101)   A TATC ATTGATG T    TTGAGGGTTAATTATGATGATTTGAGGGTT 1151                                              1200
   1111FutA    (1123)  AATTATGATGATTTGAGGGTTAATTATGATGATTTGAGGGTTAATTATGA
915A.cod(MWG)   (334)  --------------------------------------------------
 19C2FutA.cod    (46)  --------------------------------------------------
    26695A.cod (1135)  AATTATGACCGGCTTTTACAAAACGCTTCGCCTTTATTAGAACTCTCTCA
          1182B (1129) AATTATGATGATTTGAGGGTTAATTATGATGATTTGAGGGTTAATTATGA
       1218B.nuc (1126) AATTATGATGATTTGAGGGTTAATTATGATGATTTGAGGGTTAATTATGA
       ORF19C2B  (832) --------------------------------------------------
       Consensus (1151) AATTATGA        T       AA   T       TTT  G    T T A 1201                                              1250
   1111FutA    (1173)  GCGCCTTTTACAAAACGCCTCGCCTTTATTAGAACTCTCTCAAAACACCA
915A.cod(MWG)   (334)  --------------------------------------------------
 19C2FutA.cod    (46)  --------------------------------------------------
    26695A.cod (1185)  AAACACCACTTTTAAAATCTATCGCAAAGCTTATCAAAATCCTTGCCTT
          1182B (1179) TGATTTGAGGGTTAATTATGATGATTTGAGGGTTAATTATGATGATTTGA
       1218B.nuc (1176) TGATTTGAGGGTTAATTATGATGATTTGAGGGTTAATTATGATGATTTGA
       ORF19C2B  (832) --------------------------------------------------
       Consensus (1201)               AA
```

FIG. 13 (CONT)

```
                          1251                                              1300
     1111FutA    (1223)   CTTTTAAAATCTATCGCAAAGCTTATCAAAAATCCTTGCCTTTGTTGCGT
  915A.cod(MWG)  (334)    --------------------------------------------------
   19C2FutA.cod  (46)     --------------------------------------------------
      26695A.cod (1235)   TGTTGCGCGCGGTGAGAAAGTTGGTTAAAAAATTGGGTTTGTAA------
           1182B (1229)   GGGTTAATTATGATGATTTGAGGGTTAATTATGATGATTTGAGGGTTAAT
       1218B.nuc (1226)   GGGTTAATTATGATGATTTGAGGGTTAATTATGATGATTTGAGGGTTAAT
         ORF19C2B (832)   --------------------------------------------------
        Consensus (1251)      T                 T  A   A 1301                                              1350
     1111FutA    (1273)   GCCATAAGGAGATGGGTTAAAAAGTAA-----------------------
  915A.cod(MWG)  (334)    --------------------------------------------------
   19C2FutA.cod  (46)     --------------------------------------------------
      26695A.cod (1279)   --------------------------------------------------
           1182B (1279)   TATGATGATTTGAGGGTTAATTATGATGATTTGAGGGTTAATTATGAGCG
       1218B.nuc (1276)   TGTGATGATTTGAGGGTTAATTATGATGATTTGAGGGTTAATTATGAGCG
         ORF19C2B (832)   --------------------------------------------------
        Consensus (1301)

1351                                              1400
     1111FutA    (1300)   --------------------------------------------------
  915A.cod(MWG)  (334)    --------------------------------------------------
   19C2FutA.cod  (46)     --------------------------------------------------
      26695A.cod (1279)   --------------------------------------------------
           1182B (1329)   GCTCTTACAAAACGCCTCGCCTTTATTAGAACTCTCTCAAAACACCACTT
       1218B.nuc (1326)   GCTCTTACAAAACGCCTCGCCTTTATTAGAACTCTCTCAAAACACCACTT
         ORF19C2B (832)   --------------------------------------------------
        Consensus (1351)

1401                                              1450
     1111FutA    (1300)   --------------------------------------------------
  915A.cod(MWG)  (334)    --------------------------------------------------
   19C2FutA.cod  (46)     --------------------------------------------------
      26695A.cod (1279)   --------------------------------------------------
           1182B (1379)   TTAAAATCTATCGCAAAGCTTATCAAAAATCCTTACCTTTGTTGCGTGCG
       1218B.nuc (1376)   TTAAAATCTATCGCAAAGCTTATCAAAAATCCTTACCTTTGTTGCGTGCG
         ORF19C2B (832)   --------------------------------------------------
        Consensus (1401)

1451                    1483
     1111FutA    (1300)   ---------------------------------
  915A.cod(MWG)  (334)    ---------------------------------
   19C2FutA.cod  (46)     ---------------------------------
      26695A.cod (1279)   ---------------------------------
           1182B (1429)   GCGAGAAAGTTGATTAAAAAATTGGGTTTGTAA
       1218B.nuc (1426)   GCGAGAAAGTTGATTAAAAAATTGGGTTTGTAA
         ORF19C2B (832)   ---------------------------------
        Consensus (1451)
```

FIG. 14

Oligo Structures

Lacto-N-neo-Tetraose (LNnT)

Galβ1-4GlcNAcβ1-3Galβ1-4Glc

Lacto-N-Fucopentaose III (LNFP III)

Galβ1-4GlcNAcβ1-3Galβ1-4Glc
          |
          3
          |
       1αFucose

FIG. 15

Linkage Analysis by GC/MS

The samples were methylated, hydrolyzed, reduced with sodium borodeuteride, acetylated and analyzed by GC/MS along with samples of LNnT and LNF3.

⬆ A Glc vs. Glc-NAc value close to 1 favors fucosylation of Glc-NAc.
⬆ A Glc vs. Glc-NAc value close to 0 favors fucosylation of Glc

| *H. Pylori Strain* | Glc vs. Glc-NAc |
|---|---|
| 915A2 | 0.982 |
| 19C2A5 | 0.040 |
| 1111A2 | 0.975 |
| 19C2B1 | 0.991 |
| 1182B3 | 0.983 |

FIG. 16

1 Liter LNFIII Synthesis

| Batch Number | Resin Type | Total Yield | Actual Percent Recovery |
|---|---|---|---|
| 1-02 | MR3 NH$_4$HCO$_3$ column (1ml resin/1ml synthesis) | 1.567 g | 61% |
| 2-02 | MR3 NH$_4$HCO$_3$ column (1ml resin/1ml synthesis) | 1.760 g | 68% |
| 3-02 | Dowex1/Dowex 50 (2ml resin/1ml synthesis) | 1.221 g | 47% |

FIG. 17
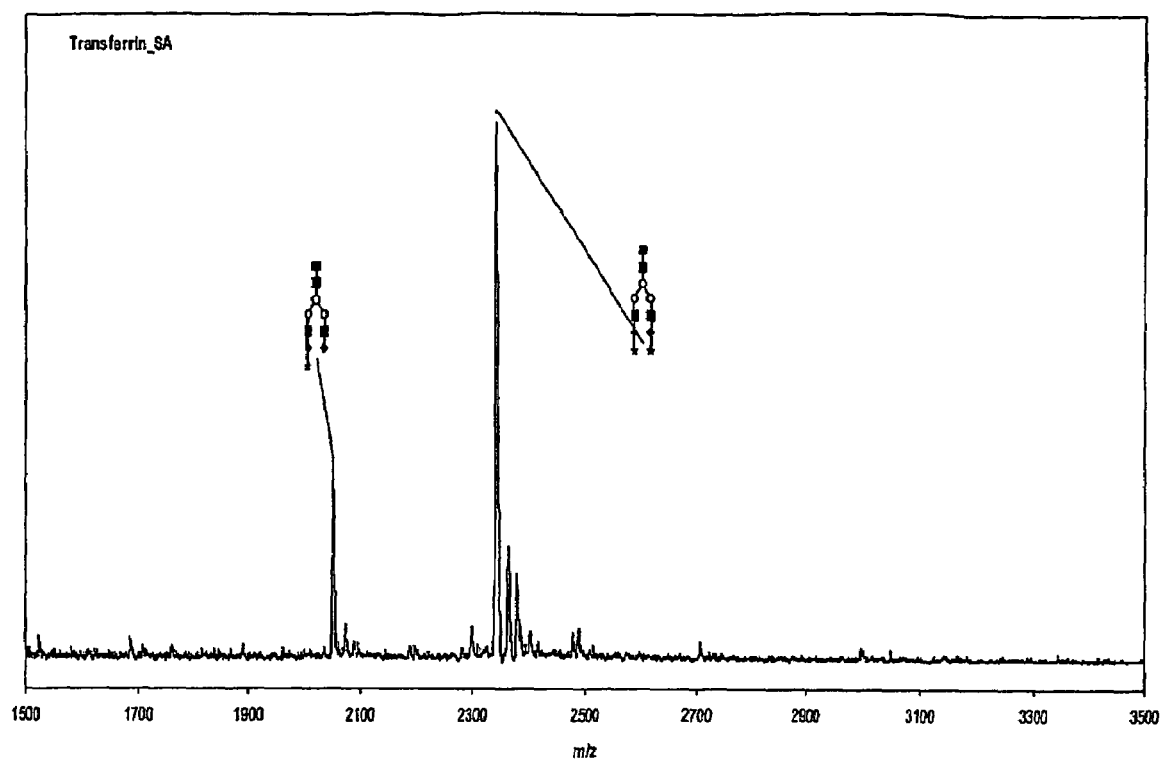
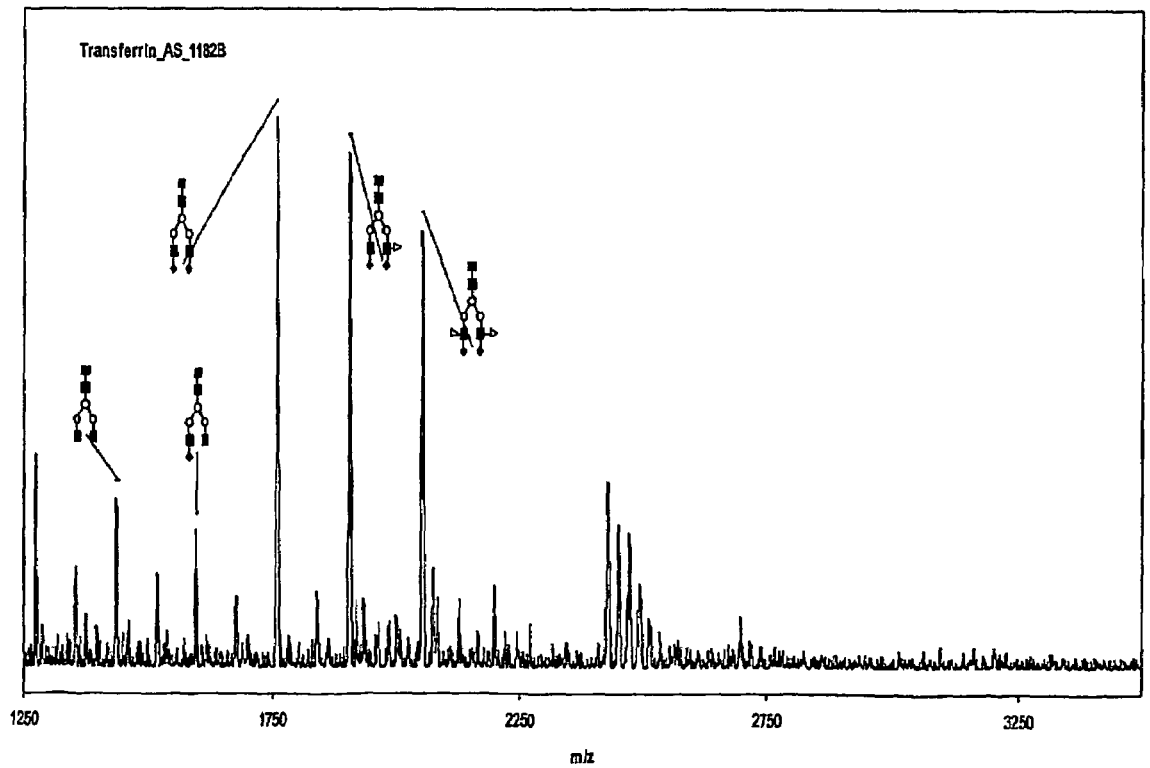

SEQUENCE LISTING

<160> NUMBER OF SEQ ID NOS: 76

<210> SEQ ID NO 1
<211> LENGTH: 1461
<212> TYPE: DNA
<213> ORGANISM: Helicobacter pylori
<220> FEATURE:
<223> OTHER INFORMATION: Helicobacter pylori strain 1182 FutB
      alpha-1,3/4-fucosyltransferase

<400> SEQUENCE: 1

```
atgttccaac ccctattaga cgcttatata gaaagcgctt ccattgaaaa aattacctct      60
aaatctcccc cccccctaaa aatcgctgtg gcgaattggt ggggagatga agaggttgaa    120
gaatttaaaa agaacattct ttatttttatt ctcagtcagc attacacaat caccctccac    180
caaaacccca acgaaccctc cgatctcgtc tttggcagtc ctattggatc agccagaaaa    240
atcttatcct atcaaaacgc aaaaagagtg ttttacaccg gtgaaaacga atcgcctaat    300
ttcaacctct ttgattacgc cataggcttt gatgaattgg attttagaga tcgttattta    360
agaatgcctt tatattatga tagactacac cataaagccg agagcgtgaa tgacaccact    420
tcgccttaca aactcaaacc tgacagcctt tatgctttaa aaaaaccctc ccatcatttt    480
aaagaaaacc accccaattt atgcgcagta gtgaacaatg agagcgatcc tttgaaaaga    540
gggtttgcga gttttgtagc gagcaaccct aacgctccta aaaggaatgc tttctatgac    600
gttttaaatt ctatagagcc agttattggg ggagggagcg tgaaaaacac tttaggctat    660
aacattaaaa acaagagcga gttttttaagc caatacaaat tcaatctgtg ttttgaaaac    720
tcacaaggct atggctatgt aactgaaaaa atcattgacg cttactttag ccataccatt    780
cctatttatt gggggagtcc tagcgtggca caagatttta accctaagag ttttgtgaat    840
gtttgtgatt ttaaagattt tgatgaagcg attgatcatg tgcgatactt gcacacgcac    900
ccaaacgctt atttagacat gctttatgaa aacccttttaa acaccctttga tgggaaagct    960 tacttttacc aaaatttgag ttttaaaaaa atcctagatt tttttaaaac gattttagaa    1020
aacgacacga tttcatcga taaccctttt atttttttatc gtgatttgaa tgagccgtta    1080
atatctattg atgatgattt gagggttaat tatgatgatt tgagggttaa ttatgatgat    1140
ttgagggtta attatgatga tttgagggtt aattatgatg atttgagggt taattatgat    1200
gatttgaggg ttaattatga tgatttgagg gttaattatg atgatttgag ggttaattat    1260
```

-continued

```
gatgatttga gggttaatta tgatgatttg agggttaatt atgatgattt gagggttaat    1320
tatgagcggc tcttacaaaa cgcctcgcct ttattagaac tctctcaaaa caccactttt    1380
aaaatctatc gcaaagctta tcaaaaatcc ttaccttttgt tgcgtgcggc gagaaagttg   1440
attaaaaaat tgggtttgta a                                              1461
```

<210> SEQ ID NO 2
<211> LENGTH: 486
<212> TYPE: PRT
<213> ORGANISM: Helicobacter pylori
<220> FEATURE:
<223> OTHER INFORMATION: Helicobacter pylori strain 1182 FutB
    alpha-1,3/4-fucosyltransferase

<400> SEQUENCE: 2

```
Met Phe Gln Pro Leu Leu Asp Ala Tyr Ile Glu Ser Ala Ser Ile Glu
  1               5                  10                  15

Lys Ile Thr Ser Lys Ser Pro Pro Leu Lys Ile Ala Val Ala Asn
             20                  25                  30

Trp Trp Gly Asp Glu Glu Val Glu Phe Lys Lys Asn Ile Leu Tyr
         35                  40                  45

Phe Ile Leu Ser Gln His Tyr Thr Ile Thr Leu His Gln Asn Pro Asn
 50                  55                  60

Glu Pro Ser Asp Leu Val Phe Gly Ser Pro Ile Gly Ser Ala Arg Lys
 65                  70                  75                  80

Ile Leu Ser Tyr Gln Asn Ala Lys Arg Val Phe Tyr Thr Gly Glu Asn
                 85                  90                  95

Glu Ser Pro Asn Phe Asn Leu Phe Asp Tyr Ala Ile Gly Phe Asp Glu
            100                 105                 110

Leu Asp Phe Arg Asp Arg Tyr Leu Arg Met Pro Leu Tyr Tyr Asp Arg
        115                 120                 125

Leu His His Lys Ala Glu Ser Val Asn Asp Thr Thr Ser Pro Tyr Lys
    130                 135                 140

Leu Lys Pro Asp Ser Leu Tyr Ala Leu Lys Lys Pro Ser His His Phe
145                 150                 155                 160

Lys Glu Asn His Pro Asn Leu Cys Ala Val Val Asn Asn Glu Ser Asp
                165                 170                 175

Pro Leu Lys Arg Gly Phe Ala Ser Phe Val Ala Ser Asn Pro Asn Ala
            180                 185                 190

Pro Lys Arg Asn Ala Phe Tyr Asp Val Leu Asn Ser Ile Glu Pro Val
        195                 200                 205

Ile Gly Gly Gly Ser Val Lys Asn Thr Leu Gly Tyr Asn Ile Lys Asn
    210                 215                 220

Lys Ser Glu Phe Leu Ser Gln Tyr Lys Phe Asn Leu Cys Phe Glu Asn
225                 230                 235                 240

Ser Gln Gly Tyr Gly Tyr Val Thr Glu Lys Ile Ile Asp Ala Tyr Phe
                245                 250                 255

Ser His Thr Ile Pro Ile Tyr Trp Gly Ser Pro Ser Val Ala Gln Asp
            260                 265                 270

Phe Asn Pro Lys Ser Phe Val Asn Val Cys Asp Phe Lys Asp Phe Asp
        275                 280                 285

Glu Ala Ile Asp His Val Arg Tyr Leu His Thr His Pro Asn Ala Tyr
    290                 295                 300

Leu Asp Met Leu Tyr Glu Asn Pro Leu Asn Thr Leu Asp Gly Lys Ala
305                 310                 315                 320
```

```
Tyr Phe Tyr Gln Asn Leu Ser Phe Lys Lys Ile Leu Asp Phe Phe Lys
            325                 330                 335

Thr Ile Leu Glu Asn Asp Thr Ile Tyr His Asp Asn Pro Phe Ile Phe
            340                 345                 350

Tyr Arg Asp Leu Asn Glu Pro Leu Ile Ser Ile Asp Asp Leu Arg
            355                 360                 365

Val Asn Tyr Asp Asp Leu Arg Val Asn Tyr Asp Leu Arg Val Asn
            370                 375                 380

Tyr Asp Asp Leu Arg Val Asn Tyr Asp Leu Arg Val Asn Tyr Asp
385                 390                 395                 400

Asp Leu Arg Val Asn Tyr Asp Leu Arg Val Asn Tyr Asp Leu
                405                 410                 415

Arg Val Asn Tyr Asp Asp Leu Arg Val Asn Tyr Asp Asp Leu Arg Val
                420                 425                 430

Asn Tyr Asp Asp Leu Arg Val Asn Tyr Glu Arg Leu Leu Gln Asn Ala
            435                 440                 445

Ser Pro Leu Leu Glu Leu Ser Gln Asn Thr Thr Phe Lys Ile Tyr Arg
    450                 455                 460

Lys Ala Tyr Gln Lys Ser Leu Pro Leu Leu Arg Ala Ala Arg Lys Leu
465                 470                 475                 480

Ile Lys Lys Leu Gly Leu
                485

<210> SEQ ID NO 3
<211> LENGTH: 1299
<212> TYPE: DNA
<213> ORGANISM: Helicobacter pylori
<220> FEATURE:
<223> OTHER INFORMATION: Helicobacter pylori strain 1111 FutA
      alpha-1,3/4-fucosyltransferase

<400> SEQUENCE: 3
atgttccaac ccctattaga tgcctttata gaaagcgctc cattgaaaaa atggcctcta      60
aatctccccc ccctaaaaat cgctgtggcg aattggtggg gagatgaaga attaaaaaaa    120
tttaaaaaga gcgttcttta ttttatccta agccagcatt acacaatcac tttacaccga    180
aaccctgata aacctgcgga catcgtcttt ggtaaccccc ttggatcagc cagaaaaatc    240
ttatcctatc aaaacgcaaa aagggtgttt tacaccggtg aaaatgaagt ccctaacttc    300
aacctctttg attacgccat aggctttgat gaattggact ttagagatcg ttatttgaga    360
atgcctttgt attatgccta tttgcattat aaagccgagc ttgttaatga caccacttcg    420
ccttataaac tccaacctga cagccttttat gctttaaaaa aaccctccca tcattttaaa    480
gaaaaccacc ccaatttgtg cgcagtagtg aataatgaga gtgatccttt gaaaagaggg    540
tttgcgagct tgtcgcaag caaccctaac gctcctagaa ggaacgcttt ttatgaggct    600
ttaaacgcta ttgagccagt tgctgggggga gggagcgtga aaaacacttt aggctataat    660
gtcaaaaaca gagcgagtt tttaagccaa tacaaattca atctgtgttt tgaaaacact    720
caaggctatg ctatgtaac tgaaaagatc attgacgctt atttcagcca taccattcct    780
atttattggg ggagtcccag cgtggcgaaa gattttaacc ctaagagttt tgtgaatgtc    840
catgatttca acaactttga tgaagcgatt gactatatca gatacttgca cacgcaccca    900
aacgcttatt tagacatgca ctatgaaaac cctttaaaca ctattgatgg aaagcttac     960 ttttaccaaa atttgagttt taaaaaaatc ctagatttt ttaaaaacgat ttagaaaac    1020 gacacgatct atcacgataa ccctttcatt ttctatcgtg atttgaatga gccttcagta    1080
```

```
tctattgatg gtttgagggt taattatgat gatttgaggg ttaattatga tgatttgagg      1140
gttaattatg atgatttgag ggttaattat gagcgccttt tacaaaacgc ctcgccttta      1200
ttagaactct ctcaaaacac cacttttaaa atctatcgca aagcttatca aaatccttg       1260 cctttgttgc gtgccataag gagatgggtt aaaaagtaa                             1299
```

<210> SEQ ID NO 4
<211> LENGTH: 432
<212> TYPE: PRT
<213> ORGANISM: Helicobacter pylori
<220> FEATURE:
<223> OTHER INFORMATION: Helicobacter pylori strain 1111 FutA
   alpha-1,3/4-fucosyltransferase

<400> SEQUENCE: 4

```
Met Phe Gln Pro Leu Leu Asp Ala Phe Ile Glu Ser Ala Pro Leu Lys
 1               5                  10                  15

Lys Trp Pro Leu Asn Leu Pro Pro Leu Lys Ile Ala Val Ala Asn Trp
            20                  25                  30

Trp Gly Asp Glu Glu Ile Lys Lys Phe Lys Lys Ser Val Leu Tyr Phe
        35                  40                  45

Ile Leu Ser Gln His Tyr Thr Ile Thr Leu His Arg Asn Pro Asp Lys
    50                  55                  60

Pro Ala Asp Ile Val Phe Gly Asn Pro Leu Gly Ser Ala Arg Lys Ile
65                  70                  75                  80

Leu Ser Tyr Gln Asn Ala Lys Arg Val Phe Tyr Thr Gly Glu Asn Glu
                85                  90                  95

Val Pro Asn Phe Asn Leu Phe Asp Tyr Ala Ile Gly Phe Asp Glu Leu
           100                 105                 110

Asp Phe Arg Asp Arg Tyr Leu Arg Met Pro Leu Tyr Tyr Ala Tyr Leu
       115                 120                 125

His Tyr Lys Ala Glu Leu Val Asn Asp Thr Thr Ser Pro Tyr Lys Leu
   130                 135                 140

Gln Pro Asp Ser Leu Tyr Ala Leu Lys Lys Pro Ser His His Phe Lys
145                 150                 155                 160

Glu Asn His Pro Asn Leu Cys Ala Val Val Asn Asn Glu Ser Asp Pro
               165                 170                 175

Leu Lys Arg Gly Phe Ala Ser Phe Val Ala Ser Asn Pro Asn Ala Pro
           180                 185                 190

Arg Arg Asn Ala Phe Tyr Glu Ala Leu Asn Ala Ile Glu Pro Val Ala
       195                 200                 205

Gly Gly Gly Ser Val Lys Asn Thr Leu Gly Tyr Asn Val Lys Asn Lys
   210                 215                 220

Ser Glu Phe Leu Ser Gln Tyr Lys Phe Asn Leu Cys Phe Glu Asn Thr
225                 230                 235                 240

Gln Gly Tyr Gly Tyr Val Thr Glu Lys Ile Ile Asp Ala Tyr Phe Ser
               245                 250                 255

His Thr Ile Pro Ile Tyr Trp Gly Ser Pro Ser Val Ala Lys Asp Phe
           260                 265                 270

Asn Pro Lys Ser Phe Val Asn Val His Asp Phe Asn Asn Phe Asp Glu
       275                 280                 285

Ala Ile Asp Tyr Ile Arg Tyr Leu His Thr His Pro Asn Ala Tyr Leu
   290                 295                 300

Asp Met His Tyr Glu Asn Pro Leu Asn Thr Ile Asp Gly Lys Ala Tyr
305                 310                 315                 320
```

Phe Tyr Gln Asn Leu Ser Phe Lys Lys Ile Leu Asp Phe Lys Thr
                325                 330                 335

Ile Leu Glu Asn Asp Thr Ile Tyr His Asp Asn Pro Phe Ile Phe Tyr
            340                 345                 350

Arg Asp Leu Asn Glu Pro Ser Val Ser Ile Asp Gly Leu Arg Val Asn
        355                 360                 365

Tyr Asp Asp Leu Arg Val Asn Tyr Asp Asp Leu Arg Val Asn Tyr Asp
    370                 375                 380

Asp Leu Arg Val Asn Tyr Glu Arg Leu Leu Gln Asn Ala Ser Pro Leu
385                 390                 395                 400

Leu Glu Leu Ser Gln Asn Thr Thr Phe Lys Ile Tyr Arg Lys Ala Tyr
                405                 410                 415

Gln Lys Ser Leu Pro Leu Leu Arg Ala Ile Arg Arg Trp Val Lys Lys
            420                 425                 430

<210> SEQ ID NO 5
<211> LENGTH: 1458
<212> TYPE: DNA
<213> ORGANISM: Helicobacter pylori
<220> FEATURE:
<223> OTHER INFORMATION: Helicobacter pylori strain 1218 FutB
      alpha-1,3/4-fucosyltransferase

<400> SEQUENCE: 5
atgttccaac ccctattaga cgcttatata gaaagcgctt ccattgaaaa aattacctct     60
aaatctcccc ccccccctaaa aatcgctgtg gcgaattggt ggggagatga agaggttgaa   120
gaatttaaaa agaacattct ttatttatt ctcagtcagc attacacaat caccctccac   180
caaaacccca cgaaccctc cgatctcgtc tttggcagtc ctattggatc agccagaaaa   240
atcttatcct atcaaaacgc aaaaagagtg ttttacaccg gtgaaaacga atcgcctaat   300
ttcaacctct tgattacgc cataggcttt gatgaattgg attttagaga tcgttattta   360
agaatgcctt tatattatga tagactacac cataaagccg agagcgtgaa tgacaccact   420
tcgccttaca aactcaaacc tgacagcctt tatgctttaa aaaaccctc ccatcatttt   480 aaagaaaacc accccaattt atgcgcagta gtgaacaatg agagcgatcc tttgaaaaga   540
gggtttgcga gttttgtagc gagcaacct aacgctccta aaggaatgc tttctatgac   600 gctttaaatt ctatagagcc agttattggg ggagggagcg tgaaaaacac tttaggctat   660
aacattaaaa acaagagcga gttttaagc caatacaaat tcaatctgtg ttttgaaaac   720
tcacaaggct atggctatgt aactgaaaaa atcattgacg cttactttag ccataccatt   780
cctatttatt ggggagtcc tagcgtggca caagattta accctaagag ttttgtgaat   840
gtttgtgatt ttaaagattt tgatgaagcg attgatcatg tgcgatactt gcacacgcac   900
ccaaacgctt atttagacat gctttatgaa aaccctttaa acacccttga tgggaaagct   960 tactttacc aaaatttgag tttttaaaaaa atcctagatt ttttttaaaac gatcttagaa  1020 aacgacacga tttatcacga taacccttttt attttttatc gtgatttgaa tgagccgtta  1080
atatctattg atgatttgag ggttaattat gatgatttga gggttaatta tgatgatttg  1140
agggttaatt atgatgattt gagggttaat tatgatgatt tgagggttaa ttatgatgat  1200
ttgagggtta attatgatga tttgagggtt aattatgatg atttgagggt taattatgat  1260
gatttgaggg ttaattgtga tgatttgagg gttaattatg atgatttgag ggttaattat  1320
gagcggctct tacaaaacgc ctcgcccttta ttagaactct ctcaaaacac cactttaaa  1380

-continued

```
atctatcgca aagcttatca aaaatcctta cctttgttgc gtgcggcgag aaagttgatt    1440
aaaaaattgg gtttgtaa                                                   1458
```

<210> SEQ ID NO 6
<211> LENGTH: 485
<212> TYPE: PRT
<213> ORGANISM: Helicobacter pylori
<220> FEATURE:
<223> OTHER INFORMATION: Helicobacter pylori strain 1218 FutB
      alpha-1,3/4-fucosyltransferase

<400> SEQUENCE: 6

```
Met Phe Gln Pro Leu Leu Asp Ala Tyr Ile Glu Ser Ala Ser Ile Glu
 1               5                  10                  15

Lys Ile Thr Ser Lys Ser Pro Pro Leu Lys Ile Ala Val Ala Asn
            20                  25                  30

Trp Trp Gly Asp Glu Glu Val Glu Glu Phe Lys Lys Asn Ile Leu Tyr
        35                  40                  45

Phe Ile Leu Ser Gln His Tyr Thr Ile Thr Leu His Gln Asn Pro Asn
    50                  55                  60

Glu Pro Ser Asp Leu Val Phe Gly Ser Pro Ile Gly Ser Ala Arg Lys
65                  70                  75                  80

Ile Leu Ser Tyr Gln Asn Ala Lys Arg Val Phe Tyr Thr Gly Glu Asn
                85                  90                  95

Glu Ser Pro Asn Phe Asn Leu Phe Asp Tyr Ala Ile Gly Phe Asp Glu
            100                 105                 110

Leu Asp Phe Arg Asp Arg Tyr Leu Arg Met Pro Leu Tyr Tyr Asp Arg
        115                 120                 125

Leu His His Lys Ala Glu Ser Val Asn Asp Thr Thr Ser Pro Tyr Lys
    130                 135                 140

Leu Lys Pro Asp Ser Leu Tyr Ala Leu Lys Lys Pro Ser His His Phe
145                 150                 155                 160

Lys Glu Asn His Pro Asn Leu Cys Ala Val Val Asn Asn Glu Ser Asp
                165                 170                 175

Pro Leu Lys Arg Gly Phe Ala Ser Phe Val Ala Ser Asn Pro Asn Ala
            180                 185                 190

Pro Lys Arg Asn Ala Phe Tyr Asp Ala Leu Asn Ser Ile Glu Pro Val
        195                 200                 205

Ile Gly Gly Gly Ser Val Lys Asn Thr Leu Gly Tyr Asn Ile Lys Asn
    210                 215                 220

Lys Ser Glu Phe Leu Ser Gln Tyr Lys Phe Asn Leu Cys Phe Glu Asn
225                 230                 235                 240

Ser Gln Gly Tyr Gly Tyr Val Thr Glu Lys Ile Ile Asp Ala Tyr Phe
                245                 250                 255

Ser His Thr Ile Pro Ile Tyr Trp Gly Ser Pro Ser Val Ala Gln Asp
            260                 265                 270

Phe Asn Pro Lys Ser Phe Val Asn Val Cys Asp Phe Lys Asp Phe Asp
        275                 280                 285

Glu Ala Ile Asp His Val Arg Tyr Leu His Thr His Pro Asn Ala Tyr
    290                 295                 300

Leu Asp Met Leu Tyr Glu Asn Pro Leu Asn Thr Leu Asp Gly Lys Ala
305                 310                 315                 320

Tyr Phe Tyr Gln Asn Leu Ser Phe Lys Lys Ile Leu Asp Phe Lys
                325                 330                 335

Thr Ile Leu Glu Asn Asp Thr Ile Tyr His Asp Asn Pro Phe Ile Phe
```

```
              340             345             350
Tyr Arg Asp Leu Asn Glu Pro Leu Ile Ser Ile Asp Asp Leu Arg Val
        355                 360                 365

Asn Tyr Asp Asp Leu Arg Val Asn Tyr Asp Asp Leu Arg Val Asn Tyr
    370                 375                 380

Asp Asp Leu Arg Val Asn Tyr Asp Asp Leu Arg Val Asn Tyr Asp Asp
385                 390                 395                 400

Leu Arg Val Asn Tyr Asp Asp Leu Arg Val Asn Tyr Asp Asp Leu Arg
                405                 410                 415

Val Asn Tyr Asp Asp Leu Arg Val Asn Cys Asp Asp Leu Arg Val Asn
            420                 425                 430

Tyr Asp Asp Leu Arg Val Asn Tyr Glu Arg Leu Leu Gln Asn Ala Ser
        435                 440                 445

Pro Leu Leu Glu Leu Ser Gln Asn Thr Thr Phe Lys Ile Tyr Arg Lys
    450                 455                 460

Ala Tyr Gln Lys Ser Leu Pro Leu Leu Arg Ala Ala Arg Lys Leu Ile
465                 470                 475                 480

Lys Lys Leu Gly Leu
            485

<210> SEQ ID NO 7
<211> LENGTH: 831
<212> TYPE: DNA
<213> ORGANISM: Helicobacter pylori
<220> FEATURE:
<223> OTHER INFORMATION: Helicobacter pylori strain 19C2 FutB
      alpha-1,3/4-fucosyltransferase

<400> SEQUENCE: 7
atgttccaac ccctattaga cgcttatata gacagcaccc gtttagatga aaccgattat      60
aagcccccat taaatatagc cctagcgaat tggtggcctt tggataaaag agaaagcaaa     120
gggtttagaa aaaaatttat cttacatttc attttaagtc agcattacac aatcgctctc     180
caccgaaacc ctgataaacc tgcggacatc gtttttggta ccccttgg atcagcaga      240 aaaatcctat cctatcaaaa cgctaaaagg gtgttttaca ccggtgaaaa cgaagtccct     300
aatttcaacc tctttgatta cgccataggc tttgatgaat ggactttag agatcgttat     360 ttgagaatgc ctttatatta tgatagacta caccataaag ccgagagcgt gaatgacacc     420
accgcacctt acaagattaa atctgacagc ctttatgctt taaaaaagcc ctcccatcat     480
tttaaagaaa accacccaca tttatgcgcg ctaatcaata tgagatcga tcctttgaaa     540 agagggtttg cgagctttgt cgcaagcaac cctaacgccc ctataaggaa cgctttctat     600
gaggctttaa attctattga gccagttact ggggagggga gcgtgagaaa cactttaggc     660
tataacgtca aaacaaaaa cgaattttt g agccaataca agttcaatct gtgctttgaa     720
aacactcaag gctatggcta tgttactgaa aaaatcattg acgcttactt cagccacacc     780
attcctattt attgggggggg agtccctagc gtggcgaaag attttaaccc c            831

<210> SEQ ID NO 8
<211> LENGTH: 277
<212> TYPE: PRT
<213> ORGANISM: Helicobacter pylori
<220> FEATURE:
<223> OTHER INFORMATION: Helicobacter pylori strain 19C2 FutB
      alpha-1,3/4-fucosyltransferase

<400> SEQUENCE: 8
```

```
Met Phe Gln Pro Leu Leu Asp Ala Tyr Ile Asp Ser Thr Arg Leu Asp
 1               5                  10                  15

Glu Thr Asp Tyr Lys Pro Leu Asn Ile Ala Leu Ala Asn Trp Trp
                 20                  25                  30

Pro Leu Asp Lys Arg Glu Ser Lys Gly Phe Arg Lys Lys Phe Ile Leu
             35                  40                  45

His Phe Ile Leu Ser Gln His Tyr Thr Ile Ala Leu His Arg Asn Pro
         50                  55                  60

Asp Lys Pro Ala Asp Ile Val Phe Gly Asn Pro Leu Gly Ser Ala Arg
 65                  70                  75                  80

Lys Ile Leu Ser Tyr Gln Asn Ala Lys Arg Val Phe Tyr Thr Gly Glu
                 85                  90                  95

Asn Glu Val Pro Asn Phe Asn Leu Phe Asp Tyr Ala Ile Gly Phe Asp
                100                 105                 110

Glu Leu Asp Phe Arg Asp Arg Tyr Leu Arg Met Pro Leu Tyr Tyr Asp
            115                 120                 125

Arg Leu His His Lys Ala Glu Ser Val Asn Asp Thr Thr Ala Pro Tyr
        130                 135                 140

Lys Ile Lys Ser Asp Ser Leu Tyr Ala Leu Lys Lys Pro Ser His His
145                 150                 155                 160

Phe Lys Glu Asn His Pro His Leu Cys Ala Leu Ile Asn Asn Glu Ile
                165                 170                 175

Asp Pro Leu Lys Arg Gly Phe Ala Ser Phe Val Ala Ser Asn Pro Asn
            180                 185                 190

Ala Pro Ile Arg Asn Ala Phe Tyr Glu Ala Leu Asn Ser Ile Glu Pro
        195                 200                 205

Val Thr Gly Gly Gly Ser Val Arg Asn Thr Leu Gly Tyr Asn Val Lys
    210                 215                 220

Asn Lys Asn Glu Phe Leu Ser Gln Tyr Lys Phe Asn Leu Cys Phe Glu
225                 230                 235                 240

Asn Thr Gln Gly Tyr Gly Tyr Val Thr Glu Lys Ile Ile Asp Ala Tyr
                245                 250                 255

Phe Ser His Thr Ile Pro Ile Tyr Trp Gly Val Pro Ser Val Ala
                260                 265                 270

Lys Asp Phe Asn Pro
        275

<210> SEQ ID NO 9
<211> LENGTH: 276
<212> TYPE: DNA
<213> ORGANISM: Helicobacter pylori
<220> FEATURE:
<223> OTHER INFORMATION: Helicobacter pylori strain 915 FutA
      alpha-1,3/4-fucosyltransferase

<400> SEQUENCE: 9
atggcctcta aatctccccc cctaaaaatc gctgtggcga attggtgggg agatgaagaa      60
attaaaaaat ttaaaagag cgttctttat tttatcctaa gccagcatta cacaatcact     120
ttacaccgaa accctgataa acctgcggac atcgtctttg gtaaccccct tggatcagcc     180
agaaaaatct tatcctatca aaacgcaaaa agggtgtttt acaccggtga aaatgaagtc     240
cctaacttca acctctttga ttcgccata ggcttt                               276

<210> SEQ ID NO 10
<211> LENGTH: 92
<212> TYPE: PRT
```

<213> ORGANISM: Helicobacter pylori
<220> FEATURE:
<223> OTHER INFORMATION: Helicobacter pylori strain 915 FutA
    alpha-1,3/4-fucosyltransferase

<400> SEQUENCE: 10

Met Ala Ser Lys Ser Pro Pro Leu Lys Ile Ala Val Ala Asn Trp Trp
1               5                   10                  15

Gly Asp Glu Glu Ile Lys Lys Phe Lys Lys Ser Val Leu Tyr Phe Ile
            20                  25                  30

Leu Ser Gln His Tyr Thr Ile Thr Leu His Arg Asn Pro Asp Lys Pro
        35                  40                  45

Ala Asp Ile Val Phe Gly Asn Pro Leu Gly Ser Ala Arg Lys Ile Leu
    50                  55                  60

Ser Tyr Gln Asn Ala Lys Arg Val Phe Tyr Thr Gly Glu Asn Glu Val
65                  70                  75                  80

Pro Asn Phe Asn Leu Phe Asp Tyr Ala Ile Gly Phe
                85                  90

<210> SEQ ID NO 11
<211> LENGTH: 1278
<212> TYPE: DNA
<213> ORGANISM: Helicobacter pylori
<220> FEATURE:
<223> OTHER INFORMATION: Helicobacter pylori strain 26695 FutA
    alpha-1,3/4-fucosyltransferase

<400> SEQUENCE: 11
atgttccaac ccctattaga cgcctttata gaaagcgctt ccattgaaaa aatggcctct      60
aaatctcccc ccccccccct aaaaatcgct gtggcgaatt ggtggggaga tgaagaaatt     120
aaagaattta aaagagcgt tctttatttt atcctaagcc aacgctacgc aatcaccctc     180
caccaaaacc ccaatgaatt ttcagatcta gttttagca atcctcttgg agcggctaga     240 aagatttat cttatcaaaa cactaaacga gtgttttaca ccggtgaaaa cgaatcacct     300
aatttcaacc tctttgatta cgccataggc tttgatgaat ggattttaa tgatcgttat     360 ttgagaatgc ctttgtatta tgcccatttg cactataaag ccgagcttgt taatgacacc     420
actgcgccct acaaactcaa agacaacagc ctttatgctt taaaaaaacc ctctcatcat     480
tttaaagaaa accaccctaa tttgtgcgca gtagtgaatg atgagagcga tcttttaaaa     540
agagggtttg ccagttttgt agcgagcaac gctaacgctc ctatgaggaa cgcttttttat     600 gacgctctaa attccataga gccagttact gggggaggaa gtgtgagaaa cacttttaggc     660 tataaggttg gaaacaaaag cgagtttttta agccaataca agttcaatct ctgttttgaa     720
aactcgcaag gttatggcta tgtaaccgaa aaaatccttg atgcgtattt tagccatacc     780
attcctattt attggggag tcccagcgtg gcgaaagatt ttaaccctaa aagttttgtg     840
aatgtgcatg atttcaacaa ctttgatgaa gcgattgatt atatcaaata cctgcacacg     900
cacccaaacg cttatttaga catgctctat gaaaaccctt taaacaccct tgatgggaaa     960
gcttactttt accaagattt gagtttttaa aaaatcctag attttttaa aacgatttta    1020 gaaaacgata cgatttatca caaattctca acatctttca tgtgggagta cgatctgcat    1080
aagccgttag tatccattga tgatttgagg gttaattatg atgatttgag ggttaattat    1140
gaccggcttt tacaaaacgc ttcgccttta ttagaactct ctcaaaacac cacttttaaa    1200
atctatcgca aagcttatca aaaatccttg cctttgttgc gcgcggtgag aaagttggtt    1260
aaaaaattgg gttttgtaa                                                1278

<210> SEQ ID NO 12
<211> LENGTH: 425
<212> TYPE: PRT
<213> ORGANISM: Helicobacter pylori
<220> FEATURE:
<223> OTHER INFORMATION: Helicobacter pylori strain 26695 FutA
     alpha-1,3/4-fucosyltransferase

<400> SEQUENCE: 12

```
Met Phe Gln Pro Leu Leu Asp Ala Phe Ile Glu Ser Ala Ser Ile Glu
  1               5                  10                  15

Lys Met Ala Ser Lys Ser Pro Pro Pro Leu Lys Ile Ala Val Ala
             20                  25                  30

Asn Trp Trp Gly Asp Glu Glu Ile Lys Glu Phe Lys Lys Ser Val Leu
         35                  40                  45

Tyr Phe Ile Leu Ser Gln Arg Tyr Ala Ile Thr Leu His Gln Asn Pro
     50                  55                  60

Asn Glu Phe Ser Asp Leu Val Phe Ser Asn Pro Leu Gly Ala Ala Arg
 65                  70                  75                  80

Lys Ile Leu Ser Tyr Gln Asn Thr Lys Arg Val Phe Tyr Thr Gly Glu
                 85                  90                  95

Asn Glu Ser Pro Asn Phe Asn Leu Phe Asp Tyr Ala Ile Gly Phe Asp
            100                 105                 110

Glu Leu Asp Phe Asn Asp Arg Tyr Leu Arg Met Pro Leu Tyr Tyr Ala
        115                 120                 125

His Leu His Tyr Lys Ala Glu Leu Val Asn Asp Thr Thr Ala Pro Tyr
    130                 135                 140

Lys Leu Lys Asp Asn Ser Leu Tyr Ala Leu Lys Lys Pro Ser His His
145                 150                 155                 160

Phe Lys Glu Asn His Pro Asn Leu Cys Ala Val Val Asn Asp Glu Ser
                165                 170                 175

Asp Leu Leu Lys Arg Gly Phe Ala Ser Phe Val Ala Ser Asn Ala Asn
            180                 185                 190

Ala Pro Met Arg Asn Ala Phe Tyr Asp Ala Leu Asn Ser Ile Glu Pro
        195                 200                 205

Val Thr Gly Gly Gly Ser Val Arg Asn Thr Leu Gly Tyr Lys Val Gly
    210                 215                 220

Asn Lys Ser Glu Phe Leu Ser Gln Tyr Lys Phe Asn Leu Cys Phe Glu
225                 230                 235                 240

Asn Ser Gln Gly Tyr Gly Tyr Val Thr Glu Lys Ile Leu Asp Ala Tyr
                245                 250                 255

Phe Ser His Thr Ile Pro Ile Tyr Trp Gly Ser Pro Ser Val Ala Lys
            260                 265                 270

Asp Phe Asn Pro Lys Ser Phe Val Asn Val His Asp Phe Asn Asn Phe
        275                 280                 285

Asp Glu Ala Ile Asp Tyr Ile Lys Tyr Leu His Thr His Pro Asn Ala
    290                 295                 300

Tyr Leu Asp Met Leu Tyr Glu Asn Pro Leu Asn Thr Leu Asp Gly Lys
305                 310                 315                 320

Ala Tyr Phe Tyr Gln Asp Leu Ser Phe Lys Lys Ile Leu Asp Phe Phe
                325                 330                 335

Lys Thr Ile Leu Glu Asn Asp Thr Ile Tyr His Lys Phe Ser Thr Ser
            340                 345                 350

Phe Met Trp Glu Tyr Asp Leu His Lys Pro Leu Val Ser Ile Asp Asp
```

```
               355                 360                 365
Leu Arg Val Asn Tyr Asp Asp Leu Arg Val Asn Tyr Asp Arg Leu Leu
            370                 375                 380
Gln Asn Ala Ser Pro Leu Leu Glu Leu Ser Gln Asn Thr Thr Phe Lys
385                 390                 395                 400
Ile Tyr Arg Lys Ala Tyr Gln Lys Ser Leu Pro Leu Leu Arg Ala Val
                405                 410                 415
Arg Lys Leu Val Lys Lys Leu Gly Leu
            420                 425
```

```
<210> SEQ ID NO 13
<211> LENGTH: 45
<212> TYPE: DNA
<213> ORGANISM: Helicobacter pylori
<220> FEATURE:
<223> OTHER INFORMATION: Helicobacter pylori strain 19C2 FutA
      alpha-1,3/4-fucosyltransferase

<400> SEQUENCE: 13
atgttccaac ccttactaga cgcctttata gaaagtgctc caatt              45

<210> SEQ ID NO 14
<211> LENGTH: 15
<212> TYPE: PRT
<213> ORGANISM: Helicobacter pylori
<220> FEATURE:
<223> OTHER INFORMATION: Helicobacter pylori strain 19C2 FutA
      alpha-1,3/4-fucosyltransferase

<400> SEQUENCE: 14

Met Phe Gln Pro Leu Leu Asp Ala Phe Ile Glu Ser Ala Pro Ile
1               5                   10                  15

<210> SEQ ID NO 15
<211> LENGTH: 283
<212> TYPE: PRT
<213> ORGANISM: Helicobacter pylori
<220> FEATURE:
<223> OTHER INFORMATION: Helicobacter pylori strain 1182 FutB
      alpha-1,3/4-fucosyltransferase amino acids 23-305,
      conserved fucosyltransferase catalytic domain

<400> SEQUENCE: 15

Pro Pro Pro Leu Lys Ile Ala Val Ala Asn Trp Trp Gly Asp Glu Glu
1               5                   10                  15

Val Glu Glu Phe Lys Lys Asn Ile Leu Tyr Phe Ile Leu Ser Gln His
            20                  25                  30

Tyr Thr Ile Thr Leu His Gln Asn Pro Asn Glu Pro Ser Asp Leu Val
        35                  40                  45

Phe Gly Ser Pro Ile Gly Ser Ala Arg Lys Ile Leu Ser Tyr Gln Asn
    50                  55                  60

Ala Lys Arg Val Phe Tyr Thr Gly Glu Asn Glu Ser Pro Asn Phe Asn
65                  70                  75                  80

Leu Phe Asp Tyr Ala Ile Gly Phe Asp Glu Leu Asp Phe Arg Asp Arg
                85                  90                  95

Tyr Leu Arg Met Pro Leu Tyr Tyr Asp Arg Leu His His Lys Ala Glu
            100                 105                 110

Ser Val Asn Asp Thr Thr Ser Pro Tyr Lys Leu Lys Pro Asp Ser Leu
        115                 120                 125

Tyr Ala Leu Lys Lys Pro Ser His His Phe Lys Glu Asn His Pro Asn
    130                 135                 140
```

```
Leu Cys Ala Val Val Asn Asn Glu Ser Asp Pro Leu Lys Arg Gly Phe
145                 150                 155                 160

Ala Ser Phe Val Ala Ser Asn Pro Asn Ala Pro Lys Arg Asn Ala Phe
                165                 170                 175

Tyr Asp Val Leu Asn Ser Ile Glu Pro Val Ile Gly Gly Gly Ser Val
            180                 185                 190

Lys Asn Thr Leu Gly Tyr Asn Ile Lys Asn Lys Ser Glu Phe Leu Ser
        195                 200                 205

Gln Tyr Lys Phe Asn Leu Cys Phe Glu Asn Ser Gln Gly Tyr Gly Tyr
    210                 215                 220

Val Thr Glu Lys Ile Ile Asp Ala Tyr Phe Ser His Thr Ile Pro Ile
225                 230                 235                 240

Tyr Trp Gly Ser Pro Ser Val Ala Gln Asp Phe Asn Pro Lys Ser Phe
                245                 250                 255

Val Asn Val Cys Asp Phe Lys Asp Phe Asp Glu Ala Ile Asp His Val
            260                 265                 270

Arg Tyr Leu His Thr His Pro Asn Ala Tyr Leu
        275                 280

<210> SEQ ID NO 16
<211> LENGTH: 291
<212> TYPE: PRT
<213> ORGANISM: Artificial Sequence
<220> FEATURE:
<223> OTHER INFORMATION: Description of Artificial Sequence:pfam00852,
      Glyco_transf_10 consensus sequence from
      glycosyltransferase family 10 fucosyltransferase
      family

<400> SEQUENCE: 16

Thr Val Pro Leu Leu Leu Ala Ile Tyr Thr Trp Trp Ser Leu Ile Glu
 1               5                  10                  15

Tyr Lys Glu Trp Lys Lys Ser Pro Ile Tyr Phe Ile Gly Ser Gln Ala
                20                  25                  30

Pro Gln Pro Pro Leu Arg Ile Leu Leu Trp Thr Trp Pro Phe Asn Gly
            35                  40                  45

Asn Pro Leu Ala Leu Ser Asp Cys Pro Leu Ser Tyr Gln Asn Thr Ala
        50                  55                  60

Arg Cys Arg Leu Thr Ala Asn Arg Ser Pro Leu Glu Ser Ala Asp Ala
65                  70                  75                  80

Val Leu Phe His His Arg Asp Leu Ser Lys Gly Phe Pro Asp Leu Pro
                85                  90                  95

Pro Ser Pro Arg Pro Pro Gly Gln Pro Trp Val Trp Ala Ser Met Glu
            100                 105                 110

Ser Pro Ser Asn Ser Gly Leu Asn Asp Leu Arg Asp Gly Tyr Phe Asn
        115                 120                 125

Trp Thr Leu Ser Tyr Arg Ala Asp Ser Asp Ala Phe His Pro Tyr Gly
    130                 135                 140

Tyr Leu Glu Pro Arg Leu Ser Gln Val Val Asn Ala Pro Leu Leu Ser
145                 150                 155                 160

Ala Lys Arg Lys Gly Ala Ala Trp Val Val Ser Asn Cys Asn Thr Arg
                165                 170                 175

Ser Lys Arg Glu Arg Phe Tyr Lys Gln Leu Asn Lys His Leu Gln Val
            180                 185                 190

Asp Val Gly Gly Arg Val Ala Asn Pro Leu Pro Leu Lys Val Gly Cys
        195                 200                 205
```

```
Leu Val Glu Thr Leu Ser Gln Tyr Lys Phe Tyr Leu Ala Phe Glu Asn
    210                 215                 220

Ser Gln His Tyr Asp Tyr Val Thr Glu Lys Leu Trp Lys Asn Ala Leu
225                 230                 235                 240

Gln Ala Gly Thr Ile Pro Val Val Leu Gly Pro Arg Ala Val Tyr Glu
                245                 250                 255

Asp Phe Val Pro Pro Lys Ser Phe Ile His Val Asp Asp Phe Lys Ser
                260                 265                 270

Pro Lys Glu Leu Ala Asp Tyr Leu Leu Tyr Leu Asp Thr Asn Pro Thr
            275                 280                 285

Ala Tyr Ser
    290

<210> SEQ ID NO 17
<211> LENGTH: 391
<212> TYPE: PRT
<213> ORGANISM: Helicobacter pylori
<220> FEATURE:
<223> OTHER INFORMATION: Helicobacter pylori strain 1111 FutA
      alpha-1,3/4-fucosyltransferase amino acids 27-417,
      conserved fucosyltransferase catalytic domain

<400> SEQUENCE: 17

Ile Ala Val Ala Asn Trp Trp Gly Asp Glu Glu Ile Lys Lys Phe Lys
1               5                   10                  15

Lys Ser Val Leu Tyr Phe Ile Leu Ser Gln His Tyr Thr Ile Thr Leu
                20                  25                  30

His Arg Asn Pro Asp Lys Pro Ala Asp Ile Val Phe Gly Asn Pro Leu
            35                  40                  45

Gly Ser Ala Arg Lys Ile Leu Ser Tyr Gln Asn Ala Lys Arg Val Phe
        50                  55                  60

Tyr Thr Gly Glu Asn Glu Val Pro Asn Phe Asn Leu Phe Asp Tyr Ala
65                  70                  75                  80

Ile Gly Phe Asp Glu Leu Asp Phe Arg Asp Arg Tyr Leu Arg Met Pro
                85                  90                  95

Leu Tyr Tyr Ala Tyr Leu His Tyr Lys Ala Glu Leu Val Asn Asp Thr
            100                 105                 110

Thr Ser Pro Tyr Lys Leu Gln Pro Asp Ser Leu Tyr Ala Leu Lys Lys
        115                 120                 125

Pro Ser His His Phe Lys Glu Asn His Pro Asn Leu Cys Ala Val Val
    130                 135                 140

Asn Asn Glu Ser Asp Pro Leu Lys Arg Gly Phe Ala Ser Phe Val Ala
145                 150                 155                 160

Ser Asn Pro Asn Ala Pro Arg Arg Asn Ala Phe Tyr Glu Ala Leu Asn
                165                 170                 175

Ala Ile Glu Pro Val Ala Gly Gly Gly Ser Val Lys Asn Thr Leu Gly
            180                 185                 190

Tyr Asn Val Lys Asn Lys Ser Glu Phe Leu Ser Gln Tyr Lys Phe Asn
        195                 200                 205

Leu Cys Phe Glu Asn Thr Gln Gly Tyr Gly Tyr Val Thr Glu Lys Ile
    210                 215                 220

Ile Asp Ala Tyr Phe Ser His Thr Ile Pro Ile Tyr Trp Gly Ser Pro
225                 230                 235                 240

Ser Val Ala Lys Asp Phe Asn Pro Lys Ser Phe Val Asn Val His Asp
                245                 250                 255
```

```
Phe Asn Asn Phe Asp Glu Ala Ile Asp Tyr Ile Arg Tyr Leu His Thr
            260                 265                 270

His Pro Asn Ala Tyr Leu Asp Met His Tyr Glu Asn Pro Leu Asn Thr
        275                 280                 285

Ile Asp Gly Lys Ala Tyr Phe Tyr Gln Asn Leu Ser Phe Lys Lys Ile
    290                 295                 300

Leu Asp Phe Phe Lys Thr Ile Leu Glu Asn Asp Thr Ile Tyr His Asp
305                 310                 315                 320

Asn Pro Phe Ile Phe Tyr Arg Asp Leu Asn Glu Pro Ser Val Ser Ile
                325                 330                 335

Asp Gly Leu Arg Val Asn Tyr Asp Asp Leu Arg Val Asn Tyr Asp Asp
            340                 345                 350

Leu Arg Val Asn Tyr Asp Asp Leu Arg Val Asn Tyr Glu Arg Leu Leu
        355                 360                 365

Gln Asn Ala Ser Pro Leu Leu Glu Leu Ser Gln Asn Thr Thr Phe Lys
    370                 375                 380

Ile Tyr Arg Lys Ala Tyr Gln
385                 390

<210> SEQ ID NO 18
<211> LENGTH: 336
<212> TYPE: PRT
<213> ORGANISM: Artificial Sequence
<220> FEATURE:
<223> OTHER INFORMATION: Description of Artificial Sequence:pfam00852,
      Glyco_transf_10 consensus sequence from
      glycosyltransferase family 10 fucosyltransferase
      family

<400> SEQUENCE: 18

Leu Ala Ile Tyr Thr Trp Trp Ser Leu Ile Glu Tyr Lys Glu Trp Lys
1               5                   10                  15

Lys Ser Pro Ile Tyr Phe Ile Gly Ser Gln Ala Pro Gln Pro Pro Leu
            20                  25                  30

Arg Ile Leu Leu Trp Thr Trp Pro Phe Asn Gly Asn Pro Leu Ala Leu
        35                  40                  45

Ser Asp Cys Pro Leu Ser Tyr Gln Asn Thr Ala Arg Cys Arg Leu Thr
    50                  55                  60

Ala Asn Arg Ser Pro Leu Glu Ser Ala Asp Ala Val Leu Phe His His
65                  70                  75                  80

Arg Asp Leu Ser Lys Gly Phe Pro Asp Leu Pro Pro Ser Pro Arg Pro
                85                  90                  95

Pro Gly Gln Pro Trp Val Trp Ala Ser Met Glu Ser Pro Ser Asn Ser
            100                 105                 110

Gly Leu Asn Asp Leu Arg Asp Gly Tyr Phe Asn Trp Thr Leu Ser Tyr
        115                 120                 125

Arg Ala Asp Ser Asp Ala Phe His Pro Tyr Gly Tyr Leu Glu Pro Arg
    130                 135                 140

Leu Ser Gln Val Val Asn Ala Pro Leu Leu Ser Ala Lys Arg Lys Gly
145                 150                 155                 160

Ala Ala Trp Val Val Ser Asn Cys Asn Thr Arg Ser Lys Arg Glu Arg
                165                 170                 175

Phe Tyr Lys Gln Leu Asn Lys His Leu Gln Val Asp Val Gly Gly Arg
            180                 185                 190

Val Ala Asn Pro Leu Pro Leu Lys Val Gly Cys Leu Val Glu Thr Leu
        195                 200                 205
```

```
Ser Gln Tyr Lys Phe Tyr Leu Ala Phe Glu Asn Ser Gln His Tyr Asp
    210                 215                 220

Tyr Val Thr Glu Lys Leu Trp Lys Asn Ala Leu Gln Ala Gly Thr Ile
225                 230                 235                 240

Pro Val Leu Gly Pro Arg Ala Val Tyr Glu Asp Phe Val Pro Pro
                245                 250                 255

Lys Ser Phe Ile His Val Asp Asp Phe Lys Ser Pro Lys Glu Leu Ala
                260                 265                 270

Asp Tyr Leu Leu Tyr Leu Asp Thr Asn Pro Thr Ala Tyr Ser Glu Tyr
            275                 280                 285

Phe Glu Trp Arg Tyr Asp Leu Arg Val Arg Leu Phe Ser Trp Asp Ala
    290                 295                 300

Leu Arg Tyr Asp Glu Gly Phe Cys Arg Val Cys Arg Leu Leu Gln Asn
305                 310                 315                 320

Ala Pro Asp Arg Tyr Lys Thr Tyr Pro Asn Ile Ala Lys Trp Phe Gln
                325                 330                 335

<210> SEQ ID NO 19
<211> LENGTH: 377
<212> TYPE: PRT
<213> ORGANISM: Helicobacter pylori
<220> FEATURE:
<223> OTHER INFORMATION: Helicobacter pylori strain 1218 FutB
      alpha-1,3/4-fucosyltransferase amino acids 23-399,
      conserved fucosyltransferase catalytic domain

<400> SEQUENCE: 19

Pro Pro Pro Leu Lys Ile Ala Val Ala Asn Trp Trp Gly Asp Glu Glu
1               5                   10                  15

Val Glu Glu Phe Lys Lys Asn Ile Leu Tyr Phe Ile Leu Ser Gln His
                20                  25                  30

Tyr Thr Ile Thr Leu His Gln Asn Pro Asn Glu Pro Ser Asp Leu Val
            35                  40                  45

Phe Gly Ser Pro Ile Gly Ser Ala Arg Lys Ile Leu Ser Tyr Gln Asn
    50                  55                  60

Ala Lys Arg Val Phe Tyr Thr Gly Glu Asn Glu Ser Pro Asn Phe Asn
65                  70                  75                  80

Leu Phe Asp Tyr Ala Ile Gly Phe Asp Glu Leu Asp Phe Arg Asp Arg
                85                  90                  95

Tyr Leu Arg Met Pro Leu Tyr Tyr Asp Arg Leu His His Lys Ala Glu
            100                 105                 110

Ser Val Asn Asp Thr Thr Ser Pro Tyr Lys Leu Lys Pro Asp Ser Leu
        115                 120                 125

Tyr Ala Leu Lys Lys Pro Ser His His Phe Lys Glu Asn His Pro Asn
    130                 135                 140

Leu Cys Ala Val Val Asn Asn Glu Ser Asp Pro Leu Lys Arg Gly Phe
145                 150                 155                 160

Ala Ser Phe Val Ala Ser Asn Pro Asn Ala Pro Lys Arg Asn Ala Phe
                165                 170                 175

Tyr Asp Ala Leu Asn Ser Ile Glu Pro Val Ile Gly Gly Gly Ser Val
            180                 185                 190

Lys Asn Thr Leu Gly Tyr Asn Ile Lys Asn Lys Ser Glu Phe Leu Ser
        195                 200                 205

Gln Tyr Lys Phe Asn Leu Cys Phe Glu Asn Ser Gln Gly Tyr Gly Tyr
    210                 215                 220

Val Thr Glu Lys Ile Ile Asp Ala Tyr Phe Ser His Thr Ile Pro Ile
```

```
                225                 230                 235                 240
Tyr Trp Gly Ser Pro Ser Val Ala Gln Asp Phe Asn Pro Lys Ser Phe
                245                 250                 255

Val Asn Val Cys Asp Phe Lys Asp Phe Asp Glu Ala Ile Asp His Val
            260                 265                 270

Arg Tyr Leu His Thr His Pro Asn Ala Tyr Leu Asp Met Leu Tyr Glu
        275                 280                 285

Asn Pro Leu Asn Thr Leu Asp Gly Lys Ala Tyr Phe Tyr Gln Asn Leu
    290                 295                 300

Ser Phe Lys Lys Ile Leu Asp Phe Phe Lys Thr Ile Leu Glu Asn Asp
305                 310                 315                 320

Thr Ile Tyr His Asp Asn Pro Phe Ile Phe Tyr Arg Asp Leu Asn Glu
                325                 330                 335

Pro Leu Ile Ser Ile Asp Asp Leu Arg Val Asn Tyr Asp Asp Leu Arg
            340                 345                 350

Val Asn Tyr Asp Asp Leu Arg Val Asn Tyr Asp Asp Leu Arg Val Asn
        355                 360                 365

Tyr Asp Asp Leu Arg Val Asn Tyr Asp
    370                 375

<210> SEQ ID NO 20
<211> LENGTH: 341
<212> TYPE: PRT
<213> ORGANISM: Artificial Sequence
<220> FEATURE:
<223> OTHER INFORMATION: Description of Artificial Sequence:pfam00852,
      Glyco_transf_10 consensus sequence from
      glycosyltransferase family 10 fucosyltransferase
      family

<400> SEQUENCE: 20

Thr Val Pro Leu Leu Leu Ala Ile Tyr Thr Trp Trp Ser Leu Ile Glu
  1               5                  10                  15

Tyr Lys Glu Trp Lys Lys Ser Pro Ile Tyr Phe Ile Gly Ser Gln Ala
             20                  25                  30

Pro Gln Pro Pro Leu Arg Ile Leu Leu Trp Thr Trp Pro Phe Asn Gly
         35                  40                  45

Asn Pro Leu Ala Leu Ser Asp Cys Pro Leu Ser Tyr Gln Asn Thr Ala
     50                  55                  60

Arg Cys Arg Leu Thr Ala Asn Arg Ser Pro Leu Glu Ser Ala Asp Ala
 65                  70                  75                  80

Val Leu Phe His His Arg Asp Leu Ser Lys Gly Phe Pro Asp Leu Pro
                 85                  90                  95

Pro Ser Pro Arg Pro Gly Gln Pro Trp Val Trp Ala Ser Met Glu
            100                 105                 110

Ser Pro Ser Asn Ser Gly Leu Asn Asp Leu Arg Asp Gly Tyr Phe Asn
        115                 120                 125

Trp Thr Leu Ser Tyr Arg Ala Asp Ser Asp Ala Phe His Pro Tyr Gly
    130                 135                 140

Tyr Leu Glu Pro Arg Leu Ser Gln Val Val Asn Ala Pro Leu Leu Ser
145                 150                 155                 160

Ala Lys Arg Lys Gly Ala Ala Trp Val Val Ser Asn Cys Asn Thr Arg
                165                 170                 175

Ser Lys Arg Glu Arg Phe Tyr Lys Gln Leu Asn Lys His Leu Gln Val
            180                 185                 190

Asp Val Gly Gly Arg Val Ala Asn Pro Leu Pro Leu Lys Val Gly Cys
```

```
                    195                 200                 205
Leu Val Glu Thr Leu Ser Gln Tyr Lys Phe Tyr Leu Ala Phe Glu Asn
    210                 215                 220

Ser Gln His Tyr Asp Tyr Val Thr Glu Lys Leu Trp Lys Asn Ala Leu
225                 230                 235                 240

Gln Ala Gly Thr Ile Pro Val Val Leu Gly Pro Arg Ala Val Tyr Glu
                245                 250                 255

Asp Phe Val Pro Pro Lys Ser Phe Ile His Val Asp Asp Phe Lys Ser
                260                 265                 270

Pro Lys Glu Leu Ala Asp Tyr Leu Leu Tyr Leu Asp Thr Asn Pro Thr
            275                 280                 285

Ala Tyr Ser Glu Tyr Phe Glu Trp Arg Tyr Asp Leu Arg Val Arg Leu
        290                 295                 300

Phe Ser Trp Asp Ala Leu Arg Tyr Asp Glu Gly Phe Cys Arg Val Cys
305                 310                 315                 320

Arg Leu Leu Gln Asn Ala Pro Asp Arg Tyr Lys Thr Tyr Pro Asn Ile
                325                 330                 335

Ala Lys Trp Phe Gln
            340

<210> SEQ ID NO 21
<211> LENGTH: 256
<212> TYPE: PRT
<213> ORGANISM: Helicobacter pylori
<220> FEATURE:
<223> OTHER INFORMATION: Helicobacter pylori strain 19C2 FutB
      alpha-1,3/4-fucosyltransferase amino acids 23-377,
      conserved fucosyltransferase catalytic domain

<400> SEQUENCE: 21

Pro Pro Leu Asn Ile Ala Leu Ala Asn Trp Trp Pro Leu Asp Lys Arg
  1               5                  10                  15

Glu Ser Lys Gly Phe Arg Lys Lys Phe Ile Leu His Phe Ile Leu Ser
                20                  25                  30

Gln His Tyr Thr Ile Ala Leu His Arg Asn Pro Asp Lys Pro Ala Asp
            35                  40                  45

Ile Val Phe Gly Asn Pro Leu Gly Ser Ala Arg Lys Ile Leu Ser Tyr
        50                  55                  60

Gln Asn Ala Lys Arg Val Phe Tyr Thr Gly Glu Asn Glu Val Pro Asn
65                  70                  75                  80

Phe Asn Leu Phe Asp Tyr Ala Ile Gly Phe Asp Glu Leu Asp Phe Arg
                85                  90                  95

Asp Arg Tyr Leu Arg Met Pro Leu Tyr Tyr Asp Arg Leu His His Lys
            100                 105                 110

Ala Glu Ser Val Asn Asp Thr Thr Ala Pro Tyr Lys Ile Lys Ser Asp
        115                 120                 125

Ser Leu Tyr Ala Leu Lys Lys Pro Ser His His Phe Lys Glu Asn His
    130                 135                 140

Pro His Leu Cys Ala Leu Ile Asn Asn Glu Ile Asp Pro Leu Lys Arg
145                 150                 155                 160

Gly Phe Ala Ser Phe Val Ala Ser Asn Pro Asn Ala Pro Ile Arg Asn
                165                 170                 175

Ala Phe Tyr Glu Ala Leu Asn Ser Ile Glu Pro Val Thr Gly Gly Gly
            180                 185                 190

Ser Val Arg Asn Thr Leu Gly Tyr Asn Val Lys Asn Lys Asn Glu Phe
        195                 200                 205
```

-continued

```
Leu Ser Gln Tyr Lys Phe Asn Leu Cys Phe Glu Asn Thr Gln Gly Tyr
    210                 215                 220

Gly Tyr Val Thr Glu Lys Ile Ile Asp Ala Tyr Phe Ser His Thr Ile
225                 230                 235                 240

Pro Ile Tyr Trp Gly Gly Val Pro Ser Val Ala Lys Asp Phe Asn Pro
                245                 250                 255

<210> SEQ ID NO 22
<211> LENGTH: 259
<212> TYPE: PRT
<213> ORGANISM: Artificial Sequence
<220> FEATURE:
<223> OTHER INFORMATION: Description of Artificial Sequence:pfam00852,
      Glyco_transf_10 consensus sequence from
      glycosyltransferase family 10 fucosyltransferase
      family

<400> SEQUENCE: 22

Val Pro Leu Leu Leu Ala Ile Tyr Thr Trp Trp Ser Leu Ile Glu Tyr
  1               5                  10                  15

Lys Glu Trp Lys Lys Ser Pro Ile Tyr Phe Ile Gly Ser Gln Ala Pro
             20                  25                  30

Gln Pro Pro Leu Arg Ile Leu Leu Trp Thr Trp Pro Phe Asn Gly Asn
         35                  40                  45

Pro Leu Ala Leu Ser Asp Cys Pro Leu Ser Tyr Gln Asn Thr Ala Arg
     50                  55                  60

Cys Arg Leu Thr Ala Asn Arg Ser Pro Leu Glu Ser Ala Asp Ala Val
 65                  70                  75                  80

Leu Phe His His Arg Asp Leu Ser Lys Gly Phe Pro Asp Leu Pro Pro
                 85                  90                  95

Ser Pro Arg Pro Pro Gly Gln Pro Trp Val Trp Ala Ser Met Glu Ser
                100                 105                 110

Pro Ser Asn Ser Gly Leu Asn Asp Leu Arg Asp Gly Tyr Phe Asn Trp
            115                 120                 125

Thr Leu Ser Tyr Arg Ala Asp Ser Asp Ala Phe His Pro Tyr Gly Tyr
    130                 135                 140

Leu Glu Pro Arg Leu Ser Gln Val Val Asn Ala Pro Leu Leu Ser Ala
145                 150                 155                 160

Lys Arg Lys Gly Ala Ala Trp Val Val Ser Asn Cys Asn Thr Arg Ser
                165                 170                 175

Lys Arg Glu Arg Phe Tyr Lys Gln Leu Asn Lys His Leu Gln Val Asp
            180                 185                 190

Val Gly Gly Arg Val Ala Asn Pro Leu Pro Leu Lys Val Gly Cys Leu
        195                 200                 205

Val Glu Thr Leu Ser Gln Tyr Lys Phe Tyr Leu Ala Phe Glu Asn Ser
    210                 215                 220

Gln His Tyr Asp Tyr Val Thr Glu Lys Leu Trp Lys Asn Ala Leu Gln
225                 230                 235                 240

Ala Gly Thr Ile Pro Val Val Leu Gly Pro Arg Ala Val Tyr Glu Asp
                245                 250                 255

Phe Val Pro

<210> SEQ ID NO 23
<211> LENGTH: 245
<212> TYPE: PRT
<213> ORGANISM: Helicobacter pylori
<220> FEATURE:
```

-continued

```
<223> OTHER INFORMATION: Helicobacter pylori strain 1111 FutA
      alpha-1,3/4-fucosyltransferase

<400> SEQUENCE: 23

Met Phe Gln Pro Leu Leu Asp Ala Phe Ile Glu Ser Ala Pro Leu Lys
1               5                   10                  15

Lys Trp Pro Leu Asn Leu Pro Pro Leu Lys Ile Ala Val Ala Asn Trp
            20                  25                  30

Trp Gly Asp Glu Glu Ile Lys Lys Phe Lys Lys Ser Val Leu Tyr Phe
        35                  40                  45

Ile Leu Ser Gln His Tyr Thr Ile Thr Leu His Arg Asn Pro Asp Lys
    50                  55                  60

Pro Ala Asp Ile Val Phe Gly Asn Pro Leu Gly Ser Ala Arg Lys Ile
65                  70                  75                  80

Leu Ser Tyr Gln Asn Ala Lys Arg Val Phe Tyr Thr Gly Glu Asn Glu
                85                  90                  95

Val Pro Asn Phe Asn Leu Phe Asp Tyr Ala Ile Gly Phe Asp Glu Leu
            100                 105                 110

Asp Phe Arg Asp Arg Tyr Leu Arg Met Pro Leu Tyr Tyr Ala Tyr Leu
        115                 120                 125

His Tyr Lys Ala Glu Leu Val Asn Asp Thr Thr Ser Pro Tyr Lys Leu
    130                 135                 140

Gln Pro Asp Ser Leu Tyr Ala Leu Lys Lys Pro Ser His His Phe Lys
145                 150                 155                 160

Glu Asn His Pro Asn Leu Cys Ala Val Val Asn Asn Glu Ser Asp Pro
                165                 170                 175

Leu Lys Arg Gly Phe Ala Ser Phe Val Ala Ser Asn Pro Asn Ala Pro
            180                 185                 190

Arg Arg Asn Ala Phe Tyr Glu Ala Leu Asn Ala Ile Glu Pro Val Ala
        195                 200                 205

Gly Gly Gly Ser Val Lys Asn Thr Leu Gly Tyr Asn Val Lys Asn Lys
    210                 215                 220

Ser Glu Phe Leu Ser Gln Tyr Lys Phe Asn Leu Cys Phe Glu Asn Thr
225                 230                 235                 240

Gln Gly Tyr Gly Tyr
                245

<210> SEQ ID NO 24
<211> LENGTH: 247
<212> TYPE: PRT
<213> ORGANISM: Helicobacter pylori
<220> FEATURE:
<223> OTHER INFORMATION: Helicobacter pylori strain 26695 FutA
      alpha-1,3/4-fucosyltransferase

<400> SEQUENCE: 24

Met Phe Gln Pro Leu Leu Asp Ala Phe Ile Glu Ser Ala Ser Ile Glu
1               5                   10                  15

Lys Met Ala Ser Lys Ser Pro Pro Pro Leu Lys Ile Ala Val Ala
            20                  25                  30

Asn Trp Trp Gly Asp Glu Glu Ile Lys Glu Phe Lys Lys Ser Val Leu
        35                  40                  45

Tyr Phe Ile Leu Ser Gln Arg Tyr Ala Ile Thr Leu His Gln Asn Pro
    50                  55                  60

Asn Glu Phe Ser Asp Leu Val Phe Ser Asn Pro Leu Gly Ala Ala Arg
65                  70                  75                  80
```

```
Lys Ile Leu Ser Tyr Gln Asn Thr Lys Arg Val Phe Tyr Thr Gly Glu
                85                  90                  95

Asn Glu Ser Pro Asn Phe Asn Leu Phe Asp Tyr Ala Ile Gly Phe Asp
            100                 105                 110

Glu Leu Asp Phe Asn Asp Arg Tyr Leu Arg Met Pro Leu Tyr Tyr Ala
        115                 120                 125

His Leu His Tyr Lys Ala Glu Leu Val Asn Asp Thr Thr Ala Pro Tyr
    130                 135                 140

Lys Leu Lys Asp Asn Ser Leu Tyr Ala Leu Lys Lys Pro Ser His His
145                 150                 155                 160

Phe Lys Glu Asn His Pro Asn Leu Cys Ala Val Val Asn Asp Glu Ser
                165                 170                 175

Asp Leu Leu Lys Arg Gly Phe Ala Ser Phe Val Ala Ser Asn Ala Asn
            180                 185                 190

Ala Pro Met Arg Asn Ala Phe Tyr Asp Ala Leu Asn Ser Ile Glu Pro
        195                 200                 205

Val Thr Gly Gly Gly Ser Val Arg Asn Thr Leu Gly Tyr Lys Val Gly
    210                 215                 220

Asn Lys Ser Glu Phe Leu Ser Gln Tyr Lys Phe Asn Leu Cys Phe Glu
225                 230                 235                 240

Asn Ser Gln Gly Tyr Gly Tyr
                245

<210> SEQ ID NO 25
<211> LENGTH: 246
<212> TYPE: PRT
<213> ORGANISM: Helicobacter pylori
<220> FEATURE:
<223> OTHER INFORMATION: Helicobacter pylori strain 1182 FutB
      alpha-1,3/4-fucosyltransferase

<400> SEQUENCE: 25

Met Phe Gln Pro Leu Leu Asp Ala Tyr Ile Glu Ser Ala Ser Ile Glu
1               5                   10                  15

Lys Ile Thr Ser Lys Ser Pro Pro Leu Lys Ile Ala Val Ala Asn
            20                  25                  30

Trp Trp Gly Asp Glu Glu Val Glu Glu Phe Lys Lys Asn Ile Leu Tyr
        35                  40                  45

Phe Ile Leu Ser Gln His Tyr Thr Ile Thr Leu His Gln Asn Pro Asn
    50                  55                  60

Glu Pro Ser Asp Leu Val Phe Gly Ser Pro Ile Gly Ser Ala Arg Lys
65                  70                  75                  80

Ile Leu Ser Tyr Gln Asn Ala Lys Arg Val Phe Tyr Thr Gly Glu Asn
                85                  90                  95

Glu Ser Pro Asn Phe Asn Leu Phe Asp Tyr Ala Ile Gly Phe Asp Glu
            100                 105                 110

Leu Asp Phe Arg Asp Arg Tyr Leu Arg Met Pro Leu Tyr Tyr Asp Arg
        115                 120                 125

Leu His His Lys Ala Glu Ser Val Asn Asp Thr Thr Ser Pro Tyr Lys
    130                 135                 140

Leu Lys Pro Asp Ser Leu Tyr Ala Leu Lys Lys Pro Ser His His Phe
145                 150                 155                 160

Lys Glu Asn His Pro Asn Leu Cys Ala Val Val Asn Asn Glu Ser Asp
                165                 170                 175

Pro Leu Lys Arg Gly Phe Ala Ser Phe Val Ala Ser Asn Pro Asn Ala
            180                 185                 190
```

-continued

```
Pro Lys Arg Asn Ala Phe Tyr Asp Val Leu Asn Ser Ile Glu Pro Val
        195                 200                 205

Ile Gly Gly Gly Ser Val Lys Asn Thr Leu Gly Tyr Asn Ile Lys Asn
    210                 215                 220

Lys Ser Glu Phe Leu Ser Gln Tyr Lys Phe Asn Leu Cys Phe Glu Asn
225                 230                 235                 240

Ser Gln Gly Tyr Gly Tyr
                245

<210> SEQ ID NO 26
<211> LENGTH: 246
<212> TYPE: PRT
<213> ORGANISM: Helicobacter pylori
<220> FEATURE:
<223> OTHER INFORMATION: Helicobacter pylori strain 1218 FutB
      alpha-1,3/4-fucosyltransferase

<400> SEQUENCE: 26

Met Phe Gln Pro Leu Leu Asp Ala Tyr Ile Glu Ser Ala Ser Ile Glu
 1               5                  10                  15

Lys Ile Thr Ser Lys Ser Pro Pro Leu Lys Ile Ala Val Ala Asn
            20                  25                  30

Trp Trp Gly Asp Glu Glu Val Glu Glu Phe Lys Lys Asn Ile Leu Tyr
        35                  40                  45

Phe Ile Leu Ser Gln His Tyr Thr Ile Thr Leu His Gln Asn Pro Asn
    50                  55                  60

Glu Pro Ser Asp Leu Val Phe Gly Ser Pro Ile Gly Ser Ala Arg Lys
65                  70                  75                  80

Ile Leu Ser Tyr Gln Asn Ala Lys Arg Val Phe Tyr Thr Gly Glu Asn
                85                  90                  95

Glu Ser Pro Asn Phe Asn Leu Phe Asp Tyr Ala Ile Gly Phe Asp Glu
            100                 105                 110

Leu Asp Phe Arg Asp Arg Tyr Leu Arg Met Pro Leu Tyr Tyr Asp Arg
        115                 120                 125

Leu His His Lys Ala Glu Ser Val Asn Asp Thr Thr Ser Pro Tyr Lys
    130                 135                 140

Leu Lys Pro Asp Ser Leu Tyr Ala Leu Lys Lys Pro Ser His His Phe
145                 150                 155                 160

Lys Glu Asn His Pro Asn Leu Cys Ala Val Val Asn Asn Glu Ser Asp
                165                 170                 175

Pro Leu Lys Arg Gly Phe Ala Ser Phe Val Ala Ser Asn Pro Asn Ala
            180                 185                 190

Pro Lys Arg Asn Ala Phe Tyr Asp Ala Leu Asn Ser Ile Glu Pro Val
        195                 200                 205

Ile Gly Gly Gly Ser Val Lys Asn Thr Leu Gly Tyr Asn Ile Lys Asn
    210                 215                 220

Lys Ser Glu Phe Leu Ser Gln Tyr Lys Phe Asn Leu Cys Phe Glu Asn
225                 230                 235                 240

Ser Gln Gly Tyr Gly Tyr
                245

<210> SEQ ID NO 27
<211> LENGTH: 247
<212> TYPE: PRT
<213> ORGANISM: Helicobacter pylori
<220> FEATURE:
<223> OTHER INFORMATION: Helicobacter pylori strain 19C2 FutB
```

-continued alpha-1,3/4-fucosyltransferase

<400> SEQUENCE: 27

Met Phe Gln Pro Leu Leu Asp Ala Tyr Ile Asp Ser Thr Arg Leu Asp
1               5                   10                  15

Glu Thr Asp Tyr Lys Pro Pro Leu Asn Ile Ala Leu Ala Asn Trp Trp
            20                  25                  30

Pro Leu Asp Lys Arg Glu Ser Lys Gly Phe Arg Lys Lys Phe Ile Leu
        35                  40                  45

His Phe Ile Leu Ser Gln His Tyr Thr Ile Ala Leu His Arg Asn Pro
    50                  55                  60

Asp Lys Pro Ala Asp Ile Val Phe Gly Asn Pro Leu Gly Ser Ala Arg
65                  70                  75                  80

Lys Ile Leu Ser Tyr Gln Asn Ala Lys Arg Val Phe Tyr Thr Gly Glu
                85                  90                  95

Asn Glu Val Pro Asn Phe Asn Leu Phe Asp Tyr Ala Ile Gly Phe Asp
            100                 105                 110

Glu Leu Asp Phe Arg Asp Arg Tyr Leu Arg Met Pro Leu Tyr Tyr Asp
        115                 120                 125

Arg Leu His His Lys Ala Glu Ser Val Asn Asp Thr Thr Ala Pro Tyr
    130                 135                 140

Lys Ile Lys Ser Asp Ser Leu Tyr Ala Leu Lys Lys Pro Ser His His
145                 150                 155                 160

Phe Lys Glu Asn His Pro His Leu Cys Ala Leu Ile Asn Asn Glu Ile
                165                 170                 175

Asp Pro Leu Lys Arg Gly Phe Ala Ser Phe Val Ala Ser Asn Pro Asn
            180                 185                 190

Ala Pro Ile Arg Asn Ala Phe Tyr Glu Ala Leu Asn Ser Ile Glu Pro
        195                 200                 205

Val Thr Gly Gly Gly Ser Val Arg Asn Thr Leu Gly Tyr Asn Val Lys
    210                 215                 220

Asn Lys Asn Glu Phe Leu Ser Gln Tyr Lys Phe Asn Leu Cys Phe Glu
225                 230                 235                 240

Asn Thr Gln Gly Tyr Gly Tyr
                245

<210> SEQ ID NO 28
<211> LENGTH: 13
<212> TYPE: PRT
<213> ORGANISM: Artificial Sequence
<220> FEATURE:
<223> OTHER INFORMATION: Description of Artificial Sequence:Helicobacter
      pylori alpha-1,3/4-fucosyltransferase consensus
      sequence

<400> SEQUENCE: 28

Met Phe Gln Pro Leu Leu Asp Ala Phe Ile Glu Ser Ala
1               5                   10

<210> SEQ ID NO 29
<211> LENGTH: 16
<212> TYPE: PRT
<213> ORGANISM: Artificial Sequence
<220> FEATURE:
<223> OTHER INFORMATION: Description of Artificial Sequence:Helicobacter
      pylori alpha-1,3/4-fucosyltransferase consensus
      sequence

<400> SEQUENCE: 29

```
Pro Pro Leu Lys Ile Ala Val Ala Asn Trp Trp Gly Asp Glu Glu Ile
1               5                   10                  15
```

<210> SEQ ID NO 30
<211> LENGTH: 15
<212> TYPE: PRT
<213> ORGANISM: Artificial Sequence
<220> FEATURE:
<223> OTHER INFORMATION: Description of Artificial Sequence:Helicobacter
      pylori alpha-1,3/4-fucosyltransferase consensus
      sequence

<400> SEQUENCE: 30

```
Ile Leu Tyr Phe Ile Leu Ser Gln His Tyr Thr Ile Thr Leu His
1               5                   10                  15
```

<210> SEQ ID NO 31
<211> LENGTH: 32
<212> TYPE: PRT
<213> ORGANISM: Artificial Sequence
<220> FEATURE:
<223> OTHER INFORMATION: Description of Artificial Sequence:Helicobacter
      pylori alpha-1,3/4-fucosyltransferase consensus
      sequence

<400> SEQUENCE: 31

```
Pro Ala Asp Ile Val Phe Gly Asn Pro Leu Gly Ser Ala Arg Lys Ile
1               5                   10                  15

Leu Ser Tyr Gln Asn Ala Lys Arg Val Phe Tyr Thr Gly Glu Asn Glu
            20                  25                  30
```

<210> SEQ ID NO 32
<211> LENGTH: 28
<212> TYPE: PRT
<213> ORGANISM: Artificial Sequence
<220> FEATURE:
<223> OTHER INFORMATION: Description of Artificial Sequence:Helicobacter
      pylori alpha-1,3/4-fucosyltransferase consensus
      sequence

<400> SEQUENCE: 32

```
Pro Asn Phe Asn Leu Phe Asp Tyr Ala Ile Gly Phe Asp Glu Leu Asp
1               5                   10                  15

Phe Arg Asp Arg Tyr Leu Arg Met Pro Leu Tyr Tyr
            20                  25
```

<210> SEQ ID NO 33
<211> LENGTH: 6
<212> TYPE: PRT
<213> ORGANISM: Artificial Sequence
<220> FEATURE:
<223> OTHER INFORMATION: Description of Artificial Sequence:Helicobacter
      pylori alpha-1,3/4-fucosyltransferase consensus
      sequence

<400> SEQUENCE: 33

```
Leu His His Lys Ala Glu
1               5
```

<210> SEQ ID NO 34
<211> LENGTH: 11
<212> TYPE: PRT
<213> ORGANISM: Artificial Sequence
<220> FEATURE:
<223> OTHER INFORMATION: Description of Artificial Sequence:Helicobacter
      pylori alpha-1,3/4-fucosyltransferase consensus
      sequence

<400> SEQUENCE: 34

Val Asn Asp Thr Thr Ser Pro Tyr Lys Leu Lys
1               5                   10

<210> SEQ ID NO 35
<211> LENGTH: 46
<212> TYPE: PRT
<213> ORGANISM: Artificial Sequence
<220> FEATURE:
<223> OTHER INFORMATION: Description of Artificial Sequence:Helicobacter
      pylori alpha-1,3/4-fucosyltransferase consensus
      sequence

<400> SEQUENCE: 35

Asp Ser Leu Tyr Ala Leu Lys Lys Pro Ser His His Phe Lys Glu Asn
1               5                   10                  15

His Pro Asn Leu Cys Ala Val Val Asn Asn Glu Ser Asp Pro Leu Lys
            20                  25                  30

Arg Gly Phe Ala Ser Phe Val Ala Ser Asn Pro Asn Ala Pro
        35                  40                  45

<210> SEQ ID NO 36
<211> LENGTH: 14
<212> TYPE: PRT
<213> ORGANISM: Artificial Sequence
<220> FEATURE:
<223> OTHER INFORMATION: Description of Artificial Sequence:Helicobacter
      pylori alpha-1,3/4-fucosyltransferase consensus
      sequence

<400> SEQUENCE: 36

Arg Asn Ala Phe Tyr Asp Ala Leu Asn Ser Ile Glu Pro Val
1               5                   10

<210> SEQ ID NO 37
<211> LENGTH: 37
<212> TYPE: PRT
<213> ORGANISM: Artificial Sequence
<220> FEATURE:
<223> OTHER INFORMATION: Description of Artificial Sequence:Helicobacter
      pylori alpha-1,3/4-fucosyltransferase consensus
      sequence

<400> SEQUENCE: 37

Gly Gly Gly Ser Val Lys Asn Thr Leu Gly Tyr Asn Val Lys Asn Lys
1               5                   10                  15

Ser Glu Phe Leu Ser Gln Tyr Lys Phe Asn Leu Cys Phe Glu Asn Ser
            20                  25                  30

Gln Gly Tyr Gly Tyr
        35

<210> SEQ ID NO 38
<211> LENGTH: 333
<212> TYPE: DNA
<213> ORGANISM: Helicobacter pylori
<220> FEATURE:
<223> OTHER INFORMATION: Helicobacter pylori strain 915 FutA (915A.cod
      (MWG)) alpha-1,3/4-fucosyltransferase

<400> SEQUENCE: 38
atgttccaac ccctattaga tgcctttata gaaagcgctt ccattgaaaa aatggcctct     60
aaatctcccc ccctaaaaat cgctgtggcg aattggtggg gagatgaaga aattaaaaaa    120
tttaaaaaga gcgttcttta ttttatccta agccagcatt acacaatcac tttacaccga    180

-continued

```
aaccctgata aacctgcgga catcgtctttt ggtaaccccc ttggatcagc cagaaaaatc      240
ttatcctatc aaaacgcaaa aagggtgttt tacaccggtg aaaatgaagt ccctaacttc      300
aacctctttg attacgccat aggcttttga tga                                    333
```

<210> SEQ ID NO 39
<211> LENGTH: 53
<212> TYPE: DNA
<213> ORGANISM: Artificial Sequence
<220> FEATURE:
<223> OTHER INFORMATION: Description of Artificial Sequence:Helicobacter
      pylori alpha-1,3/4-fucosyltransferase consensus
      sequence

<400> SEQUENCE: 39

```
atgttccaac ccctattaga cgcctttata gaaagcgctt ccattgaaaa aat              53
```

<210> SEQ ID NO 40
<211> LENGTH: 20
<212> TYPE: DNA
<213> ORGANISM: Artificial Sequence
<220> FEATURE:
<223> OTHER INFORMATION: Description of Artificial Sequence:Helicobacter
      pylori alpha-1,3/4-fucosyltransferase consensus
      sequence

<400> SEQUENCE: 40

```
gcctctaaat ctcccccccc                                                   20
```

<210> SEQ ID NO 41
<211> LENGTH: 26
<212> TYPE: DNA
<213> ORGANISM: Artificial Sequence
<220> FEATURE:
<223> OTHER INFORMATION: Description of Artificial Sequence:Helicobacter
      pylori alpha-1,3/4-fucosyltransferase consensus
      sequence

<400> SEQUENCE: 41

```
taaaaatcgc tgtggcgaat tggtgg                                            26
```

<210> SEQ ID NO 42
<211> LENGTH: 23
<212> TYPE: DNA
<213> ORGANISM: Artificial Sequence
<220> FEATURE:
<223> OTHER INFORMATION: Description of Artificial Sequence:Helicobacter
      pylori alpha-1,3/4-fucosyltransferase consensus
      sequence

<400> SEQUENCE: 42

```
agaaattaaa gaatttaaaa aga                                               23
```

<210> SEQ ID NO 43
<211> LENGTH: 17
<212> TYPE: DNA
<213> ORGANISM: Artificial Sequence
<220> FEATURE:
<223> OTHER INFORMATION: Description of Artificial Sequence:Helicobacter
      pylori alpha-1,3/4-fucosyltransferase consensus
      sequence

<400> SEQUENCE: 43

```
cagcattaca caatcac                                                      17
```

<210> SEQ ID NO 44
<211> LENGTH: 10

```
<212> TYPE: DNA
<213> ORGANISM: Artificial Sequence
<220> FEATURE:
<223> OTHER INFORMATION: Description of Artificial Sequence:Helicobacter
      pylori alpha-1,3/4-fucosyltransferase consensus
      sequence

<400> SEQUENCE: 44
tcgtctttgg                                                              10

<210> SEQ ID NO 45
<211> LENGTH: 44
<212> TYPE: DNA
<213> ORGANISM: Artificial Sequence
<220> FEATURE:
<223> OTHER INFORMATION: Description of Artificial Sequence:Helicobacter
      pylori alpha-1,3/4-fucosyltransferase consensus
      sequence

<400> SEQUENCE: 45
cttggatcag ccagaaaaat cttatcctat caaaacgcaa aaag                        44

<210> SEQ ID NO 46
<211> LENGTH: 24
<212> TYPE: DNA
<213> ORGANISM: Artificial Sequence
<220> FEATURE:
<223> OTHER INFORMATION: Description of Artificial Sequence:Helicobacter
      pylori alpha-1,3/4-fucosyltransferase consensus
      sequence

<400> SEQUENCE: 46
gtgttttaca ccggtgaaaa cgaa                                              24

<210> SEQ ID NO 47
<211> LENGTH: 36
<212> TYPE: DNA
<213> ORGANISM: Artificial Sequence
<220> FEATURE:
<223> OTHER INFORMATION: Description of Artificial Sequence:Helicobacter
      pylori alpha-1,3/4-fucosyltransferase consensus
      sequence

<400> SEQUENCE: 47
cctaatttca acctctttga ttacgccata ggcttt                                 36

<210> SEQ ID NO 48
<211> LENGTH: 11
<212> TYPE: DNA
<213> ORGANISM: Artificial Sequence
<220> FEATURE:
<223> OTHER INFORMATION: Description of Artificial Sequence:Helicobacter
      pylori alpha-1,3/4-fucosyltransferase consensus
      sequence

<400> SEQUENCE: 48
gatgaattgg a                                                            11

<210> SEQ ID NO 49
<211> LENGTH: 17
<212> TYPE: DNA
<213> ORGANISM: Artificial Sequence
<220> FEATURE:
<223> OTHER INFORMATION: Description of Artificial Sequence:Helicobacter
      pylori alpha-1,3/4-fucosyltransferase consensus
      sequence

<400> SEQUENCE: 49
```
tttagagatc gttattt                                                17

<210> SEQ ID NO 50
<211> LENGTH: 11
<212> TYPE: DNA
<213> ORGANISM: Artificial Sequence
<220> FEATURE:
<223> OTHER INFORMATION: Description of Artificial Sequence:Helicobacter
      pylori alpha-1,3/4-fucosyltransferase consensus
      sequence

<400> SEQUENCE: 50
agaatgcctt t                                                      11

<210> SEQ ID NO 51
<211> LENGTH: 11
<212> TYPE: DNA
<213> ORGANISM: Artificial Sequence
<220> FEATURE:
<223> OTHER INFORMATION: Description of Artificial Sequence:Helicobacter
      pylori alpha-1,3/4-fucosyltransferase consensus
      sequence

<400> SEQUENCE: 51
ataaagccga g                                                      11

<210> SEQ ID NO 52
<211> LENGTH: 12
<212> TYPE: DNA
<213> ORGANISM: Artificial Sequence
<220> FEATURE:
<223> OTHER INFORMATION: Description of Artificial Sequence:Helicobacter
      pylori alpha-1,3/4-fucosyltransferase consensus
      sequence

<400> SEQUENCE: 52
aatgacacca ct                                                     12

<210> SEQ ID NO 53
<211> LENGTH: 17
<212> TYPE: DNA
<213> ORGANISM: Artificial Sequence
<220> FEATURE:
<223> OTHER INFORMATION: Description of Artificial Sequence:Helicobacter
      pylori alpha-1,3/4-fucosyltransferase consensus
      sequence

<400> SEQUENCE: 53
cgccttacaa actcaaa                                                17

<210> SEQ ID NO 54
<211> LENGTH: 55
<212> TYPE: DNA
<213> ORGANISM: Artificial Sequence
<220> FEATURE:
<223> OTHER INFORMATION: Description of Artificial Sequence:Helicobacter
      pylori alpha-1,3/4-fucosyltransferase consensus
      sequence

<400> SEQUENCE: 54
ctgacagcct ttatgcttta aaaaaaccct cccatcattt taaagaaaac caccc       55

<210> SEQ ID NO 55
<211> LENGTH: 14
<212> TYPE: DNA
<213> ORGANISM: Artificial Sequence
<220> FEATURE:
<223> OTHER INFORMATION: Description of Artificial Sequence:Helicobacter pylori alpha-1,3/4-fucosyltransferase consensus
sequence

<400> SEQUENCE: 55
tgcgcagtag tgaa                                                    14

<210> SEQ ID NO 56
<211> LENGTH: 35
<212> TYPE: DNA
<213> ORGANISM: Artificial Sequence
<220> FEATURE:
<223> OTHER INFORMATION: Description of Artificial Sequence:Helicobacter
      pylori alpha-1,3/4-fucosyltransferase consensus
      sequence

<400> SEQUENCE: 56
aatgagagcg atcctttgaa aagagggttt gcgag                              35

<210> SEQ ID NO 57
<211> LENGTH: 19
<212> TYPE: DNA
<213> ORGANISM: Artificial Sequence
<220> FEATURE:
<223> OTHER INFORMATION: Description of Artificial Sequence:Helicobacter
      pylori alpha-1,3/4-fucosyltransferase consensus
      sequence

<400> SEQUENCE: 57 agcaaccta acgctccta                                                 19

<210> SEQ ID NO 58
<211> LENGTH: 14
<212> TYPE: DNA
<213> ORGANISM: Artificial Sequence
<220> FEATURE:
<223> OTHER INFORMATION: Description of Artificial Sequence:Helicobacter
      pylori alpha-1,3/4-fucosyltransferase consensus
      sequence

<400> SEQUENCE: 58
gctttaaatt ctat                                                     14

<210> SEQ ID NO 59
<211> LENGTH: 10
<212> TYPE: DNA
<213> ORGANISM: Artificial Sequence
<220> FEATURE:
<223> OTHER INFORMATION: Description of Artificial Sequence:Helicobacter
      pylori alpha-1,3/4-fucosyltransferase consensus
      sequence

<400> SEQUENCE: 59
gagccagtta                                                          10

<210> SEQ ID NO 60
<211> LENGTH: 17
<212> TYPE: DNA
<213> ORGANISM: Artificial Sequence
<220> FEATURE:
<223> OTHER INFORMATION: Description of Artificial Sequence:Helicobacter
      pylori alpha-1,3/4-fucosyltransferase consensus
      sequence

<400> SEQUENCE: 60
tgggggaggg agcgtga                                                  17

<210> SEQ ID NO 61

-continued

```
<211> LENGTH: 18
<212> TYPE: DNA
<213> ORGANISM: Artificial Sequence
<220> FEATURE:
<223> OTHER INFORMATION: Description of Artificial Sequence:Helicobacter
      pylori alpha-1,3/4-fucosyltransferase consensus
      sequence

<400> SEQUENCE: 61
aaacacttta ggctataa                                                 18

<210> SEQ ID NO 62
<211> LENGTH: 23
<212> TYPE: DNA
<213> ORGANISM: Artificial Sequence
<220> FEATURE:
<223> OTHER INFORMATION: Description of Artificial Sequence:Helicobacter
      pylori alpha-1,3/4-fucosyltransferase consensus
      sequence

<400> SEQUENCE: 62
agcgagtttt taagccaata caa                                           23

<210> SEQ ID NO 63
<211> LENGTH: 21
<212> TYPE: DNA
<213> ORGANISM: Artificial Sequence
<220> FEATURE:
<223> OTHER INFORMATION: Description of Artificial Sequence:Helicobacter
      pylori alpha-1,3/4-fucosyltransferase consensus
      sequence

<400> SEQUENCE: 63
ttcaatctgt gttttgaaaa c                                             21

<210> SEQ ID NO 64
<211> LENGTH: 41
<212> TYPE: DNA
<213> ORGANISM: Artificial Sequence
<220> FEATURE:
<223> OTHER INFORMATION: Description of Artificial Sequence:Helicobacter
      pylori alpha-1,3/4-fucosyltransferase consensus
      sequence

<400> SEQUENCE: 64
caaggctatg gctatgtaac tgaaaaaatc attgacgctt a                       41

<210> SEQ ID NO 65
<211> LENGTH: 27
<212> TYPE: DNA
<213> ORGANISM: Artificial Sequence
<220> FEATURE:
<223> OTHER INFORMATION: Description of Artificial Sequence:Helicobacter
      pylori alpha-1,3/4-fucosyltransferase consensus
      sequence

<400> SEQUENCE: 65
agccatacca ttcctattta ttggggg                                       27

<210> SEQ ID NO 66
<211> LENGTH: 16
<212> TYPE: DNA
<213> ORGANISM: Artificial Sequence
<220> FEATURE:
<223> OTHER INFORMATION: Description of Artificial Sequence:Helicobacter
      pylori alpha-1,3/4-fucosyltransferase consensus
      sequence

<400> SEQUENCE: 66
```

```
aagattttaa ccctaa                                                      16

<210> SEQ ID NO 67
<211> LENGTH: 14
<212> TYPE: DNA
<213> ORGANISM: Artificial Sequence
<220> FEATURE:
<223> OTHER INFORMATION: Description of Artificial Sequence:Helicobacter
      pylori alpha-1,3/4-fucosyltransferase consensus
      sequence

<400> SEQUENCE: 67
agttttgtga atgt                                                        14

<210> SEQ ID NO 68
<211> LENGTH: 17
<212> TYPE: DNA
<213> ORGANISM: Artificial Sequence
<220> FEATURE:
<223> OTHER INFORMATION: Description of Artificial Sequence:Helicobacter
      pylori alpha-1,3/4-fucosyltransferase consensus
      sequence

<400> SEQUENCE: 68
tttgatgaag cgattga                                                     17

<210> SEQ ID NO 69
<211> LENGTH: 33
<212> TYPE: DNA
<213> ORGANISM: Artificial Sequence
<220> FEATURE:
<223> OTHER INFORMATION: Description of Artificial Sequence:Helicobacter
      pylori alpha-1,3/4-fucosyltransferase consensus
      sequence

<400> SEQUENCE: 69
tgcacacgca cccaaacgct tatttagaca tgc                                   33

<210> SEQ ID NO 70
<211> LENGTH: 20
<212> TYPE: DNA
<213> ORGANISM: Artificial Sequence
<220> FEATURE:
<223> OTHER INFORMATION: Description of Artificial Sequence:Helicobacter
      pylori alpha-1,3/4-fucosyltransferase consensus
      sequence

<400> SEQUENCE: 70
tatgaaaacc ctttaaacac                                                  20

<210> SEQ ID NO 71
<211> LENGTH: 26
<212> TYPE: DNA
<213> ORGANISM: Artificial Sequence
<220> FEATURE:
<223> OTHER INFORMATION: Description of Artificial Sequence:Helicobacter
      pylori alpha-1,3/4-fucosyltransferase consensus
      sequence

<400> SEQUENCE: 71
ttgatgggaa agcttacttt taccaa                                           26

<210> SEQ ID NO 72
<211> LENGTH: 40
<212> TYPE: DNA
<213> ORGANISM: Artificial Sequence
<220> FEATURE:
```

```
<223> OTHER INFORMATION: Description of Artificial Sequence:Helicobacter
      pylori alpha-1,3/4-fucosyltransferase consensus
      sequence

<400> SEQUENCE: 72
atttgagttt taaaaaaatc ctagattttt ttaaaacgat                           40

<210> SEQ ID NO 73
<211> LENGTH: 11
<212> TYPE: DNA
<213> ORGANISM: Artificial Sequence
<220> FEATURE:
<223> OTHER INFORMATION: Description of Artificial Sequence:Helicobacter
      pylori alpha-1,3/4-fucosyltransferase consensus
      sequence

<400> SEQUENCE: 73
ttagaaaacg a                                                         11

<210> SEQ ID NO 74
<211> LENGTH: 38
<212> TYPE: DNA
<213> ORGANISM: Artificial Sequence
<220> FEATURE:
<223> OTHER INFORMATION: Description of Artificial Sequence:Helicobacter
      pylori alpha-1,3/4-fucosyltransferase consensus
      sequence

<400> SEQUENCE: 74
ttgagggtta attatgatga tttgagggtt aattatga                            38

<210> SEQ ID NO 75
<211> LENGTH: 8
<212> TYPE: PRT
<213> ORGANISM: Artificial Sequence
<220> FEATURE:
<223> OTHER INFORMATION: Description of Artificial Sequence:FLAG tag
      epitope tag

<400> SEQUENCE: 75

Asp Tyr Lys Asp Asp Asp Asp Lys
  1               5

<210> SEQ ID NO 76
<211> LENGTH: 6
<212> TYPE: PRT
<213> ORGANISM: Artificial Sequence
<220> FEATURE:
<223> OTHER INFORMATION: Description of Artificial Sequence:
      hexahistidine affinity tag, purification tag

<400> SEQUENCE: 76

His His His His His His
  1               5
```

SYNTHESIS OF OLIGOSACCHARIDES, GLYCOLIPIDS, AND GLYCOPROTEINS USING BACTERIAL GLYCOSYLTRANSFERASES

CROSS-REFERENCES TO RELATED APPLICATIONS

This application is a continuation of International Application No. PCT/US/2003/023155, filed Jul. 23, 2003 and a continuation of International Application No. PCT/US/2003/023057, filed Jul. 23, 2003; both of which claim the benefit of U.S. Provisional Application No. 60/398,156, filed Jul. 23, 2002, and U.S. Provisional Application 60/424,894, filed Nov. 8, 2002; and all four applications are herein incorporated by reference for all purposes.

FIELD OF INVENTION

This invention provides nucleic acid and amino acid sequences of fucosyltransferases from *Helicobactor pylori*. The invention also provides methods to use the fucosyltransferases to synthesize oligosaccharides, glycoproteins, and glycolipids.

BACKGROUND OF THE INVENTION

Although in recent years significant advances have been made in carbohydrate chemistry, there are still substantial difficulties associated with the chemical synthesis of glycoconjugates, particularly with the formation of the ubiquitous β-1,2-cis-mannoside linkage found in mammalian oligosaccharides. Moreover, regio- and stereo-chemical obstacles must be resolved at each step of the de novo synthesis of a carbohydrate.

In view of the difficulties associated with the chemical synthesis of glycoconjugates, the use of glycosyltransferases to enzymatically synthesize glycoproteins and glycolipids, having desired oligosaccharide moieties, is a promising approach to preparing such glycoconjugates. Enzyme-based syntheses have the advantages of regioselectivity and stereoselectivity, and can be performed using unprotected substrates. Moreover, glycosyltransferases have been used to enzymatically modify oligosaccharide moieties and have been shown to be very effective for producing specific products with good stereochemical and regiochemical control. The glycosyltransferases of interest include fucosyltransferases, sialyltransferases, galactosyltransferases, and N-acetylglucosaminyltransferases. For a general review, see, Crout et al., *Curr. Opin. Chem. Biol.* 2: 98-111 (1998) and Arsequell, et al., *Tetrahedon: Assymetry* 10: 2839 (1997).

Many glycoproteins and glycolipids require the presence of a particular glycoform, or the absence of a particular glycoform, in order to exhibit a particular biological activity. For example, many glycoprotein and glycolipids require the presence of particular fucosylated structures in order to exhibit biological activity. Intercellular recognition mechanisms often require a fucosylated oligosaccharide. For example, a number of glycoproteins that function as cell adhesion molecules, including P-selectin, L-selectin, and E-selectin, bind specific cell surface fucosylated carbohydrate structures such as the sialyl Lewis-x and the sialyl Lewis-a structures. In addition, the specific carbohydrate structures that form the ABO blood group system are fucosylated. The carbohydrate structures in each of the three groups share a Fucα1,2Galβ1-disaccharide unit. In blood group O structures, this disaccharide is the terminal structure; whereas the blood group A structure is formed by an α1,3 GalNAc transferase that adds a terminal GalNAc residue to the disaccharide; and the blood group B structure is formed by an α1,3 galactosyltransferase that adds a terminal galactose residue.

The Lewis blood group structures are also fucosylated. For example the Lewis-x and Lewis-a structures are Galα1,4 (Fucα1,3)GlcNac and Galβ1,3(Fucα1,4)GlcNac, respectively. Both these structures can be further sialylated (NeuAcα2,3-) to form the corresponding sialylated structures. Other Lewis blood group structures of interest are the Lewis-y and Lewis-b structures which are Fucα1,2Galβ1,4 (Fucα1,3)GlcNAcβ-OR and Fucα1,2Galβ1,3(Fucα1,4) GlcNAc-OR, respectively. For a description of the structures of the ABO and Lewis blood group structures and the enzymes involved in their synthesis see, *Essentials of Glycobiology*, Varki et al. eds., Chapter 16 (Cold Spring Harbor Press, Cold Spring Harbor, N.Y., 1999).

Specifically, fucosyltransferases have been used in synthetic pathways to transfer a fucose residue from guanosine-5'-diphosphofucose to a specific hydroxyl of a saccharide acceptor. A variety of donor substrates and acceptor substrates are known (see Guo et al., *Applied Biochem. and Biotech.* 68: 1-20 (1997)). For example, Ichikawa prepared sialyl Lewis-x by a method that involves the fucosylation of sialylated lactosamine with a cloned fucosyltransferase (Ichikawa et al., *J. Am. Chem. Soc.* 114: 9283-9298 (1992)). Lowe has described a method for expressing non-native fucosylation activity in cells, thereby producing fucosylated glycoproteins on cell surfaces, etc. (U.S. Pat. No. 5,955,347).

Thus, since the biological activity of many commercially important recombinantly and transgenically produced glycoproteins and glycolipids depends upon the presence of a particular glycoform, or the absence of a particular glycoform, a need exists for an efficient method for enzymatically synthesizing glycoconjugates having the desired fucoylated oligosaccharide moieties. In addition, there is a need for the efficient production of focosylated oligosaccharides. The present invention fulfills these and other needs.

BRIEF SUMMARY OF THE INVENTION

The present invention provides α1,3/4-fucosyltranferase proteins and nucleic acids from *H. pylori*. The α-1,3/4-fucosyltranferase proteins catalyzes the transfer of a fucose residue from a donor substrate to an acceptor substrate. In one embodiment, the invention provides α-1,3/4-fucosyltranferase nucleic acids with greater than 90% identity to a nucleotide sequence selected from SEQ ID NO: 1, 3, or 7 and that encode α-1,3/4-fucosyltranferase proteins that transfer fucose to GlcNAc residues. In another embodiment, the invention provides α-1,3/4-fucosyltranferase nucleic acids with greater than 90% identity to SEQ ID NO:5 and that encode α-1,3/4-fucosyltranferase proteins that transfer fucose to Glucose residues.

In another embodiment the α-1,3/4-fucosyltranferase nucleic acid is selected from SEQ ID NO:1, 3, 5 or 7. The invention also provides nucleic acid sequences that encode α-1,3/4-fucosyltranferase proteins, including SEQ ID NO:2, 4, 6, or 8 and that catalyze the transfer of fucose to an N-acetylglucosamine residue or to a glucose residue. In one aspect the encoded α-1,3/4-fucosyltransferase also includes an amino acid tag.

In a further aspect the invention provides an isolated nucleic acid that includes SEQ ID NO: 11, and that encodes an α-1,3/4-fucosyltransferase protein that catalyzes the transfer of a fucose residue from a donor substrate to a glucose residue. In another aspect the invention provides a nucleic acid that encodes SEQ ID NO: 12.

In another embodiment the invention provides expression vectors that include the above described α-1,3/4-fucosyltranferase nucleic acids, host cells that include the expression vectors, and methods to produce the α-1,3/4-fucosyltranferase proteins using the host cells cultured under conditions suitable for expression of the α-1,3/4-fucosyltransferase protein.

In another embodiment the invention provides recombinant fucosyltransferase proteins that include amino acid sequence having greater than 90% identity to SEQ ID NO:2, 4, or 8, wherein the fucosyltransferase catalyzes the transfer of a fucose residue from a donor substrate to N-acetylglucosamine. In another embodiment the invention provides recombinant fucosyltransferase proteins that include amino acid sequence having greater than 90% identity to SEQ ID NO:6, wherein the fucosyltransferase catalyzes the transfer of a fucose residue from a donor substrate to glucose. In one aspect, the fucosyltransferase proteins comprise SEQ ID NO:2, 4, 6, or 8. In another aspect the fucosyltranferase proteins also include an amino acid tag.

In another embodiment the invention provides recombinant fucosyltransferase proteins that include SEQ ID NO: 12, and that catalyzes the transfer of a fucose residue from a donor substrate to glucose. In another aspect the fucosyltransferase proteins also include an amino acid tag.

The present invention also provides methods to use the above α-1,3/4-fucosyltransferase protein to produce fucosylated oligosaccharides. The fucosylated oligosaccharides can be further purified. The acceptor substrate can be either N-acetylglucosamine or glucose depending on the needs of the user. In one embodiment the acceptor substrate is Lacto-N-neo-Tetraose (LNnT) and the fucosyltated product is Lacto-N-Fucopentaose III (LNFP III). The α-1,3/4-fucosyltransferase can be used in combination with other glycosyltransferases to produce a fucosylated oligosaccharide. For example, using lactose as a starting material, LNFP can by produced through the action of an α-1,3/4-fucosyltransferase that transfers fucose to N-acetylglucosamine, a β-1,3-N-acetylglucosaminyltransferase, and a β-1,4-galactosyltransferase. The β-1,3-N-acetylglucosaminyltransferase and the β-1,4-galactosyltransferase can be bacterial enzymes and in a preferred embodiment are from *Neisseria gonococcus*.

In another embodiment, the α-1,3/4-fucosyltransferase protein of the present invention are used to produce fucosylated glycolipids. The acceptor substrate can be either N-acetylglucosamine or glucose depending on the needs of the user.

In another embodiment, the present invention provides a method for producing a fucosylated glycoprotein, by combining an α-1,3/4-fucosyltransferase described herein with a glycoprotein that includes an appropriate acceptor substrate under conditions suitable to produce a fucosylated glycoprotein. The acceptor substrate can be selected from Galβ1-OR, Galβ,3/4GlcNAc-OR, NeuAcα2,3Galβ1,3/4GlcNAc-Or, wherein R is an amino acid, a saccharide, an oligosaccharide, or an aglycon group having at least one carbon atom. The accepter substrate can be an N-acetylglucosamine residue or a glucose residue. The α-1,3/4-fucosyltransferase can also include an amino acid tag.

BRIEF DESCRIPTION OF THE DRAWINGS

FIG. 1 provides the nucleic acid (SEQ ID NO:1) and amino acid (SEQ ID NO:2) sequences of fucosyltranferase from *H. pylori* strain 1182B.

FIG. 2 provides the nucleic acid (SEQ ID NO:3) and amino acid (SEQ ID NO:4) sequences of fucosyltranferase from *H. pylori* strain 1111A.

FIG. 3 provides the nucleic acid (SEQ ID NO:5) and amino acid (SEQ ID NO:6) sequences of fucosyltranferase from *H. pylori* strain 1218B.

FIG. 4 provides the nucleic acid (SEQ ID NO:7) and amino acid (SEQ ID NO:8) sequences of fucosyltranferase from *H. pylori* strain 19C2B.

FIG. 5 provides the nucleic acid (SEQ ID NO:9) and amino acid (SEQ ID NO:10) sequences of fucosyltranferase from *H. pylori* strain 915A.

FIG. 6 provides the nucleic acid (SEQ ID NO: 11) and amino acid (SEQ ID NO: 12) sequences of fucosyltranferase from *H. pylori* strain 26695A.

FIG. 7 provides the nucleic acid (SEQ ID NO: 13) and amino acid (SEQ ID NO: 14) sequences of fucosyltranferase from *H. pylori* strain 19C2A.

FIG. 8 provides an alignment between 1182 futB amino acid sequence (SEQ ID NO: 15) and a consensus sequence from the glycosyltransferase family 10 (SEQ ID NO: 16), i.e., the fucosyltransferase family. Amino acids 23 through 305 of 1182 futB are shown in the top line and represent the most conserved region of the protein, i.e. the fucosyltransferase catalytic domain.

FIG. 9 provides an alignment between 1111 futA amino acid sequence (SEQ ID NO: 17) and a consensus sequence from the glycosyltransferase family 10 (SEQ ID NO: 18), i.e., the fucosyltransferase family. Amino acids 27 through 417 of 1182 futB are shown in the top line and represent the most conserved region of the protein, i.e. the fucosyltransferase catalytic domain.

FIG. 10 provides an alignment between 1218 futB amino acid sequence (SEQ ID NO:19) and a consensus sequence from the glycosyltransferase family 10 (SEQ ID NO:20), i.e., the fucosyltransferase family. Amino acids 23 through 399 of 1182 futB are shown in the top line and represent the most conserved region of the protein, i.e. the fucosyltransferase catalytic domain.

FIG. 11 provides an alignment between 19C2 futB amino acid sequence (SEQ ID NO:21) and a consensus sequence from the glycosyltransferase family 10 (SEQ ID NO:22), i.e., the fucosyltransferase family. Amino acids 23 through 377 of 1182 futB are shown in the top line and represent the most conserved region of the disclosed protein, i.e. the fucosyltransferase catalytic domain.

FIG. 12 provides an alignment between amino acid sequence of *H. pylori* strains 1182 FutB (SEQ ID NO:25), 1111 FutA (SEQ ID NO:23), 1218 FutB (SEQ ID NO:26), 19C2 FutB (SEQ ID NO:27), 915FutA (SEQ ID NO:10), 19C2 FutA (SEQ ID NO:14), and 26695 FutA (SEQ ID NO:24). The bottom sequence is a consensus sequence (SEQ ID NOS:28-37).

FIG. 13 provides an alignment between nucleic acid sequence of *H. pylori* strains 1182 FutB (SEQ ID NO:1), 1111 FutA (SEQ ID NO:3), 1218 FutB (SEQ ID NO:5), 19C2 FutB (SEQ ID NO:7), 915FutA (SEQ ID NO:38), 19C2 FutA (SEQ ID NO:13), and 26695 FutA (SEQ ID NO: 11). The bottom sequence is a consensus sequence (SEQ ID NOS:39-74).

FIG. 14 provides oligosaccharide structures of Lacto-N-neo-Tetraose (LNnT), a substrate of the *H. pylori* fucosyltransferases and Lacto-N-Fucopentaose III (LNFPIII or LNFIII), a product of the *H. pylori* fucosyltransferases.

FIG. 15 provides the results of analysis of acceptor specificity for the *H. pylori* fucosyltransferases.

FIG. 16 provides the yield of LNFIII synthesis using the *H. pylori* fucosyltransferases. Two ion exchange resins were tested: MR3 NH$_4$HCO$_3$ and Dowex1/Dowex50 resin.

FIG. 17 demonstrates the use of FutB α-1,3/4-fucosyltransferase from *H. pylori* strain 1182 to transfer fucose to the glycoprotein asialyltranferrin. The upper panel shows GC/MS analysis of sialylated transferrin. The lower panel shows GC/MS analysis of sialylated transferrin that has been enzymatically asialylated and then fucosylated using *H. pylori* strain 1182 FutB α-1,3/4-fucosyltranferase. Key to sugar structures: filled squares-GlcNAc; open circles-mannose; filled diamonds-galactose; triangles-fucose; stars-sialic acid.

DEFINITIONS

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry and nucleic acid chemistry and hybridization described below are those well known and commonly employed in the art. Standard techniques are used for nucleic acid and peptide synthesis. Generally, enzymatic reactions and purification steps are performed according to the manufacturer's specifications. The techniques and procedures are generally performed according to conventional methods in the art and various general references (see generally, Sambrook et al. MOLECULAR CLONING: A LABORATORY MANUAL, 2d ed. (1989) Cold Spring Harbor Laboratory Press, Cold Spring Harbor, N.Y., which is incorporated herein by reference), which are provided throughout this document. The nomenclature used herein and the laboratory procedures in analytical chemistry, and organic synthetic described below are those well known and commonly employed in the art. Standard techniques, or modifications thereof, are used for chemical syntheses and chemical analyses.

The terms "α-1,3/4-fucosyltranferase or fucosyltransferase" or a nucleic acid encoding an "α-1,3/4-fucosyltranferase or fucosyltransferase" refer to nucleic acid and polypeptide polymorphic variants, alleles, mutants, and interspecies homologs that: (1) have an amino acid sequence that has greater than about 60% amino acid sequence identity, 65%, 70%, 75%, 80%, 85%, 90%, preferably 91%, 92%, 93%, 94%, 95%, 96%, 97%, 98% or 99% or greater amino acid sequence identity, preferably over a region of at least about 25, 50, 100, 200, 500, 1000, or more amino acids, to a polypeptide encoded by a nucleic acid selected from SEQ ID NO:1, SEQ ID NO:3, SEQ ID NO:5, SEQ ID NO:7, SEQ ID NO:9, or SEQ ID NO: 13; or an amino acid sequence of SEQ ID NO:2, SEQ ID NO:4, SEQ ID NO:6, SEQ ID NO:8, SEQ ID NO: 10, or SEQ ID NO: 14; (2) specifically bind to antibodies, e.g., polyclonal antibodies, raised against an immunogen comprising an amino acid sequence of SEQ ID NO:2, SEQ ID NO:4, SEQ ID NO:6, SEQ ID NO:8, SEQ ID NO:10, or SEQ ID NO:14; immunogenic fragments thereof, and conservatively modified variants thereof; (3) specifically hybridize under stringent hybridization conditions to a nucleic acid encoding SEQ ID NO:2;, SEQ ID NO:4, SEQ ID NO:6, SEQ ID NO:8, SEQ ID NO: 10, or SEQ ID NO:14; e.g., a nucleic acid sequence of SEQ ID NO:1, SEQ ID NO:3, SEQ ID NO:5, SEQ ID NO:7, SEQ ID NO:9, or SEQ ID NO: 13; or its complement, and conservatively modified variants thereof; (4) have a nucleic acid sequence that has greater than about 90%, preferably greater than about 91%, 92%, 93%, 94%, 95%, 96%, 97%, 98%, 99%, or higher nucleotide sequence identity, preferably over a region of at least about 25, 50, 100, 200, 500, 1000, or more nucleotides, to SEQ ID NO:1, SEQ ID NO:3, SEQ ID NO:5, SEQ ID NO:7, SEQ ID NO:9, or SEQ ID NO: 13; or its complement. The nucleic acids and proteins of the invention include both naturally occurring or recombinant molecules.

The α-1,3/4-fucosyltranferase enzymes of the invention can also be recognized by the presence of highly conserved catalytic domains that are found in a family of fucosyltransferase proteins, glycosyltransferase family 10, see e.g., gnl|CDD|16836 pfam00852, Glyco_transf_10. Alignments between conserved catalytic domains of 1182 futB, 1111 futA, 1218 futB, and 19C2 futB and a consensus sequence from the catalytic domain of glycosyltransferase family 10 members are shown in FIGS. 8-11.

A biologically active fucosyltransferase as described herein is a fucosyltransferase that catalyzes the transfer of fucose from a donor substrate, for example, GDP-fucose, to an acceptor molecule in an α-1,3/4-linkage. The acceptor molecule can be either N-acetylglucosylamine (GlucNAc) or glucose. For example, Fucosyltransferases from the following *H. pylori* strains transfer fucose to Glc-NAc: Strain 915 FutA, Strain 1111 FutA, Strain 19C2 FutB, and Strain 1182 FutB. The FutA gene product from *H. pylori* Strain 19C2 FutA transfers fucose to the reducing glucose of the LNnT acceptor, as did the FutB gene product from *H. pylori* strain 1218, and a novel 26695 FutA protein. In preferred embodiments, the fucosyltransferase transfers fuscose exclusively to GlcNAc or exclusively to glucose. The acceptor molecule can be a carbohydrate, an oligosaccharide, a glycolipid, or a glycoprotein.

The *H. pylori* fucosyltransferase proteins of the invention are useful for transferring a saccharide from a donor substrate to an acceptor substrate. The addition generally takes place at the non-reducing end of an oligosaccharide or carbohydrate moiety on a biomolecule. However, in some embodiments the fucose residue is added to a reducing glucose residue. Biomolecules as defined here include but are not limited to biologically significant molecules such as carbohydrates, oligosaccchrides, proteins (e.g., glycoproteins), and lipids (e.g., glycolipids, phospholipids, sphingolipids and gangliosides).

The following abbreviations are used herein:
Ara=arabinosyl;
Fru=fructosyl;
Fuc=fucosyl;
Gal=galactosyl;
GalNAc=N-acetylgalactosylamino;
Glc=glucosyl;
GlcNAc=N-acetylglucosylamino;
Man=mannosyl; and
NeuAc=sialyl (N-acetylneuraminyl)
FT or Fut=fucosyltransferase*
ST=sialyltransferase*
GalT=galactosyltransferase*

Oligosaccharides are considered to have a reducing end and a non-reducing end, whether or not the saccharide at the reducing end is in fact a reducing sugar. In accordance with accepted nomenclature, oligosaccharides are depicted herein with the non-reducing end on the left and the reducing end on the right.

All oligosaccharides described herein are described with the name or abbreviation for the non-reducing saccharide (e.g., Gal), followed by the configuration of the glycosidic bond (α or β), the ring bond, the ring position of the reducing saccharide involved in the bond, and then the name or abbreviation of the reducing saccharide (e.g., GlcNAc). The linkage between two sugars may be expressed, for example, as 2,3, 2→3, or (2,3). Each saccharide is a pyranose or furanose.

The term "sialic acid" refers to any member of a family of nine-carbon carboxylated sugars. The most common member of the sialic acid family is N-acetyl-neuraminic acid (2-keto-5-acetamido-3,5-dideoxy-D-glycero-D-galactononulopyranos-1-onic acid (often abbreviated as Neu5Ac, NeuAc, or NANA). A second member of the family is N-glycolyl-neuraminic acid (Neu5Gc or NeuGc), in which the N-acetyl group of NeuAc is hydroxylated. A third sialic acid family member is 2-keto-3-deoxy-nonulosonic acid (KDN) (Nadano et al. (1986) *J. Biol. Chem.* 261: 11550-11557; Kanamori et al., *J. Biol. Chem.* 265: 21811-21819 (1990)). Also included are 9-substituted sialic acids such as a 9-O—$C_1$-$C_6$ acyl-Neu5Ac like 9-O-lactyl-Neu5Ac or 9-O-acetyl-Neu5Ac, 9-deoxy-9-fluoro-Neu5Ac and 9-azido-9-deoxy-Neu5Ac. For review of the sialic acid family, see, e.g., Varki, *Glycobiology* 2: 25-40 (1992); *Sialic Acids: Chemistry, Metabolism and Function*, R. Schauer, Ed. (Springer-Verlag, New York (1992)). The synthesis and use of sialic acid compounds in a sialylation procedure is disclosed in international application WO 92/16640, published Oct. 1, 1992.

An "acceptor substrate" for a glycosyltransferase is an oligosaccharide moiety that can act as an acceptor for a particular glycosyltransferase. When the acceptor substrate is contacted with the corresponding glycosyltransferase and sugar donor substrate, and other necessary reaction mixture components, and the reaction mixture is incubated for a sufficient period of time, the glycosyltransferase transfers sugar residues from the sugar donor substrate to the acceptor substrate. The acceptor substrate will often vary for different types of a particular glycosyltransferase.

An "acceptor substrate" for an *H. pylori* fucosyltransferase is an oligosaccharide moiety that can act as an acceptor for a the *H. pylori* fucosyltransferase. When the acceptor substrate is contacted with the *H. pylori* fucosyltransferase and sugar donor substrate (e.g., GDP-fucose), and other necessary reaction mixture components, and the reaction mixture is incubated for a sufficient period of time, the *H. pylori* fucosyltransferase transfers fucose residues from the GDP-fucose to the acceptor substrate. The acceptor substrate will often vary for different types of a particular fucosyltransferases. For example, the acceptor substrate for a mammalian galactoside 2-L-fucosyltransferase (α,1,2-fucosyltransferase) will include a Galβ1,4-GlcNAc-R at a non-reducing terminus of an oligosaccharide; this fucosyltransferase attaches a fucose residue to the Gal via an α1,2 linkage. Terminal Galβ1,4-GlcNAc-R and Galβ1,3-GlcNAc-R and sialylated analogs thereof are acceptor substrates for α1,3 and α1,4-fucosyltransferases, respectively. These enzymes, however, attach the fucose residue to the GlcNAc residue of the acceptor substrate. Accordingly, the term "acceptor substrate" is taken in context with the particular glycosyltransferase of interest for a particular application. The *H. pylori* fucosyltransferase described herein will transfer fucose to sialylated or unsialylated acceptor substrates. Some *H. pylori* fucosyltransferase described herein will transfer fucose to glucose residues.

A "donor substrate" for glycosyltransferases is an activated nucleotide sugar. Such activated sugars generally consist of uridine, guanosine, and cytidine monophosphate derivatives of the sugars (UMP, GMP and CMP, respectively) or diphosphate derivatives of the sugars (UDP, GDP and CDP, respectively) in which the nucleoside monophosphate or diphosphate serves as a leaving group. For example, a donor substrate for fucosyltransferases is GDP-fucose. Donor substrates for sialyltransferases, for example, are activated sugar nucleotides comprising the desired sialic acid. For instance, in the case of NeuAc, the activated sugar is CMP-NeuAc.

A "substantially uniform glycoform" or a "substantially uniform glycosylation pattern," when referring to a glycoprotein species, refers to the percentage of acceptor substrates that are glycosylated by the glycosyltransferase of interest (e.g., fucosyltransferase). For example, in the case of the α1,3 or α1,4 fucosyltransferase noted above, a substantially uniform fucosylation pattern exists if substantially all (as defined below) of the Galβ1,4-GlcNAc-R and sialylated or unsialylated analogues thereof are fucosylated in a composition comprising the glycoprotein of interest. It will be understood by one of skill in the art, that the starting material may contain glycosylated acceptor substrates (e.g., fucosylated Galβ1,4-GlcNAc-R substrates). Thus, the calculated amount of glycosylation will include acceptor substrates that are glycosylated by the methods of the invention, as well as those acceptor substrates already glycosylated in the starting material.

The term "substantially" in the above definitions of "substantially uniform" generally means at least about 60%, at least about 70%, at least about 80%, or more preferably at least about 90%, 91%, 92%, 93%, 94%, 95%, 96%, 97%, 98%, 99%, or 100% of the acceptor substrates for a particular glycosyltransferase are glycosylated (e.g., fucosylated Galβ1,4-GlcNAc-R substrates).

The term "substantially identical fucosylation pattern," refers to a glycosylation pattern of a glycoprotein produced by a method of the invention which is at least about 80%, more preferably at least about 90%, even more preferably at least about 91%, 92%, 93%, 94%, or 95% and still more preferably at least about 96%, 97%, 98% or 99% identical to the fucosylation of a known glycoprotein. "Known fucosylation pattern," refers to a fucosylation pattern of a known glycoprotein from any source having any known level of fucosylation.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

"Protein", "polypeptide", or "peptide" refer to a polymer in which the monomers are amino acids and are joined together through amide bonds, alternatively referred to as a polypeptide. When the amino acids are a-amino acids, either the L-optical isomer or the D-optical isomer can be used. Additionally, unnatural amino acids, for example, β-alanine, phenylglycine and homoarginine are also included. Amino acids that are not gene-encoded may also be used in the present invention. Furthermore, amino acids that have been modified to include reactive groups may also be used in the invention. All of the amino acids used in the present invention may be either the D- or L-isomer. The L-isomers are generally preferred. In addition, other peptidomimetics are also useful in the present invention. For a general review, see, Spatola, A. F., in CHEMISTRY AND BIOCHEMISTRY OF AMINO ACIDS, PEPTIDES AND PROTEINS, B. Weinstein, eds., Marcel Dekker, New York, p. 267 (1983).

The term "recombinant" when used with reference to a cell indicates that the cell replicates a heterologous nucleic acid, or expresses a peptide or protein encoded by a heterologous nucleic acid. Recombinant cells can contain genes that are not found within the native (non-recombinant) form of the cell. Recombinant cells can also contain genes found in the native form of the cell wherein the genes are modified and re-introduced into the cell by artificial means. The term also encompasses cells that contain a nucleic acid endogenous to the cell that has been modified without removing the nucleic acid from the cell; such modifications include those obtained by gene replacement, site-specific mutation, and related techniques. A "recombinant protein" is one which has been produced by a recombinant cell.

A "fusion protein" refers to an *H. pylori* fucosyltransferase protein comprising amino acid sequences that are in addition to, in place of, less than, and/or different from the amino acid sequences encoding the original or native full-length protein or subsequences thereof.

Components of fusion proteins include "accessory enzymes" and/or "purification or amino acid tags." An "accessory enzyme" as referred to herein, is an enzyme that is involved in catalyzing a reaction that, for example, forms a substrate for a fucosyltransferase. An accessory enzyme can, for example, catalyze the formation of a nucleotide sugar that is used as a donor moiety by a fucosyltransferase, e.g., GDP-fucose. An accessory enzyme can also be one that is used in the generation of a nucleotide triphosphate required for formation of a nucleotide sugar, or in the generation of the sugar which is incorporated into the nucleotide sugar, e.g., fucose. The recombinant fusion protein of the invention can be constructed and expressed as a fusion protein with a molecular "purification tag" at one end, which facilitates purification of the protein. Such tags can also be used for immobilization of a protein of interest during the glycosylation reaction. Suitable tags include "epitope tags," which are a protein sequence that is specifically recognized by an antibody. Epitope tags are generally incorporated into fusion proteins to enable the use of a readily available antibody to unambiguously detect or isolate the fusion protein. A "FLAG tag" is a commonly used epitope tag, specifically recognized by a monoclonal anti-FLAG antibody, consisting of the sequence Asp-TyrLysAspAspAsp AspLys (SEQ ID NO:75) or a substantially identical variant thereof. Other suitable tags are known to those of skill in the art, and include, for example, an affinity tag such as a hexahistidine (SEQ ID NO:76) peptide, which will bind to metal ions such as nickel or cobalt ions. Purification tags also include maltose binding domains and starch binding domains. Purification of maltose binding domain proteins is know to those of skill in the art. Starch binding domains are described in WO 99/15636, herein incorporated by reference. Affinity purification of a fusion protein comprising a starch binding domain using a betacylodextrin (BCD)-derivatized resin is described in U.S. Ser. No. 60/468, 374, filed May 5, 2003, herein incorporated by reference in its entirety.

The term "functional domain" with reference to glycosyltransferases, refers to a domain of the glycosyltransferase that confers or modulates an activity of the enzyme, e.g., acceptor substrate specificity, catalytic activity, binding affinity, or other biological or biochemical activity. Examples of functional domains of glycosyltransferases include, but are not limited to, the catalytic domain.

The terms "expression level" or "level of expression" with reference to a protein refers to the amount of a protein produced by a cell. The amount of protein produced by a cell can be measured by the assays and activity units described herein or known to one skilled in the art. One skilled in the art would know how to measure and describe the amount of protein produced by a cell using a variety of assays and units, respectively. Thus, the quantitation and quantitative description of the level of expression of a protein, e.g., an *H. pylori* fucosyltransferase, can be assayed measuring the enzymatic activity or the units used to describe the activity, or the amount of protein. The amount of protein produced by a cell can be determined by standard known assays, for example, the protein assay by Bradford (1976), the bicinchoninic acid protein assay kit from Pierce (Rockford, Ill.), or as described in U.S. Pat. No. 5,641,668.

The term "enzymatic activity" refers to an activity of an enzyme and may be measured by the assays and units described herein or known to one skilled in the art.

The term "specific activity" as used herein refers to the catalytic activity of an enzyme, e.g., an *H. pylori* fucosyltransferase protein of the present invention, and may be expressed in activity units. As used herein, one activity unit catalyzes the formation of 1 μmol of product per minute at a given temperature (e.g., at 37° C.) and pH value (e.g., at pH 7.5). Thus, 10 units of an enzyme is a catalytic amount of that enzyme where 10 μmol of substrate are converted to 10 μmol of product in one minute at a temperature of, e.g., 37° C. and a pH value of, e.g., 7.5.

A "catalytic domain" refers to a protein domain, or a subsequence thereof, that catalyzes an enzymatic reaction performed by the enzyme. For example, a catalytic domain of a fucosyltransferase will include a subsequence of the fucosyltransferase sufficient to transfer a fucose residue from a donor to an acceptor saccharide. A catalytic domain can include an entire enzyme, a subsequence thereof, or can include additional amino acid sequences that are not attached to the enzyme, or a subsequence thereof, as found in nature. The α-1,3/4-fucosyltranferase enzymes of the invention can also be recognized by the presence of highly conserved catalytic domains that are found in a family of fucosyltransferase proteins, glycosyltransferase family 10, see e.g., gnl|CDD|16836 pfam00852, Glyco_transf_10. Alignments between conserved catalytic domains of 1182 futB, 1111 futA, 1218 futB, and 19C2 futB and a consensus sequence from the catalytic domain of glycosyltransferase family 10 members are shown in FIGS. 8-11. Alignments between conserved catalytic domains of 1182 futB, 1111 futA, 1218 futB, and 19C2 futB and a consensus sequence from the catalytic domain of glycosyltransferase family 10 members are shown in FIGS. 8-11. Highly conserved regions, similar to a region of the glycosyltransferase family 10 catalytic domain consensus sequence starting at about amino acid 11 and ending at amino acid 301, are found in each of the *H. pylori* α-1,3/4-fucosyltranferase enzymes listed above, e.g., 1182 futB, amino acids 23-305; 1111 futA, amino acids 27-304; 1218 futB, amino acids 23-305; and 19C2 futB amino acids 22-277, and are believed to be the catalytic domains of the enzyme. Thus, polypeptides comprising the above-identified fucosyltransferase catalytic domains can be used in the methods of the invention, e.g., fucosylating glycoproteins. Nucleic acids that encode the above-identified fucosyltransferase catalytic domains can also be used in the methods of the invention, e.g., production of fucosyltransferase proteins for fucosylating glycoproteins.

A "subsequence" refers to a sequence of nucleic acids or amino acids that comprise a part of a longer sequence of nucleic acids or amino acids (e.g., protein) respectively.

The term "nucleic acid" refers to a deoxyribonucleotide or ribonucleotide polymer in either single-or double-stranded form, and unless otherwise limited, encompasses known analogues of natural nucleotides that hybridize to nucleic acids in a manner similar to naturally occurring nucleotides. Unless otherwise indicated, a particular nucleic acid sequence includes the complementary sequence thereof.

A "recombinant expression cassette" or simply an "expression cassette" is a nucleic acid construct, generated recombinantly or synthetically, with nucleic acid elements that are capable of affecting expression of a structural gene in hosts compatible with such sequences. Expression cassettes include at least promoters and optionally, transcription termination signals. Typically, the recombinant expression cassette includes a nucleic acid to be transcribed (e.g., a nucleic acid encoding a desired polypeptide), and a promoter. Additional factors necessary or helpful in effecting expression may also be used as described herein. For example, an expression cassette can also include nucleotide sequences that encode a signal sequence that directs secretion of an expressed protein from the host cell. Transcription termination signals, enhancers, and other nucleic acid sequences that influence gene expression, can also be included in an expression cassette.

A "heterologous sequence" or a "heterologous nucleic acid", as used herein, is one that originates from a source foreign to the particular host cell, or, if from the same source, is modified from its original form. Thus, a heterologous glycoprotein gene in a eukaryotic host cell includes a glycoprotein-encoding gene that is endogenous to the particular host cell that has been modified. Modification of the heterologous sequence may occur, e.g., by treating the DNA with a restriction enzyme to generate a DNA fragment that is capable of being operably linked to the promoter. Techniques such as site-directed mutagenesis are also useful for modifying a heterologous sequence.

The term "isolated" refers to material that is substantially or essentially free from components which interfere with the activity of an enzyme. For a saccharide, protein, or nucleic acid of the invention, the term "isolated" refers to material that is substantially or essentially free from components which normally accompany the material as found in its native state. Typically, an isolated saccharide, protein, or nucleic acid of the invention is at least about 80% pure, usually at least about 90%, and preferably at least about 95% pure as measured by band intensity on a silver stained gel or other method for determining purity. Purity or homogeneity can be indicated by a number of means well known in the art. For example, a protein or nucleic acid in a sample can be resolved by polyacrylamide gel electrophoresis, and then the protein or nucleic acid can be visualized by staining. For certain purposes high resolution of the protein or nucleic acid may be desirable and HPLC or a similar means for purification, for example, may be utilized.

The term "operably linked" refers to functional linkage between a nucleic acid expression control sequence (such as a promoter, signal sequence, or array of transcription factor binding sites) and a second nucleic acid sequence, wherein the expression control sequence affects transcription and/or translation of the nucleic acid corresponding to the second sequence.

The terms "identical" or percent "identity," in the context of two or more nucleic acids or protein sequences, refer to two or more sequences or subsequences that are the same or have a specified percentage of amino acid residues or nucleotides that are the same, when compared and aligned for maximum correspondence, as measured using one of the following sequence comparison algorithms or by visual inspection.

The phrase "substantially identical," in the context of two nucleic acids or proteins, refers to two or more sequences or subsequences that have greater than about 60% nucleic acid or amino acid sequence identity, 65%, 70%, 75%, 80%, 85%, 90%, preferably 91%, 92%, 93%, 94%, 95%, 96%, 97%, 98% or 99% nucleotide or amino acid residue identity, when compared and aligned for maximum correspondence, as measured using one of the following sequence comparison algorithms or by visual inspection. Preferably, the substantial identity exists over a region of the sequences that is at least about 50 residues in length, more preferably over a region of at least about 100 residues, and most preferably the sequences are substantially identical over at least about 150 residues. In a most preferred embodiment, the sequences are substantially identical over the entire length of the coding regions.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally, *Current Protocols in Molecular Biology*, F. M. Ausubel et al., eds., Current Protocols, a joint venture between Greene Publishing Associates, Inc. and John Wiley & Sons, Inc., (1995 Supplement) (Ausubel)).

Examples of algorithms that are suitable for determining percent sequence identity and sequence similarity are the BLAST and BLAST 2.0 algorithms, which are described in Altschul et al. (1990) *J. Mol. Biol.* 215: 403-410 and Altschuel et al. (1977) *Nucleic Acids Res.* 25: 3389-3402, respectively. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always>0) and N (penalty score for mismatching residues; always<0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff, *Proc. Natl. Acad. Sci. USA* 89:10915 (1989)).

In addition to calculating percent sequence identity, the BLAST algorithm also performs a statistical analysis of the similarity between two sequences (see, e.g., Karlin & Altschul, *Proc. Natl. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

A further indication that two nucleic acid sequences or proteins are substantially identical is that the protein encoded by the first nucleic acid is immunologically cross reactive with the protein encoded by the second nucleic acid, as described below. Thus, a protein is typically substantially identical to a second protein, for example, where the two peptides differ only by conservative substitutions. Another indication that two nucleic acid sequences are substantially identical is that the two molecules hybridize to each other under stringent conditions, as described below.

The phrase "hybridizing specifically to" refers to the binding, duplexing, or hybridizing of a molecule only to a particular nucleotide sequence under stringent conditions when that sequence is present in a complex mixture (e.g., total cellular) DNA or RNA.

The term "stringent conditions" refers to conditions under which a probe will hybridize to its target subsequence, but to no other sequences. Stringent conditions are sequence-dependent and will be different in different circumstances. Longer sequences hybridize specifically at higher temperatures. Generally, stringent conditions are selected to be about 15° C. lower than the thermal melting point (Tm) for the specific sequence at a defined ionic strength and pH. The Tm is the temperature (under defined ionic strength, pH, and nucleic acid concentration) at which 50% of the probes complementary to the target sequence hybridize to the target sequence at equilibrium. (As the target sequences are generally present in excess, at Tm, 50% of the probes are occupied at equilibrium). Typically, stringent conditions will be those in which the salt concentration is less than about 1.0 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For selective or specific hybridization, a positive signal is typically at least two times background, preferably 10 times background hybridization. Exemplary stringent hybridization conditions can be following: 50% formamide, 5×SSC, and 1% SDS, incubating at 42° C., or, 5×SSC, 1% SDS, incubating at 65° C., with wash in 0.2×SSC, and 0.1% SDS at 65° C. For PCR, a temperature of about 36° C. is typical for low stringency amplification, although annealing temperatures may vary between about 32-48° C. depending on primer length. For high stringency PCR amplification, a temperature of about 62° C. is typical, although high stringency annealing temperatures can range from about 50° C. to about 65° C., depending on the primer length and specificity. Typical cycle conditions for both high and low stringency amplifications include a denaturation phase of 90-95° C. for 30-120 sec, an annealing phase lasting 30-120 sec, and an extension phase of about 72° C. for 1-2 min. Protocols and guidelines for low and high stringency amplification reactions are available, e.g., in Innis, et al. (1990) *PCR Protocols: A Guide to Methods and Applications* Academic Press, N.Y.

The phrases "specifically binds to a protein" or "specifically immunoreactive with", when referring to an antibody refers to a binding reaction which is determinative of the presence of the protein in the presence of a heterogeneous population of proteins and other biologics. Thus, under designated immunoassay conditions, the specified antibodies bind preferentially to a particular protein and do not bind in a significant amount to other proteins present in the sample. Specific binding to a protein under such conditions requires an antibody that is selected for its specificity for a particular protein. A variety of immunoassay formats may be used to select antibodies specifically immunoreactive with a particular protein. For example, solid-phase ELISA immunoassays are routinely used to select monoclonal antibodies specifically immunoreactive with a protein. See Harlow and Lane (1988) *Antibodies, A Laboratory Manual*, Cold Spring Harbor Publications, New York, for a description of immunoassay formats and conditions that can be used to determine specific immunoreactivity.

"Conservatively modified variations" of a particular polynucleotide sequence refers to those polynucleotides that encode identical or essentially identical amino acid sequences, or where the polynucleotide does not encode an amino acid sequence, to essentially identical sequences. Because of the degeneracy of the genetic code, a large number of functionally identical nucleic acids encode any given protein. For instance, the codons CGU, CGC, CGA, CGG, AGA, and AGG all encode the amino acid arginine. Thus, at every position where an arginine is specified by a codon, the codon can be altered to any of the corresponding codons described without altering the encoded protein. Such nucleic acid variations are "silent variations," which are one species of "conservatively modified variations." Every polynucleotide sequence described herein which encodes a protein also describes every possible silent variation, except where otherwise noted. One of skill will recognize that each codon in a nucleic acid (except AUG, which is ordinarily the only codon for methionine, and UGG which is ordinarily the only codon for tryptophan) can be modified to yield a functionally identical molecule by standard techniques. Accordingly, each "silent variation" of a nucleic acid which encodes a protein is implicit in each described sequence.

Furthermore, one of skill will recognize that individual substitutions, deletions or additions which alter, add or delete a single amino acid or a small percentage of amino acids (typically less than 5%, more typically less than 1%) in an encoded sequence are "conservatively modified variations" where the alterations result in the substitution of an amino acid with a chemically similar amino acid. Conservative substitution tables providing functionally similar amino acids are well known in the art.

One of skill will appreciate that many conservative variations of the fusion proteins and nucleic acid which encode the fusion proteins yield essentially identical products. For example, due to the degeneracy of the genetic code, "silent substitutions" (i.e., substitutions of a nucleic acid sequence which do not result in an alteration in an encoded protein) are an implied feature of every nucleic acid sequence which encodes an amino acid. As described herein, sequences are preferably optimized for expression in a particular host cell used to produce the chimeric glycosyltransferases (e.g., yeast, human, and the like). Similarly, "conservative amino acid substitutions," in one or a few amino acids in an amino acid sequence are substituted with different amino acids with highly similar properties (see, the definitions section, supra), are also readily identified as being highly similar to a particular amino acid sequence, or to a particular nucleic acid sequence which encodes an amino acid. Such conservatively substituted variations of any particular sequence are a feature of the present invention. See also, Creighton (1984) *Proteins*, W.H. Freeman and Company. In addition, individual substitutions, deletions or additions which alter, add or delete a single amino acid or a small percentage of amino acids in an encoded sequence are also "conservatively modified variations".

The practice of this invention can involve the construction of recombinant nucleic acids and the expression of genes in transfected host cells. Molecular cloning techniques to achieve these ends are known in the art. A wide variety of cloning and in vitro amplification methods suitable for the construction of recombinant nucleic acids such as expression vectors are well known to persons of skill. Examples of these techniques and instructions sufficient to direct persons of skill through many cloning exercises are found in Berger and Kimmel, *Guide to Molecular Cloning Techniques, Methods in Enzymology* volume 152 Academic Press, Inc., San Diego, Calif. (Berger); and *Current Protocols in Molecular Biology*, F. M. Ausubel et al., eds., Current Protocols, a joint venture between Greene Publishing Associates, Inc. and John Wiley & Sons, Inc., (1999 Supplement) (Ausubel). Suitable host cells for expression of the recombinant *H. pylori* fucosyltransferases are known to those of skill in the art, and include, for example, bacterial cells, including *E. coli*. Eucaryotic cells can also be used in the present invention, for example insect cells such as Sf 9 cell and yeast or fungal cells (e.g., *Aspergillus niger* or yeast).

Examples of protocols sufficient to direct persons of skill through in vitro amplification methods, including the polymerase chain reaction (PCR) the ligase chain reaction (LCR), Qβ-replicase amplification and other RNA polymerase mediated techniques are found in Berger, Sambrook, and Ausubel, as well as Mullis et al. (1987) U.S. Pat. No. 4,683,202; *PCR Protocols A Guide to Methods and Applications* (Innis et al. eds) Academic Press Inc. San Diego, Calif. (1990) (Innis); Arnheim & Levinson (Oct. 1, 1990) C&EN 36-47; *The Journal Of NIH Research* (1991) 3: 81-94; (Kwoh et al. (1989) *Proc. Natl. Acad. Sci. USA* 86: 1173; Guatelli et al. (1990) *Proc. Natl. Acad. Sci. USA* 87: 1874; Lomell et al. (1989) *J. Clin. Chem.* 35: 1826; Landegren et al. (1988) *Science* 241: 1077-1080; Van Brunt (1990) *Biotechnology* 8: 291-294; Wu and Wallace (1989) *Gene* 4: 560; and Barringer et al. (1990) *Gene* 89: 117. Improved methods of cloning in vitro amplified nucleic acids are described in Wallace et al., U.S. Pat. No. 5,426,039.

DETAILED DESCRIPTION OF THE INVENTION

The present invention provides for the first time bacterial α-1,3/4-fucosyltranferases, i.e., *H. pylori* fucosyltransferases, that transfer fucose from a donor substrate to an acceptor sugar on a glycoprotein. In addition, the fucosyltransferases are useful for producing fucosylated oligosaccharides and glycolipids.

Specifically, α-1,3/4-fucosyltransferases from the following *H. pylori* strains were cloned and analyzed: 915A2, 1111A2, 19C2B1, 1182B3, 19C2A5,26695, and 1218. Fucosyltransferases from the following *H. pylori* strains transferred fucose to Glc-NAc: 915A2, 1111A2, 19C2FutB, and 1182B3. The FutA gene product from *H. pylori* strain 19C2A5 transferred fucose to the reducing glucose of the LNnT acceptor, as did the FutB gene product from *H. pylori* strain 1218. The ability of FutA gene product from *H. pylori* strain 26695 to transfer fucose to glucose was confirmed.

A major advantage of the *H. pylori* α-1,3/4-fucosyltransferases over mammalian α-1,3/4-fucosyltransferases is that the *H. pylori* enzyme appears to be unaffected by the sialylation status of the acceptor. In addition some of the *H. pylori* fucosyltransferases add fucose exclusively to the N-acetylglucosamine (glcNAc) residue in acceptor sugars that contain both glucose and glcNAc residues. In contrast, mammalian an α-1,3/4-fucosyltransferases are sensitive to the degree of sialylation of the acceptor and some mammalian enzymes add to both glucose and glcNAc residues in the same acceptor. In addition bacterially expressed enzymes offer a large cost savings relative to the expression of mammalian gene products in Sf9 or CHO systems.

A. Cloning of *H. pylori* α-1,3/4-fucosyltranferases Proteins

Nucleic acids that encode glycosyltransferases, e.g., *H. pylori* α-1,3/4-fucosyltranferases and methods of obtaining such nucleic acids, are known to those of skill in the art. Suitable nucleic acids (e.g., cDNA, genomic, or subsequences (probes)) can be cloned, or amplified by in vitro methods such as the polymerase chain reaction (PCR), the ligase chain reaction (LCR), the transcription-based amplification system (TAS), or the self-sustained sequence replication system (SSR). A wide variety of cloning and in vitro amplification methodologies are well-known to persons of skill. Examples of these techniques and instructions sufficient to direct persons of skill through many cloning exercises are found in Berger and Kimmel, *Guide to Molecular Cloning Techniques, Methods in Enzymology* 152 Academic Press, Inc., San Diego, Calif. (Berger); Sambrook et al. (1989) *Molecular Cloning—A Laboratory Manual* (2nd ed.) Vol. 1-3, Cold Spring Harbor Laboratory, Cold Spring Harbor Press, NY, (Sambrook et al.); *Current Protocols in Molecular Biology*, F. M. Ausubel et al., eds., Current Protocols, a joint venture between Greene Publishing Associates, Inc. and John Wiley & Sons, Inc., (1994 Supplement) (Ausubel); Cashion et al., U.S. Pat. No. 5,017,478; and Carr, European Patent No. 0,246,864.

A DNA that encodes an *H. pylori* α-1,3/4-fucosyltranferase, or a subsequences thereof, can be prepared by any suitable method described above, including, for example, cloning and restriction of appropriate sequences with restriction enzymes. In one preferred embodiment, nucleic acids encoding *H. pylori* α-1,3/4-fucosyltranferases are isolated by routine cloning methods. A nucleotide sequence of a *H. pylori* α-1,3/4-fucosyltranferase as provided in, for example, GenBank or other sequence database (see above) can be used to provide probes that specifically hybridize to a *H. pylori* α-1,3/4-fucosyltranferases gene in a genomic DNA sample, or to an mRNA, encoding an *H. pylori* α-1,3/4-fucosyltranferase, in a total RNA sample (e.g., in a Southern or Northern blot). Once the target nucleic acid encoding a *H. pylori* α-1,3/4-fucosyltranferase is identified, it can be isolated according to standard methods known to those of skill in the art (see, e.g., Sambrook et al. (1989) *Molecular Cloning: A Laboratory Manual*, 2nd Ed., Vols. 1-3, Cold Spring Harbor Laboratory; Berger and Kimmel (1987) *Methods in Enzymology, Vol.* 152: *Guide to Molecular Cloning Techniques*, San Diego: Academic Press, Inc.; or Ausubel et al. (1987) *Current Protocols in Molecular Biology*, Greene Publishing and Wiley-Interscience, New York). Further, the isolated nucleic acids can be cleaved with restriction enzymes to create nucleic acids encoding the full-length *H. pylori* α-1,3/4-fucosyltranferase, or subsequences thereof, e.g., containing subsequences encoding at least a subsequence of a catalytic domain of a *H. pylori* α-1,3/4-fucosyltranferase. These restriction enzyme fragments, encoding an *H. pylori* α-1,3/4-fucosyltranferase or subsequences thereof, may then be ligated, for example, to produce a nucleic acid encoding an *H. pylori* α-1,3/4-fucosyltranferase protein.

A nucleic acid encoding an *H. pylori* α-1,3/4-fucosyltranferase, or a subsequence thereof, can be characterized by assaying for the expressed product. Assays based on the detection of the physical, chemical, or immunological properties of the expressed protein can be used. For example, one can identify a cloned *H. pylori* α-1,3/4-fucosyltranferases, by the ability of a protein encoded by the nucleic acid to catalyze the transfer of a fucose residue from a donor substrate to an acceptor substrate. In one method, capillary electrophoresis is employed to detect the reaction products. This highly sensitive assay involves using either saccharide or disaccharide aminophenyl derivatives which are labeled with fluorescein as described in Wakarchuk et al. (1996) *J. Biol. Chem.* 271 (45): 28271-276. For example, to assay for a *Neisseria* lgtC enzyme, either FCHASE-AP-Lac or FCHASE-AP-Gal can be used, whereas for the *Neisseria* lgtB enzyme an appropriate reagent is FCHASE-AP-GlcNAc (Id.). Other methods for detection of a fucosylated reation product include thin layer chromatography and GC/MS.

Also, a nucleic acid encoding an *H. pylori* α-1,3/4-fucosyltranferase, or a subsequence thereof, can be chemically synthesized. Suitable methods include the phosphotriester method of Narang et al. (1979) *Meth. Enzymol.* 68: 90-99; the phosphodiester method of Brown et al. (1979) *Meth. Enzymol.* 68: 109-151; the diethylphosphoramidite method of Beaucage et al. (1981) *Tetra. Lett.*, 22: 1859-1862; and the solid support method of U.S. Pat. No. 4,458,066. Chemical synthesis produces a single stranded oligonucleotide. This can be converted into double stranded DNA by hybridization with a complementary sequence, or by polymerization with a DNA polymerase using the single strand as a template. One of skill recognizes that while chemical synthesis of DNA is often limited to sequences of about 100 bases, longer sequences may be obtained by the ligation of shorter sequences.

Nucleic acids encoding *H. pylori* α-1,3/4-fucosyltranferases, or subsequences thereof, can be cloned using DNA amplification methods such as polymerase chain reaction (PCR). Thus, for example, the nucleic acid sequence or subsequence is PCR amplified, using a sense primer containing one restriction enzyme site (e.g., NdeI) and an antisense primer containing another restriction enzyme site (e.g., HindIII). This will produce a nucleic acid encoding the desired *H. pylori* α-1,3/4-fucosyltranferases or subsequence and having terminal restriction enzyme sites. This nucleic acid can then be easily ligated into a vector containing a nucleic acid encoding the second molecule and having the appropriate corresponding restriction enzyme sites. Suitable PCR primers can be determined by one of skill in the art using the sequence information provided in GenBank or other sources. Appropriate restriction enzyme sites can also be added to the nucleic acid encoding the *H. pylori* α-1,3/4-fucosyltranferase protein or protein subsequence by site-directed mutagenesis. The plasmid containing the *H. pylori* α-1,3/4-fucosyltranferase-encoding nucleotide sequence or subsequence is cleaved with the appropriate restriction endonuclease and then ligated into an appropriate vector for amplification and/or expression according to standard methods. Examples of techniques sufficient to direct persons of skill through in vitro amplification methods are found in Berger, Sambrook, and Ausubel, as well as Mullis et al., (1987) U.S. Pat. No. 4,683,202; *PCR Protocols A Guide to Methods and Applications* (Innis et al., eds) Academic Press Inc. San Diego, Calif. (1990) (Innis); Anaheim & Levinson (Oct. 1, 1990) C&EN 36-47; *The Journal Of NIH Research* (1991) 3: 81-94; (Kwoh et al. (1989) *Proc. Natl. Acad. Sci. USA* 86: 1173; Guatelli et al. (1990) *Proc. Natl. Acad. Sci. USA* 87, 1874; Lomell et al. (1989) *J. Clin. Chem.*, 35: 1826; Landegren et al., (1988) *Science* 241: 1077-1080; Van Brunt (1990) *Biotechnology* 8: 291-294; Wu and Wallace (1989) *Gene* 4: 560; and Barringer et al. (1990) *Gene* 89: 117.

Other physical properties of a cloned *H. pylori* α-1,3/4-fucosyltranferase protein expressed from a particular nucleic acid, can be compared to properties of known *H. pylori* α-1,3/4-fucosyltranferases to provide another method of identifying suitable sequences or domains of the *H. pylori* α-1,3/4-fucosyltranferases that are determinants of acceptor substrate specificity and/or catalytic activity. Alternatively, a putative *H. pylori* α-1,3/4-fucosyltranferase gene or recombinant *H. pylori* α-1,3/4-fucosyltranferase gene can be mutated, and its role as an α-1,3/4-fucosyltranferases, or the role of particular sequences or domains established by detecting a variation in the structure of a carbohydrate normally produced by the unmutated, naturally-occurring, or control α-1,3/4-fucosyltranferases.

Functional domains of cloned *H. pylori* α-1,3/4-fucosyltranferases can be identified by using standard methods for mutating or modifying the g *H. pylori* α-1,3/4-fucosyltranferases and testing the modified or mutated proteins for activities such as acceptor substrate activity and/or catalytic activity, as described herein. The functional domains of the various *H. pylori* α-1,3/4-fucosyltranferases can be used to construct nucleic acids encoding α-1,3/4-fucosyltranferases proteins comprising the functional domains of one or more α-1,3/4-fucosyltranferases. These fusion proteins can then be tested for the desired acceptor substrate or catalytic activity.

In an exemplary approach to cloning nucleic acids encoding α-1,3/4-fucosyltranferase proteins, the known nucleic acid or amino acid sequences of cloned glycosyltransferases are aligned and compared to determine the amount of sequence identity between various glycosyltransferases. This information can be used to identify and select protein domains that confer or modulate glycosyltransferase activities, e.g., acceptor substrate activity and/or catalytic activity based on the amount of sequence identity between the glycosyltransferases of interest. For example, domains having sequence identity between the fucosyltransferases of interest, and that are associated with a known activity, can be used to construct fucosyltransferase proteins containing that domain, and having the activity associated with that domain (e.g., acceptor substrate specificity and/or catalytic activity).

B. Fusion Protein Comprising Accessory Enzymes Involved in Nucleotide Sugar Formation In some embodiments, the fusion polypeptides of the invention include, in addition to the α-1,3/4-fucosyltranferases catalytic domain(s) and/or other functional domains, at least one catalytic domain from an accessory enzyme.

Accessory enzymes include, for example, those enzymes that are involved in the formation of a nucleotide sugar. The accessory enzyme can be involved in attaching the sugar to a nucleotide, or can be involved in making the sugar or the nucleotide, for example. The nucleotide sugar is generally one that is utilized as a saccharide donor by the glycosyltransferase catalytic domain of the particular fusion polypeptide. α-1,3/4-fucosyltranferases utilize GDP-fucose as a sugar donor. Examples of fusion proteins comprising a functional domain from a glycosyltransferase and an accessory enzyme and methods to make such fusions are found for example in PCT/CA98/01180, U.S. Ser. No. 09/211,691 filed Dec. 14, 1998 both of which are herein incorporated by reference for all purposes.

Accessory enzymes that are involved in synthesis of nucleotide sugars are well known to those of skill in the art. For a review of bacterial polysaccharide synthesis and gene nomenclature, see, e.g., Reeves et al., *Trends Microbiol.* 4: 495-503 (1996). The methods described above for obtaining glycosyltransferase-encoding nucleic acids are also applicable to obtaining nucleic acids that encode enzymes involved in the formation of nucleotide sugars. For example, one can use one of nucleic acids known in the art, some of which are listed below, directly or as a probe to isolate a corresponding nucleic acid from other organisms of interest.

An example of a fusion polypeptide provided by the invention is used for producing a fucosylated soluble oligosaccharide. The donor nucleotide sugar for fucosyltransferases is GDP-fucose, which is relatively expensive to produce. To reduce the cost of producing the fucosylated oligosaccharide, the invention provides fusion polypeptides that can convert the relatively inexpensive GDP-mannose into GDP-fucose, and then catalyze the transfer of the fucose to an acceptor saccharide. These fusion polypeptides include a catalytic domain from at least one of a GDP-mannose dehydratase, a GDP-4-keto-6-deoxy-D-mannose 3,5-epimerase, or a GDP-4-keto-6-deoxy-L-glucose 4-reductase. When each of these enzyme activities is provided, one can convert GDP-mannose into GDP-fucose.

The nucleotide sequence of an *E. coli* gene cluster that encodes GDP-fucose-synthesizing enzymes is described by Stevenson et al. (1996) *J. Bacteriol.* 178: 4885-4893; GenBank Accession No. U38473). This gene cluster had been reported to include an open reading frame for GDP-mannose dehydratase (nucleotides 8633-9754; Stevenson et al., supra.). It was recently discovered that this gene cluster also contains an open reading frame that encodes an enzyme that has both 3,5 epimerization and 4-reductase activities (see, commonly assigned U.S. Pat. No. 6,500,661, issued Dec. 31, 2002), and thus is capable of converting the product of the GDP-mannose dehydratase reaction (GDP-4-keto-6-deoxymannose) to GDP-fucose. This ORF, which is designated YEF B, is found between nucleotides 9757-10722. Prior to this discovery that YEF B encodes an enzyme having two activities, it was not known whether one or two enzymes were required for conversion of GDP-4-keto-6-deoxymannose to GDP-fucose. The nucleotide sequence of a gene encoding the human Fx enzyme is found in GenBank Accession No. U58766.

Also provided are fusion polypeptides that include a mannosyltransferase catalytic domain and a catalytic domain of a GDP-Man pyrophosphorylase (EC 2.7.7.22), which converts Man-1-P to GDP-Man. Suitable genes are known from many organisms, including *E. coli:* GenBank U13629, AB010294, D43637 D13231, Bastin et al., *Gene* 164: 17-23 (1995), Sugiyama et al., *J. Bacteriol.* 180: 2775-2778 (1998), Sugiyama et al., *Microbiology* 140 (Pt 1): 59-71 (1994), Kido et al., *J. Bacteriol.* 177: 2178-2187 (1995); *Klebsiella pneumoniae:* GenBank AB010296, AB010295, Sugiyama et al., *J. Bacteriol.* 180: 2775-2778 (1998); *Salmonella enterica:* GenBank X56793 M29713, Stevenson et al., *J. Bacteriol.* 178: 4885-4893 (1996).

The fusion polypeptides of the invention for fucosylating a saccharide acceptor can also utilize enzymes that provide a minor or "scavenge" pathway for GDP-fucose formation. In this pathway, free fucose is phosphorylated by fucokinase to form fucose 1-phosphate, which, along with guanosine 5'-triphosphate (GTP), is used by GDP-fucose pyrophosphorylase to form GDP-fucose (Ginsburg et al., *J. Biol. Chem.,* 236: 2389-2393 (1961) and Reitman, *J. Biol. Chem.,* 255: 9900-9906 (1980)). Accordingly, a fucosyltransferase catalytic domain can be linked to a catalytic domain from a GDP-fucose pyrophosphorylase, for which suitable nucleic acids are described in copending, commonly assigned U.S. patent application Ser. No. 08/826,964, filed Apr. 9, 1997. Fucokinase-encoding nucleic acids are described for, e.g., *Haemophilus influenzae* (Fleischmann et al. (1995) Science 269:496-512) and *E. coli* (Lu and Lin (1989) *Nucleic Acids Res.* 17: 4883-4884).

Additional accessory enzymes from which one can obtain a catalytic domain are those that are involved in forming reactants consumed in a glycosyltransferase cycle. For example, any of several phosphate kinases are useful as accessory enzymes. Polyphosphate kinase (EC 2.7.4.1), for example, catalyzes the formation of ATP; nucleoside phosphate kinases (EC 2.7.4.4) can form the respective nucleoside diphosphates; creatine phosphate kinase (EC 2.7.3.2); myokinase (EC 2.7.4.3); N-acetylglucosamine acetyl kinase (EC 2.7.1.59); acetyl phosphate kinase; and pyruvate kinase (EC 2.7.1.40).

C. Expression Cassettes and Host Cells for Expressing Recombinant *H. pylori* α-1,3/4-fucosyltranferase Proteins Fusion proteins of the invention can be expressed in a variety of host cells, including *E. coli,* other bacterial hosts, and yeast. The host cells are preferably microorganisms, such as, for example, yeast cells, bacterial cells, or filamentous fungal cells. Examples of suitable host cells include, for example, *Azotobacter* sp. (e.g., *A. vinelandii*), *Pseudomonas* sp., *Rhizobium* sp., *Erwinia* sp., *Escherichia* sp. (e.g., *E. coli*), *Bacillus, Pseudomonas, Proteus, Salmonella, Serratia, Shigella, Rhizobia, Vitreoscilla, Paracoccus* and *Klebsiella* sp., among many others. The cells can be of any of several genera, including *Saccharomyces* (e.g., *S. cerevisiae*), *Candida* (e.g., *C. utilis, C. parapsilosis, C. krusei, C. versatilis, C. ipolytica, C. zeylanoides, C. guilliermondii, C. albicans,* and *C. humicola*), *Pichia* (e.g., *P. farinosa* and *P. ohmeri*), *Torulopsis* (e.g., *T. candida, T. sphaerica, T. xylinus, T. famata,* and *T. versatilis*), *Debaryomyces* (e.g., *D. subglobosus, D. cantarellii, D. globosus, D. hansenii,* and *D. japonicus*), *Zygosaccharomyces* (e.g., *Z. rouxii* and *Z. bailii*), *Kluyveromyces* (e.g., *K. marxianus*), *Hansenula* (e.g., *H. anomala* and *H. jadinii*), and *Brettanomyces* (e.g., *B. lambicus* and *B. anomalus*). Examples of useful bacteria include, but are not limited to, *Escherichia, Enterobacter, Azotobacter, Erwinia, Klebsielia.*

Typically, the polynucleotide that encodes the α-1,3/4-fucosyltranferase protein is placed under the control of a promoter that is functional in the desired host cell. An extremely wide variety of promoters are well known, and can be used in the expression vectors of the invention, depending on the particular application. Ordinarily, the promoter selected depends upon the cell in which the promoter is to be active. Other expression control sequences such as ribosome binding sites, transcription termination sites and the like are also optionally included. Constructs that include one or more of these control sequences are termed "expression cassettes." Accordingly, the invention provides expression cassettes into which the nucleic acids that encode fusion proteins are incorporated for high level expression in a desired host cell.

Expression control sequences that are suitable for use in a particular host cell are often obtained by cloning a gene that is expressed in that cell. Commonly used prokaryotic control sequences, which are defined herein to include promoters for transcription initiation, optionally with an operator, along with ribosome binding site sequences, include such commonly used promoters as the beta-lactamase (penicillinase) and lactose (lac) promoter systems (Change et al., *Nature* (1977) 198: 1056), the tryptophan (trp) promoter system (Goeddel et al., *Nucleic Acids Res.* (1980) 8: 4057), the tac promoter (DeBoer, et al., *Proc. Natl. Acad. Sci. U.S.A.* (1983) 80:21-25); and the lambda-derived $P_L$ promoter and N-gene ribosome binding site (Shimatake et al., *Nature* (1981) 292: 128). The particular promoter system is not critical to the invention, any available promoter that functions in prokaryotes can be used.

For expression of α-1,3/4-fucosyltranferase proteins in prokaryotic cells other than *E. coli*, a promoter that functions in the particular prokaryotic species is required. Such promoters can be obtained from genes that have been cloned from the species, or heterologous promoters can be used. For example, the hybrid trp-lac promoter functions in *Bacillus* in addition to *E. coli*.

A ribosome binding site (RBS) is conveniently included in the expression cassettes of the invention. An RBS in *E. coli*, for example, consists of a nucleotide sequence 3-9 nucleotides in length located 3-11 nucleotides upstream of the initiation codon (Shine and Dalgarno, *Nature* (1975) 254: 34; Steitz, *In Biological regulation and development: Gene expression* (ed. R. F. Goldberger), vol. 1, p. 349, 1979, Plenum Publishing, NY).

For expression of the α-1,3/4-fucosyltranferase proteins in yeast, convenient promoters include GAL1-10 (Johnson and Davies (1984) *Mol. Cell. Biol.* 4:1440-1448) ADH2 (Russell et al. (1983) *J. Biol. Chem.* 258:2674-2682), PHO5 (*EMBO J.* (1982) 6:675-680), and MFα (Herskowitz and Oshima (1982) in *The Molecular Biology of the Yeast Saccharomyces* (eds. Strathem, Jones, and Broach) Cold Spring Harbor Lab., Cold Spring Harbor, N.Y., pp. 181-209). Another suitable promoter for use in yeast is the ADH2/GAPDH hybrid promoter as described in Cousens et al., *Gene* 61:265-275 (1987). For filamentous fungi such as, for example, strains of the fungi *Aspergillus* (McKnight et al., U.S. Pat. No. 4,935, 349), examples of useful promoters include those derived from *Aspergillus nidulans* glycolytic genes, such as the ADH3 promoter (McKnight et al., *EMBO J.* 4: 2093 2099 (1985)) and the tpiA promoter. An example of a suitable terminator is the ADH3 terminator (McKnight et al.).

Either constitutive or regulated promoters can be used in the present invention. Regulated promoters can be advantageous because the host cells can be grown to high densities before expression of the fusion proteins is induced. High level expression of heterologous proteins slows cell growth in some situations. An inducible promoter is a promoter that directs expression of a gene where the level of expression is alterable by environmental or developmental factors such as, for example, temperature, pH, anaerobic or aerobic conditions, light, transcription factors and chemicals. Such promoters are referred to herein as "inducible" promoters, which allow one to control the timing of expression of the glycosyltransferase or enzyme involved in nucleotide sugar synthesis.

For *E. coli* and other bacterial host cells, inducible promoters are known to those of skill in the art. These include, for example, the lac promoter, the bacteriophage lambda $P_L$ promoter, the hybrid trp-lac promoter (Amann et al. (1983) *Gene* 25: 167; de Boer et al. (1983) *Proc. Nat'l. Acad. Sci. USA* 80: 21), and the bacteriophage T7 promoter (Studier et al. (1986) *J. Mol. Biol.*; Tabor et al. (1985) *Proc. Nat'l. Acad. Sci. USA* 82: 1074-8). These promoters and their use are discussed in Sambrook et al., supra. A particularly preferred inducible promoter for expression in prokaryotes is a dual promoter that includes a tac promoter component linked to a promoter component obtained from a gene or genes that encode enzymes involved in galactose metabolism (e.g., a promoter from a UDPgalactose 4-epimerase gene (galE)). The dual tac-gal promoter, which is described in PCT Patent Application Publ. No. WO98/20111, A construct that includes a polynucleotide of interest operably linked to gene expression control signals that, when placed in an appropriate host cell, drive expression of the polynucleotide is termed an "expression cassette." Expression cassettes that encode the fusion proteins of the invention are often placed in expression vectors for introduction into the host cell. The vectors typically include, in addition to an expression cassette, a nucleic acid sequence that enables the vector to replicate independently in one or more selected host cells. Generally, this sequence is one that enables the vector to replicate independently of the host chromosomal DNA, and includes origins of replication or autonomously replicating sequences. Such sequences are well known for a variety of bacteria. For instance, the origin of replication from the plasmid pBR322 is suitable for most Gram-negative bacteria. Alternatively, the vector can replicate by becoming integrated into the host cell genomic complement and being replicated as the cell undergoes DNA replication. A preferred expression vector for expression of the enzymes is in bacterial cells is pTGK, which includes a dual tac-gal promoter and is described in PCT Patent Application Publ. NO. WO98/20111.

The construction of polynucleotide constructs generally requires the use of vectors able to replicate in bacteria. A plethora of kits are commercially available for the purification of plasmids from bacteria (see, for example, EasyPrepJ, FlexiPrepJ, both from Pharmacia Biotech; StrataCleanJ, from Stratagene; and, QIAexpress Expression System, Qiagen). The isolated and purified plasmids can then be further manipulated to produce other plasmids, and used to transfect cells. Cloning in *Streptomyces* or *Bacillus* is also possible.

Selectable markers are often incorporated into the expression vectors used to express the polynucleotides of the invention. These genes can encode a gene product, such as a protein, necessary for the survival or growth of transformed host cells grown in a selective culture medium. Host cells not transformed with the vector containing the selection gene will not survive in the culture medium. Typical selection genes encode proteins that confer resistance to antibiotics or other toxins, such as ampicillin, neomycin, kanamycin, chloramphenicol, or tetracycline. Alternatively, selectable markers may encode proteins that complement auxotrophic deficiencies or supply critical nutrients not available from complex media, e.g., the gene encoding D-alanine racemase for *Bacilli*. Often, the vector will have one selectable marker that is functional in, e.g., *E. coli*, or other cells in which the vector is replicated prior to being introduced into the host cell. A number of selectable markers are known to those of skill in the art and are described for instance in Sambrook et al., supra.

Construction of suitable vectors containing one or more of the above listed components employs standard ligation techniques as described in the references cited above. Isolated plasmids or DNA fragments are cleaved, tailored, and re-ligated in the form desired to generate the plasmids required. To confirm correct sequences in plasmids constructed, the plasmids can be analyzed by standard techniques such as by restriction endonuclease digestion, and/or sequencing according to known methods. Molecular cloning techniques to achieve these ends are known in the art. A wide variety of cloning and in vitro amplification methods suitable for the construction of recombinant nucleic acids are well-known to persons of skill. Examples of these techniques and instructions sufficient to direct persons of skill through many cloning exercises are found in Berger and Kimmel, *Guide to Molecular Cloning Techniques, Methods in Enzymology*, Volume 152, Academic Press, Inc., San Diego, Calif. (Berger); and *Current Protocols in Molecular Biology*, F. M. Ausubel et al., eds., *Current Protocols*, a joint venture between Greene Publishing Associates, Inc. and John Wiley & Sons, Inc., (1998 Supplement) (Ausubel).

A variety of common vectors suitable for use as starting materials for constructing the expression vectors of the invention are well known in the art. For cloning in bacteria, common vectors include pBR322 derived vectors such as pBLUESCRIPT™, and λ-phage derived vectors. In yeast, vectors include Yeast Integrating plasmids (e.g., YIp5) and Yeast Replicating plasmids (the YRp series plasmids) and pGPD-2. Expression in mammalian cells can be achieved using a variety of commonly available plasmids, including pSV2, pBC 12BI, and p91023, as well as lytic virus vectors (e.g., vaccinia virus, adeno virus, and baculovirus), episomal virus vectors (e.g., bovine papillomavirus), and retroviral vectors (e.g., murine retroviruses).

The methods for introducing the expression vectors into a chosen host cell are not particularly critical, and such methods are known to those of skill in the art. For example, the expression vectors can be introduced into prokaryotic cells, including *E. coli*, by calcium chloride transformation, and into eukaryotic cells by calcium phosphate treatment or electroporation. Other transformation methods are also suitable.

Translational coupling may be used to enhance expression. The strategy uses a short upstream open reading frame derived from a highly expressed gene native to the translational system, which is placed downstream of the promoter, and a ribosome binding site followed after a few amino acid codons by a termination codon. Just prior to the termination codon is a second ribosome binding site, and following the termination codon is a start codon for the initiation of translation. The system dissolves secondary structure in the RNA, allowing for the efficient initiation of translation. See Squires, et. al. (1988), *J. Biol. Chem.* 263: 16297-16302.

The α-1,3/4-fucosyltranferase proteins can be expressed intracellularly, or can be secreted from the cell. Intracellular expression often results in high yields. If necessary, the amount of soluble, active fusion protein may be increased by performing refolding procedures (see, e.g., Sambrook et al., supra.; Marston et al., *Bio/Technology* (1984) 2: 800; Schoner et al., *Bio/Technology* (1985) 3: 151). In embodiments in which the α-1,3/4-fucosyltranferase proteins are secreted from the cell, either into the periplasm or into the extracellular medium, the DNA sequence is linked to a cleavable signal peptide sequence. The signal sequence directs translocation of the fusion protein through the cell membrane. An example of a suitable vector for use in *E. coli* that contains a promoter-signal sequence unit is pTA1529, which has the *E. coli* phoA promoter and signal sequence (see, e.g., Sambrook et al., supra.; Oka et al., *Proc. Natl. Acad. Sci. USA* (1985) 82: 7212; Talmadge et al., *Proc. Natl. Acad. Sci. USA* (1980) 77: 3988; Takahara et al., *J. Biol. Chem.* (1985) 260: 2670). In another embodiment, the fusion proteins are fused to a subsequence of protein A or bovine serum albumin (BSA), for example, to facilitate purification, secretion, or stability.

The α-1,3/4-fucosyltranferase proteins of the invention can also be further linked to other bacterial proteins. This approach often results in high yields, because normal prokaryotic control sequences direct transcription and translation. In *E. coli*, lacZ fusions are often used to express heterologous proteins. Suitable vectors are readily available, such as the pUR, pEX, and pMR100 series (see, e.g., Sambrook et al., supra.). For certain applications, it may be desirable to cleave the non-glycosyltransferase and/or accessory enzyme amino acids from the fusion protein after purification. This can be accomplished by any of several methods known in the art, including cleavage by cyanogen bromide, a protease, or by Factor $X_a$ (see, e.g., Sambrook et al., supra.; Itakura et al., *Science* (1977) 198: 1056; Goeddel et al., *Proc. Natl. Acad. Sci. USA* (1979) 76: 106; Nagai et al., *Nature* (1984) 309: 810; Sung et al., *Proc. Natl. Acad. Sci. USA* (1986) 83: 561). Cleavage sites can be engineered into the gene for the fusion protein at the desired point of cleavage.

More than one recombinant protein may be expressed in a single host cell by placing multiple transcriptional cassettes in a single expression vector, or by utilizing different selectable markers for each of the expression vectors which are employed in the cloning strategy.

A suitable system for obtaining recombinant proteins from *E. coli* which maintains the integrity of their N-termini has been described by Miller et al. *Biotechnology* 7:698-704 (1989). In this system, the gene of interest is produced as a C-terminal fusion to the first 76 residues of the yeast ubiquitin gene containing a peptidase cleavage site. Cleavage at the junction of the two moieties results in production of a protein having an intact authentic N-terminal reside.

D. Purification of α-1,3/4-fucosyltranferase Proteins

The *H. pylori* fucosyltransferase proteins of the present invention can be expressed as intracellular proteins or as proteins that are secreted from the cell, and can be used in this form, in the methods of the present invention. For example, a crude cellular extract containing the expressed intracellular or secreted *H. pylori* fucosyltransferase protein can used in the methods of the present invention.

Alternatively, the *H. pylori* fucosyltransferase proteins can be purified according to standard procedures of the art, including ammonium sulfate precipitation, affinity columns, column chromatography, gel electrophoresis and the like (see, generally, R. Scopes, *Protein Purification*, Springer-Verlag, N.Y. (1982), Deutscher, *Methods in Enzymology Vol. 182: Guide to Protein Purification*, Academic Press, Inc. N.Y. (1990)). Substantially pure compositions of at least about 70 to 90% homogeneity are preferred, and 98 to 99% or more homogeneity are most preferred. The purified proteins may also be used, e.g., as immunogens for antibody production.

To facilitate purification of the *H. pylori* α-1,3/4-fucosyltranferase proteins of the invention, the nucleic acids that encode the fusion proteins can also include a coding sequence for an epitope or "tag" for which an affinity binding reagent is available, i.e. a purification tag. Examples of suitable epitopes include the myc and V-5 reporter genes; expression vectors useful for recombinant production of fusion proteins having these epitopes are commercially available (e.g., Invitrogen (Carlsbad Calif.) vectors pcDNA3.1/Myc-His and pcDNA3.1/V5-His are suitable for expression in mammalian cells). Additional expression vectors suitable for attaching a tag to the *H. pylori* α-1,3/4-fucosyltranferase proteins of the invention, and corresponding detection systems are known to those of skill in the art, and several are commercially available (e.g., FLAG' (Kodak, Rochester N.Y.). Another example of a suitable tag is a polyhistidine sequence, which is capable of binding to metal chelate affinity ligands. Typically, six adjacent histidines (SEQ ID NO:76) are used, although one can use more or less than six. Suitable metal chelate affinity ligands that can serve as the binding moiety for a polyhistidine tag include nitrilo-tri-acetic acid (NTA) (Hochuli, E. (1990) "Purification of recombinant proteins with metal chelating adsorbents" In Genetic Engineering: Principles and Methods, J. K. Setlow, Ed., Plenum Press, NY; commercially available from Qiagen (Santa Clarita, Calif.)).

Purification tags also include maltose binding domains and starch binding domains. Purification of maltose binding domain proteins is know to those of skill in the art. Starch binding domains are described in WO 99/15636, herein incorporated by reference. Affinity purification of a fusion protein comprising a starch binding domain using a betacylodextrin (BCD)-derivatized resin is described in U.S. Ser. No. 60/468,374, filed May 5, 2003, herein incorporated by reference in its entirety.

Other haptens that are suitable for use as tags are known to those of skill in the art and are described, for example, in the Handbook of Fluorescent Probes and Research Chemicals (6th Ed., Molecular Probes, Inc., Eugene OR). For example, dinitrophenol (DNP), digoxigenin, barbiturates (see, e.g., U.S. Pat. No. 5,414,085), and several types of fluorophores are useful as haptens, as are derivatives of these compounds. Kits are commercially available for linking haptens and other moieties to proteins and other molecules. For example, where the hapten includes a thiol, a heterobifunctional linker such as SMCC can be used to attach the tag to lysine residues present on the capture reagent.

One of skill would recognize that modifications can be made to the α-1,3/4-fucosyltransferase catalytic or functional domains without diminishing their biological activity. Some modifications may be made to facilitate the cloning, expression, or incorporation of the catalytic domain into a fusion protein. Such modifications are well known to those of skill in the art and include, for example, the addition of codons at either terminus of the polynucleotide that encodes the catalytic domain to provide, for example, a methionine added at the amino terminus to provide an initiation site, or additional amino acids (e.g., poly His) placed on either terminus to create conveniently located restriction enzyme sites or termination codons or purification sequences.

E. Uses of the *H. pylori* fucosyltransferase Proteins

The invention provides *H. pylori* α-1,3/4-fucosyltranferase proteins and methods of using the *H. pylori* α-1,3/4-fucosyltranferase proteins to enzymatically synthesize glycoproteins, glycolipids, and oligosaccharide moieties. The glycosyltransferase reactions of the invention take place in a reaction medium comprising at least one *H. pylori* α1,3/4-fucosyltranferase, acceptor substrate, and donor substrate, and typically a soluble divalent metal cation. In some embodiments, accessory enzymes and substrates for the accessory enzyme catalytic moiety are also present, so that the accessory enzymes can synthesize the donor substrate for the *H. pylori* α-1,3/4-fucosyltranferase.

A number of methods of using glycosyltransferases to synthesize glycoproteins and glycolipids having desired oligosaccharide moieties are known. Exemplary methods are described, for instance, WO 96/32491, Ito et al. (1993) *Pure Appl. Chem.* 65: 753, and U.S. Pat. Nos. 5,352,670, 5,374,541, and 5,545,553.

The *H. pylori* fucosyltransferase proteins prepared as described herein can be used in combination with additional glycosyltransferases. For example, one can use a combination of recombinant sialyltransferase fusion protein and a recombinant *H. pylori* α-1,3/4-fucosyltranferases. By conducting two glycosyltransferase reactions in sequence in a single vessel, overall yields are improved over procedures in which an intermediate species is isolated. Moreover, cleanup and disposal of extra solvents and by-products is reduced. Similarly, the recombinant glycoosyltransferases can be used with recombinant accessory enzyme, which may or may not be present as a the fusion protein. In other embodiments, the *H. pylori* α-1,3/4-fucosyltranferase and additional glycosyltransferases or accessory enzymes are produced in the same cell and used to synthesize a desired end product.

The products produced by the above processes can be used without purification. However, standard, well known techniques, for example, thin or thick layer chromatography, ion exchange chromatography, or membrane filtration can be used for recovery of glycosylated saccharides. Also, for example, membrane filtration, utilizing a nanofiltration or reverse osmotic membrane as described in commonly assigned AU Patent No. 735695 may be used. As a further example, membrane filtration wherein the membranes have a molecular weight cutoff of about 1000 to about 10,000 Daltons can be used to remove proteins. As another example, nanofiltration or reverse osmosis can then be used to remove salts. Nanofilter membranes are a class of reverse osmosis membranes which pass monovalent salts but retain polyvalent salts and uncharged solutes larger than about 200 to about 1000 Daltons, depending upon the membrane used. Thus, for example, the oligosaccharides produced by the compositions and methods of the present invention can be retained in the membrane and contaminating salts will pass through.

F. Donor Substrates and Acceptor Substrates

Suitable donor substrates used by the *H. pylori* fucosyltransferase proteins and other glycosyltranferases in the methods of the invention include, but are not limited to, UDP-Glc, UDP-GlcNAc, UDP-Gal, UDP-GalNAc, GDP-Man, GDP-Fuc, UDP-GlcUA, and CMP-sialic acid. Guo et al., *Applied Biochem. and Biotech.* 68: 1-20 (1997)

Suitable acceptor substrates used by the *H. pylori* fucosyltransferase proteins and methods of the invention include, but are not limited to, polysaccharides, oligosaccharides, lipids, and glycolipids. For example, the oligosaccharide LNnT can be fucosylated to form LNFIII. The fucosyltransferases described herein can also be used in multienzyme systems to produce a desired product from a convenient starting material. For example, LNFIII was prepared on a multigram scale from lactose using the *H. pylori* α-1,3/4-fucosyltranferases from strain 1182 described herein, in combination with *Neisseria gonococcus* β-1,3N-acetylglucosaminyltransferase (lgtA) and *Neisseria gonococcus* β-1,4-galactosyltransferase (lgtB).

Suitable acceptor substrates used by the *H. pylori* fucosyltransferase proteins and methods of the invention include, but are not limited to, proteins, lipids, gangliosides and other biological structures (e.g., whole cells) that can be modified by the methods of the invention. Exemplary structures, which can be modified by the methods of the invention include any a of a number glycolipids, glycoproteins and carbohydrate structures on cells known to those skilled in the art as set forth is Table 1.

TABLE 1

Hormones and Growth Factors

G-CSF
GM-CSF
TPO
EPO
EPO variants
α-TNF
Leptin

Enzymes and Inhibitors t-PA
t-PA variants
Urokinase
Factors VII, VIII, IX, X
DNase
Glucocerebrosidase
Hirudin
α1 antitrypsin
Antithrombin III

Cytokines and Chimeric Cytokines

Interleukin-1 (IL-1), 1B, 2, 3, 4
Interferon-α (IFN-α)
IFN-α-2b
IFN-β
IFN-γ
Chimeric diptheria toxin-IL-2

Receptors and Chimeric Receptors

CD4
Tumor Necrosis Factor (TNF) receptor
Alpha-CD20
MAb-CD20
MAb-alpha-CD3
MAb-TNF receptor
MAb-CD4
PSGL-1
MAb-PSGL-1
Complement
GlyCAM or its chimera
N-CAM or its chimera
LFA-3
CTLA-IV

Monoclonal Antibodies (Immunoglobulins)

MAb-anti-RSV
MAb-anti-IL-2 receptor
MAb-anti-CEA
MAb-anti-platelet IIb/IIIa receptor
MAb-anti-EGF
MAb-anti-Her-2 receptor

Cells

Red blood cells
White blood cells (e.g., T cells, B cells, dendritic cells, macrophages, NK cells, neutrophils, monocytes and the like
Stem cells Examples of suitable acceptor substrates used in fucosyltransferase-catalyzed reactions, and examples of suitable acceptor substrates used in sialyltransferase-catalyzed reactions are described in Guo et al., *Applied Biochem. and Biotech.* 68: 1-20 (1997), but are not limited thereto.

The present invention provides *H. pylori* fucosyltransferase proteins (e.g., fucosyltransferases) that are selected for their ability to produce glycoproteins and glycolipids having desired oligosaccharide moieties. Similarly, if present, accessory enzymes are chosen based on an desired activated sugar substrate or on a sugar found on the product oligosaccharide.

One can readily identify suitable *H. pylori* fucosyltransferase proteins by reacting various amounts of a *H. pylori* α-1,3/4-fucosyltranferase protein of interest (e.g., 0.01-100 mU/mg protein) with a glycoprotein (e.g., at 1-10 mg/ml) to which is linked an oligosaccharide that has a potential acceptor site for glycosylation by the fusion protein of interest. The abilities of the recombinant glycosyltransferases fusion proteins of the present invention to add a sugar residue at the desired acceptor site are compared, and a *H. pylori* fucosyltransferase protein having the desired property (e.g., acceptor substrate specificity or catalytic activity) is selected.

In general, the efficacy of the enzymatic synthesis of glycoproteins and glycolipids, having desired oligosaccharide moieties, can be enhanced through use of recombinantly produced *H. pylori* α-1,3/4-fucosyltranferases proteins of the present invention. Recombinant techniques enable production of the recombinant *H. pylori* α-1,3/4-fucosyltranferase proteins in the large amounts that are required for large-scale glycoprotein and glycolipid modification.

Suitable glycoproteins and glycolipids for use by the *H. pylori* fucosyltransferase proteins and methods of the invention can be glycoproteins and glycolipids immobilized on a solid support during the glycosylation reaction. The term "solid support" also encompasses semi-solid supports. Preferably, the target glycoprotein or glycolipid is reversibly immobilized so that the respective glycoprotein or glycolipid can be released after the glycosylation reaction is completed. Many suitable matrices are known to those of skill in the art. Ion exchange, for example, can be employed to temporarily immobilize a glycoprotein or glycolipid on an appropriate resin while the glycosylation reaction proceeds. A ligand that specifically binds to the glycoprotein or glycolipid of interest can also be used for affinity-based immobilization. For example, antibodies that specifically bind to a glycoprotein are suitable. Also, where the glycoprotein of interest is itself an antibody or contains a fragment thereof, one can use protein A or G as the affinity resin. Dyes and other molecules that specifically bind to a glycoprotein or glycolipid of interest are also suitable.

The recombinant fusion protein of the invention can be constructed and expressed as a fusion protein with a molecular "tag" at one end, which facilitates purification of the protein, i.e., a purification tag. Such tags can also be used for immobilization of a protein of interest during the glycosylation reaction. Suitable tags include "epitope tags," which are a protein sequence that is specifically recognized by an antibody. Epitope tags are generally incorporated into fusion proteins to enable the use of a readily available antibody to unambiguously detect or isolate the fusion protein. A "FLAG tag" is a commonly used epitope tag, specifically recognized by a monoclonal anti-FLAG antibody, consisting of the sequence AspTyrLysAspAspAspAspLys (SEQ ID NO:75) or a substantially identical variant thereof. A mcy tag is another commonly used epitope tag. Other suitable tags are known to those of skill in the art, and include, for example, an affinity tag such as a hexahistidine (SEQ ID NO:76) peptide, which will bind to metal ions such as nickel or cobalt ions. Purification tags also include maltose binding domains and starch binding domains. Purification of maltose binding domain proteins is know to those of skill in the art. Starch binding domains are described in WO 99/15636, herein incorporated by reference. Affinity purification of a fusion protein comprising a starch binding domain using a betacylodextrin (BCD)-derivatized resin is described in U.S. Ser. No. 60/468, 374, filed May 5, 2003, herein incorporated by reference in its entirety.

Preferably, when the glycoprotein is a truncated version of the full-length glycoprotein, it preferably includes the biologically active subsequence of the full-length glycoprotein. Exemplary biologically active subsequences include, but are not limited to, enzyme active sites, receptor binding sites, ligand binding sites, complementarity determining regions of antibodies, and antigenic regions of antigens.

In some embodiments, the *H. pylori* fucosyltransferase proteins and methods of the present invention are used to enzymatically synthesize a glycoprotein or glycolipid that has a substantially uniform glycosylation pattern. The glycoproteins and glycolipids include a saccharide or oligosaccharide that is attached to a protein, glycoprotein, lipid, or glycolipid for which a glycoform alteration is desired. The saccharide or oligosaccharide includes a structure that can function as an acceptor substrate for a glycosyltransferase. When the acceptor substrate is glycosylated, the desired oligosaccharide moiety is formed. The desired oligosaccharide moiety is one that imparts the desired biological activity upon the glycoprotein or glycolipid to which it is attached. In the compositions of the invention, the preselected saccharide residue is linked to at least about 30% of the potential acceptor sites of interest. More preferably, the preselected saccharide residue is linked to at least about 50% of the potential acceptor substrates of interest, and still more preferably to at least 70% of the potential acceptor substrates of interest. In situations in which the starting glycoprotein or glycolipid exhibits heterogeneity in the oligosaccharide moiety of interest (e.g., some of the oligosaccharides on the starting glycoprotein or glycolipid already have the preselected saccharide residue attached to the acceptor substrate of interest), the recited percentages include such pre-attached saccharide residues.

The term "altered" refers to the glycoprotein or glycolipid of interest having a glycosylation pattern that, after application of the *H. pylori* fucosyltransferase proteins and methods of the invention, is different from that observed on the glycoprotein as originally produced. An example of such glycoconjugates are glycoproteins in which the glycoforms of the glycoproteins are different from those found on the glycoprotein when it is produced by cells of the organism to which the glycoprotein is native. Also provided are *H. pylori* fucosyltransferase proteins and methods of using such fusion proteins for enzymatically synthesizing glycoproteins and glycolipids in which the glycosylation pattern of these glycoconjugates are modified compared to the glycosylation pattern of the glycoconjugates as originally produced by a host cell, which can be of the same or a different species than the cells from which the native glycoconjugates are produced.

One can assess differences in glycosylation patterns not only by structural analysis of the glycoproteins and glycolipids, but also by comparison of one or more biological activities of the glycoconjugates. For example, a glycoprotein having an "altered glycoform" includes one that exhibits an improvement in one more biological activities of the glycoprotein after the glycosylation reaction compared to the unmodified glycoprotein. For example, an altered glycoconjugate includes one that, after application of the *H. pylori* fucosyltransferase proteins and methods of the invention, exhibits a greater binding affinity for a ligand or receptor of interest, a greater therapeutic half-life, reduced antigenicity, and targeting to specific tissues. The amount of improvement observed is preferably statistically significant, and is more preferably at least about a 25% improvement, and still more preferably is at least about 50%, 60%, 70%, and even still more preferably is at least 80%.

G. Fucosyltransferase Reactions

The *H. pylori* fucosyltransferase proteins, acceptor substrates, donor substrates and other reaction mixture ingredients, including other glycosyltransferases and accessory enzymes are combined by admixture in an aqueous reaction medium. The medium generally has a pH value of about 5 to about 8.5. The selection of a medium is based on the ability of the medium to maintain pH value at the desired level. Thus, in some embodiments, the medium is buffered to a pH value of about 7.5. If a buffer is not used, the pH of the medium should be maintained at about 5 to 8.5, depending upon the particular glycosyltransferase used. For fucosyltransferases, the pH range is preferably maintained from about 6.0 to 8.0. For sialyltransferases, the range is preferably from about 5.5 and about 7.5.

Enzyme amounts or concentrations are expressed in activity units, which is a measure of the initial rate of catalysis. One activity unit catalyzes the formation of 1 µmol of product per minute at a given temperature (typically 37° C.) and pH value (typically 7.5). Thus, 10 units of an enzyme is a catalytic amount of that enzyme where 10 µmol of substrate are converted to 10 µmol of product in one minute at a temperature of 37° C. and a pH value of 7.5.

The reaction mixture may include divalent metal cations ($Mg^{2+}$, $Mn^{2+}$). The reaction medium may also comprise solubilizing detergents (e.g., Triton or SDS) and organic solvents such as methanol or ethanol, if necessary. The enzymes can be utilized free in solution or can be bound to a support such as a polymer. The reaction mixture is thus substantially homogeneous at the beginning, although some precipitate can form during the reaction.

The temperature at which an above process is carried out can range from just above freezing to the temperature at which the most sensitive enzyme denatures. That temperature range is preferably about 0° C. to about 45° C., and more preferably at about 20° C. to about 37° C.

The reaction mixture so formed is maintained for a period of time sufficient to obtain the desired high yield of desired oligosaccharide products, including determinants present on oligosaccharide groups attached to the glycoprotein to be glycosylated. For large-scale preparations, the reaction will often be allowed to proceed for between about 0.5-240 hours, and more typically between about 1-18 hours.

In embodiments in which more than one glycosyltransferase is used to obtain the oligosaccharide products, the enzymes and reagents for a second glycosyltransferase reaction can be added to the reaction medium once the first glycosyltransferase reaction has neared completion. For some combinations of enzymes, the glycosyltransferases and corresponding substrates can be combined in a single initial reaction mixture; the enzymes in such simultaneous reactions preferably do not form a product that cannot serve as an acceptor for the other enzyme. By conducting two glycosyltransferase reactions in sequence in a single vessel, overall yields are improved over procedures in which an intermediate species is isolated. Moreover, cleanup and disposal of extra solvents and by-products is reduced. In addition, in some embodiments, the fucosyltransferase and additionally glycosyltransferases or accessory enzymes are expressed in the same host cell and the desired product is synthesized within the host cell.

One or more of the glycosyltransferase reactions can be carried out as part of a glycosyltransferase cycle. Preferred conditions and descriptions of glycosyltransferase cycles have been described. A number of glycosyltransferase cycles (for example, sialyltransferase cycles, galactosyltransferase cycles, and fucosyltransferase cycles) are described in U.S. Pat. No. 5,374,541 and WO 9425615 A. Other glycosyltransferase cycles are described in Ichikawa et al. *J. Am. Chem. Soc.* 114:9283 (1992), Wong et al. *J. Org. Chem.* 57: 4343 (1992), DeLuca, et al., *J. Am. Chem. Soc.* 117:5869-5870

(1995), and Ichikawa et al. In *Carbohydrates and Carbohydrate Polymers*. Yaltami, ed. (ATL Press, 1993).

Other glycosyltransferases can be substituted into similar transferase cycles as have been described in detail for the fucosyltransferases and sialyltransferases. In particular, the glycosyltransferase can also be, for instance, glucosyltransferases, e.g., Alg8 (Stagljov et al., *Proc. Natl. Acad. Sci. USA* 91:5977 (1994)) or Alg5 (Heesen et al. *Eur. J. Biochem.* 224:71 (1994)), N-acetylgalactosaminyltransferases such as, for example, α(1,3) N-acetylgalactosaminyltransferase, β(1,4) N-acetylgalactosaminyltransferases (Nagata et al. *J. Biol. Chem.* 267:12082-12089 (1992) and Smith et al. *J. Biol Chem.* 269:15162 (1994)) and polypeptide N-acetylgalactosaminyltransferase (Homa et al. *J. Biol Chem.* 268:12609 (1993)). Suitable N-acetylglucosaminyltransferases include GnTI (2.4.1.101, Hull et al., *BBRC* 176:608 (1991)), GnTII, and GnTIII (Ihara et al. *J. Biochem.* 113:692 (1993)), GnTV (Shoreiban et al. *J. Biol. Chem.* 268: 15381 (1993)), O-linked N-acetylglucosaminyltransferase (Bierhuizen et al. *Proc. Natl. Acad. Sci. USA* 89:9326 (1992)), N-acetylglucosamine-1-phosphate transferase (Rajput et al. *Biochem J.* 285:985 (1992), and hyaluronan synthase. Suitable mannosyltransferases include α(1,2) mannosyltransferase, α(1,3) mannosyltransferase, β(1,4) mannosyltransferase, Dol-P-Man synthase, OCh1, and Pmt1.

For the above glycosyltransferase cycles, the concentrations or amounts of the various reactants used in the processes depend upon numerous factors including reaction conditions such as temperature and pH value, and the choice and amount of acceptor saccharides to be glycosylated. Because the glycosylation process permits regeneration of activating nucleotides, activated donor sugars and scavenging of produced PPi in the presence of catalytic amounts of the enzymes, the process is limited by the concentrations or amounts of the stoichiometric substrates discussed before. The upper limit for the concentrations of reactants that can be used in accordance with the method of the present invention is determined by the solubility of such reactants.

Preferably, the concentrations of activating nucleotides, phosphate donor, the donor sugar and enzymes are selected such that glycosylation proceeds until the acceptor is consumed.

Each of the enzymes is present in a catalytic amount. The catalytic amount of a particular enzyme varies according to the concentration of that enzyme's substrate as well as to reaction conditions such as temperature, time and pH value. Means for determining the catalytic amount for a given enzyme under preselected substrate concentrations and reaction conditions are well known to those of skill in the art.

The fucosyltransferase reaction can be carried out using an oligosaccharide or polysaccharide as an acceptor molecule. Suitable acceptor substrates used by the *H. pylori* fucosyltransferase proteins and methods of the invention include, but are not limited to, polysaccharides, oligosaccharides, lipids, and glycolipids. For example, the oligosaccharide LNnT can be fucosylated to form LNFIII. The fucosyltransferases described herein can also be used in multienzyme systems to produce a desired product from a convenient starting material. For example, LNFIII was prepared on a multigram scale from lactose using the *H. pylori* α-1,3/4-fucosyltranferases from strain 1182 described herein, in combination with *Neisseria gonococcus* β-1,3N-acetylglucosaminyltransferase (lgtA) and *Neisseria gonococcus* β-1,4-galactosyltransferase (lgtB).

The recombinant fucosyltransferase fusion protein used in the methods of the invention is chosen based upon its ability to fucosylate the fucosyltransferase acceptor substrates of interest. Preferably, the fucosyltransferase is assayed for suitability using a fucosyltransferase acceptor substrate that is attached to a soluble saccharide or oligosaccharide. The use of a soluble saccharide or oligosaccharide acceptor substrate in the assay to determine fucosyltransferase activity allows one to select a fucosyltransferase that produces the desired oligosaccharide product.

The fucosyltransferase reaction can be carried out using a lipid or glycolipid as an acceptor molecule. Many saccharides require the presence of particular fucosylated structures in order to exhibit biological activity. Intercellular recognition mechanisms often require a fucosylated oligosaccharide. For example, a number of proteins that function as cell adhesion molecules, including P-selectin, E-selectin, bind specific cell surface fucosylated carbohydrate structures, for example, the sialyl Lewis x and the sialyl Lewis a structures. In addition, the specific carbohydrate structures that form the ABO blood group system are fucosylated. The carbohydrate structures in each of the three groups share a Fucα1,2Galβ1-dissacharide unit. In blood group O structures, this disaccharide is the terminal structure. The group A structure is formed by an α1,3 GalNAc transferase that adds a terminal GalNAc residue to the dissacharide. The group B structure is formed by an β1,3 galactosyltransferase that adds terminal galactose residue. The Lewis blood group structures are also fucosylated. For example the Lewis x and Lewis a structures are Galβ1,4 (Fucα1,3)GlcNac and Galβ1,4(Fucα1,4)GlcNac, respectively. Both these structures can be further sialylated (NeuAcα2,3-) to form the corresponding sialylated structures. Other Lewis blood group structures of interest are the Lewis y and b structures which are Fucα1,2Galβ1,4(Fucα1, 3)GlcNAcβ-OR and Fucα1,2Galβ1,3(Fucα1,4)GlcNAc-OR, respectively. For a description of the structures of the ABO and Lewis blood group structures and the enzymes involved in their synthesis see, *Essentials of Glycobiology*, Varki et al. eds., Chapter 16 (Cold Spring Harbor Press, Cold Spring Harbor, N.Y., 1999).

The recombinant fucosyltransferase fusion protein used in the methods of the invention is chosen based upon its ability to fucosylate the fucosyltransferase acceptor substrates of interest. Preferably, the fucosyltransferase is assayed for suitability using a fucosyltransferase acceptor substrate that is attached to a lipid or glycolipid. The use of a glycolipid-linked acceptor substrate, rather than an acceptor substrate that is part of a soluble oligosaccharide, in the assay to determine fucosyltransferase activity allows one to select a fucosyltransferase that produces the selected fucosylation pattern on the glycolipid.

Fucosyltransferases have been used in synthetic pathways to transfer a fucose unit from guanosine-5'-diphosphofucose to a specific hydroxyl of a saccharide acceptor. For example, Ichikawa prepared sialyl Lewis-X by a method that involves the fucosylation of sialylated lactosamine with a cloned fucosyltransferase (Ichikawa et al., *J. Am. Chem. Soc.* 114: 9283-9298 (1992)). Lowe has described a method for expressing non-native fucosylation activity in cells, thereby producing fucosylated glycoproteins, cell surfaces, etc. (U.S. Pat. No. 5,955,347).

In one embodiment, the methods of the invention are practiced by contacting a substrate, having an acceptor moiety for a fucosyltransferase, with a reaction mixture that includes a fucose donor moiety, a fucosyltransferase, and other reagents required for fucosyltransferase activity. The substrate is incubated in the reaction mixture for a sufficient time and under appropriate conditions to transfer fucose from the fucose donor moiety to the fucosyltransferase acceptor moiety. In preferred embodiments, the fucosyltransferase catalyzes the fucosylation of at least 60% of the fucosyltransferase respective acceptor moieties in the composition.

Specificity for a selected substrate is only the first criterion a preferred fucosyltransferase should satisfy. The fucosyltransferase used in the method of the invention is preferably also able to efficiently fucosylate a variety of substrates, and support scale-up of the reaction to allow the fucosylation of at least about 500 mg of the substrate. More preferably, the fucosyltransferase will support the scale of the fucosylation reaction to allow the synthesis of at least about 1 kg, and more preferably, at least 10 kg of substrate with relatively low cost and infrastructure requirements.

Suitable acceptor moieties for fucosyltransferase-catalyzed attachment of a fucose residue include, but are not limited to, GlcNAc-OR, Galβ1,3GlcNAc-OR, NeuAcα2,3Galβ1,3GlcNAc-OR, Galβ1,4GlcNAc-OR and NeuAcα2,3Galβ1,4GlcNAc-OR, where R is an amino acid, a saccharide, an oligosaccharide or an aglycon group having at least one carbon atom. R is linked to or is part of a substrate. The appropriate fucosyltransferase for a particular reaction is chosen based on the type of fucose linkage that is desired (e.g., α2, α3, or α4), the particular acceptor of interest, and the ability of the fucosyltransferase to achieve the desired high yield of fucosylation. Suitable fucosyltransferases and their properties are described above.

If a sufficient proportion of the substrate-linked oligosaccharides in a composition does not include a fucosyltransferase acceptor moiety, one can synthesize a suitable acceptor. For example, one preferred method for synthesizing an acceptor for a fucosyltransferase involves use of a GlcNAc transferase to attach a GlcNAc residue to a GlcNAc transferase acceptor moiety, which is present on the substrate-linked oligosaccharides. In preferred embodiments a transferase is chosen, having the ability to glycosylate a large fraction of the potential acceptor moieties of interest. The resulting GlcNAcP-OR can then be used as an acceptor for a fucosyltransferase.

The resulting GlcNAcβ-OR moiety can be galactosylated prior to the fucosyltransferase reaction, yielding, for example, a Galβ1,3GlcNAc-OR or Gal β1,4GlcNAc-OR residue. In some embodiments, the galactylation and fucosylation steps can be carried out simultaneously. By choosing a fucosyltransferase that requires the galactosylated acceptor, only the desired product is formed. Thus, this method involves:
  (a) galactosylating a compound of the formula GlcNAcβ-OR with a galactosyltransferase in the presence of a UDP-galactose under conditions sufficient to form the compounds Galβ1,4GlcNAcβ-OR or Galβ1,3GlcNAc-OR; and
  (b) fucosylating the compound formed in (a) using a fucosyltransferase in the presence of GDP-fucose under conditions sufficient to form a compound selected from:
    Fucα1,2Galβ1,4GlcNAc1β-O1R;
    Fucα1,2Galβ1,3GlcNAc-OR;
    Fucα1,2Galβ1,4GalNAcl -O1 R;
    Fucα1,2Galβ1,3GalNAc-OR;
    Galβ1,4(Fuc1,α3)GlcNAc-OR; or
    Galβ1,3(Fucα1,4)GlcNAc-OR.

One can add additional fucose residues to the above structures by including an additional fucosyltransferase, which has the desired activity. For example, the methods can form oligosaccharide determinants such as Fucα1,2Galβ1,4(Fucα1,3)GlcNAcβ-OR and Fucα1,2Galβ1,3(Fucα1,4)GlcNAc-OR. Thus, in another preferred embodiment, the method includes the use of at least two fucosyltransferases. The multiple fucosyltransferases are used either simultaneously or sequentially. When the fucosyltransferases are used sequentially, it is generally preferred that the glycoprotein is not purified between the multiple fucosylation steps. When the multiple fucosyltransferases are used simultaneously, the enzymatic activity can be derived from two separate enzymes or, alternatively, from a single enzyme having more than one fucosyltransferase activity.

The fucosyltransferase reaction can carried out by contacting recombinant fucosyltransferase protein of the present invention with a mixture that includes, for example, multiple copies of a glycoprotein species, a majority of which preferably have one or more linked oligosaccharide groups that include an acceptor substrate for a fucosyltransferase; fucose donor substrate; and other reagents required for fucosyltransferase activity. The glycoprotein is incubated in the reaction mixture for a sufficient time and under appropriate conditions to transfer fucose from a donor substrate to a fucosyltransferase acceptor substrate.

The recombinant fucosyltransferase fusion protein used in the methods of the invention is chosen based upon its ability to fucosylate the fucosyltransferase acceptor substrates of interest. Preferably, the fucosyltransferase is assayed for suitability using a fucosyltransferase acceptor substrate that is attached to a glycoprotein. The use of a glycoprotein-linked acceptor substrate, rather than an acceptor substrate that is part of a soluble oligosaccharide, in the assay to determine fucosyltransferase activity allows one to select a fucosyltransferase that produces the selected fucosylation pattern on the glycoprotein.

In a preferred embodiment, the recombinant fucosyltransferase fusion protein of the present invention has a high level of expression in cells and/or high enzymatic activity (e.g., high specificity for a selected substrate and/or high catalytic activity). In another preferred embodiment, the fucosyltransferase is useful in a method for fucosylating a commercially important recombinant or transgenic glycoprotein. The fucosyltransferase used in the method of the invention is preferably also able to efficiently fucosylate a variety of glycoproteins, and support scale-up of the reaction to allow the fucosylation of at least about 500 mg of the glycoprotein. More preferably, the fucosyltransferase will support the scale of the fucosylation reaction to allow the synthesis of at least about 1 kg, and more preferably, at least 10 kg of recombinant glycoprotein with relatively low cost and infrastructure requirements.

In an exemplary embodiment, the method of the invention results in the formation on a glycoprotein of at least one ligand for a selectin. Confirmation of the formation of the ligand is assayed in an operational manner by probing the ability of the glycoprotein to interact with a selectin. The interaction between a glycoprotein and a specific selectin is measurable by methods familiar to those in the art ( see, for example, Jutila et al., *J. Immunol.* 153: 3917-28 (1994); Edwards et al., *Cytometry* 43(3): 211-6 (2001); Stahn et al., *Glycobiology* 8: 311-319 (1998); Luo et al., *J. Cell Biochem.* 80(4):522-31 (2001); Dong et al., *J. Biomech.* 33(1): 35-43 (2000); Jung et al., *J. Immunol.* 162(11): 6755-62 (1999); Keramidaris et al., *J. Allergy Clin. Immunol.* 107(4): 734-8 (2001); Fieger et al., *Biochim. Biophys. A cta* 1524(1): 75-85 (2001); Bruehl et al., *J. Biol. Chem.* 275(42): 32642-8 (2000); Tangemann et al., *J. Exp. Med.* 190(7): 935-42 (1999); Scalia et al., *Circ. Res.* 84(1): 93-102 (1999); Alon et al., *J. Cell Biol.* 138(5): 1169-80 (1997); Steegmaier et al., *Eur. J. Immunol.* 27(6): 1339-45 (1997); Stewart et al., *J. Med. Chem.* 44(6): 988-1002 (2001); Schurmann et al, *Gut* 36(3): 411-8 (1995); Burrows et al., *J. Clin. Pathol.* 47(10): 939-44 (1994)).

Suitable acceptor substrates for fucosyltransferase-catalyzed attachment of a fucose residue include, but are not limited to, GlcNAc-OR, Galβ1,3GlcNAc-OR, NeuAcα2,3Galβ1,3GlcNAc-OR, Galβ1,4GlcNAc-OR and NeuAcα2,3Galβ1,4GlcNAc-OR, where R is an amino acid, a saccharide, an oligosaccharide or an aglycon group having at least one carbon atom. R is linked to or is part of a glycoprotein. The appropriate fucosyltransferase for a particular reaction is chosen based on the type of fucose linkage that is desired (e.g., α2, α3, or α4), the particular acceptor of interest, and the ability of the fucosyltransferase to achieve the desired high yield of fucosylation. Suitable fucosyltransferases and their properties are described above.

If a sufficient proportion of the glycoprotein-linked oligosaccharides in a composition does not include a fucosyltransferase acceptor substrate, one can synthesize a suitable acceptor. For example, one preferred method for synthesizing an acceptor for a fucosyltransferase involves use of a GlcNAc transferase to attach a GlcNAc residue to a GlcNAc transferase acceptor substrate, which is present on the glycoprotein-linked oligosaccharides. In preferred embodiments a transferase is chosen, having the ability to glycosylate a large fraction of the potential acceptor substrates of interest. The resulting GlcNAcβ-OR can then be used as an acceptor for a fucosyltransferase.

The resulting GlcNAcβ-OR moiety can be galactosylated prior to the fucosyltransferase reaction, yielding, for example, a Galβ1,3GlcNAc-OR or Gal β1,4GlcNAc-OR residue. In some embodiments, the galactosylation and fucosylation steps are carried out simultaneously. Thus, this method involves:

(a) galactosylating a compound of the formula GlcNAcβ-OR with a galactosyltransferase in the presence of a UDP-galactose under conditions sufficient to form the compounds Galβ1,4GlcNAcβ-OR or Galβ1,3GlcNAc-OR; and (b) fucosylating the compound formed in (a) using a fucosyltransferase in the presence of GDP-fucose under conditions sufficient to form a compound selected from:
Fucα1,2Galβ1,4GlcNAc1β-O1R;
Fucα1,2Galβ1,3GlcNAc-OR;
Fucα1,2Galβ1,4GalNAc1β-O1R;
Fucα1,2Galβ1,3GalNAc-OR;
Galβ1,4(Fuc1,α3)GlcNAcβ-OR; or
Galβ1,3(Fucα1,4)GlcNAc-OR.

One can add additional fucose residues to a fucosylated glycoprotein treating the fucosylated peptide with a fucosyltransferase, which has the desired activity. For example, the methods can form oligosaccharide determinants such as Fucα1,2Galβ1,4(Fucα1,3)GlcNAcβ-OR and Fucα1,2Galβ1,3(Fucα1,4)GlcNAc-OR. Thus, in another preferred embodiment, the method includes the use of at least two fucosyltransferases. The multiple fucosyltransferases are used either simultaneously or sequentially. When the fucosyltransferases are used sequentially, it is generally preferred that the glycoprotein is not purified between the multiple fucosylation steps. When the multiple fucosyltransferases are used simultaneously, the enzymatic activity can be derived from two separate enzymes or, alternatively, from a single enzyme having more than one fucosyltransferase activity.

H. Multiple-enzyme Oligosaccharide Synthesis

As discussed above, in some embodiments, two or more enzymes may be used to form a desired oligosaccharide or oligosaccharide determinant on a glycoprotein or glycolipid. For example, a particular oligosaccharide determinant might require addition of a galactose, a sialic acid, and a fucose in order to exhibit a desired activity. Accordingly, the invention provides methods in which two or more enzymes, e.g., glycosyltransferases, transsialidases, or sulfotransferases, are used to obtain high-yield synthesis of a desired oligosaccharide determinant.

In one preferred embodiment, LNFIII was prepared from lactose using the H. pylori α-1,3/4-fucosyltranferases from strain 1182 described herein, in combination with Neisseria gonococcus β-1,3N-acetylglucosaminyltransferase (lgtA) and Neisseria gonococcus β-1,4-galactosyltransferase (lgtB). Those of skill will recognize that other β-1,3N-acetylglucosaminyltransferase and β-1,4-galactosyltransferase enzymes can be used in this embodiment of the invention.

In some cases, a glycoprotein- or glycolipid linked oligosaccharide will include an acceptor substrate for the particular glycosyltransferase of interest upon in vivo biosynthesis of the glycoprotein or glycolipid. Such glycoproteins or glycolipids can be glycosylated using the H. pylori fucosyltransferase proteins and methods of the invention without prior modification of the glycosylation pattern of the glycoprotein or glycolipid, respectively. In other cases, however, a glycoprotein or glycolipid of interest will lack a suitable acceptor substrate. In such cases, the methods of the invention can be used to alter the glycosylation pattern of the glycoprotein or glycolipid so that the glycoprotein-or glycolipid-linked oligosaccharides then include an acceptor substrate for the glycosyltransferase-catalyzed attachment of a preselected saccharide unit of interest to form a desired oligosaccharide moiety.

Glycoprotein- or glycolipid linked oligosaccharides optionally can be first "trimmed," either in whole or in part, to expose either an acceptor substrate for the glycosyltransferase or a moiety to which one or more appropriate residues can be added to obtain a suitable acceptor substrate. Enzymes such as glycosyltransferases and endoglycosidases are useful for the attaching and trimming reactions. For example, a glycoprotein that displays "high mannose"-type oligosaccharides can be subjected to trimming by a mannosidase to obtain an acceptor substrate that, upon attachment of one or more preselected saccharide units, forms the desired oligosaccharide determinant.

The methods are also useful for synthesizing a desired oligosaccharide moiety on a protein or lipid that is unglycosylated in its native form. A suitable acceptor substrate for the corresponding glycosyltransferase can be attached to such proteins or lipids prior to glycosylation using the methods of the present invention. See, e.g., U.S. Pat. No. 5,272,066 for methods of obtaining polypeptides having suitable acceptors for glycosylation.

Thus, in some embodiments, the invention provides methods for in vitro sialylation of saccharide groups present on a glycoconjugate that first involves modifying the glycoconjugate to create a suitable acceptor. Examples of preferred methods of multi-enzyme synthesis of desired oligosaccharide moieties are as follows.

Fucosylated and Sialylated Oligosaccharide Moieties

Oligosaccharide determinants that confer a desired biological activity upon a glycoprotein often are sialylated in addition to being fucosylated. Accordingly, the invention provides methods in which a glycoprotein-linked oligosaccharide is sialylated and fucosylated in high yields.

The sialylation can be accomplished using either a trans-sialidase or a sialyltransferase, except where a particular moiety requires an α2,6-linked sialic acid, in which a sialyltransferase is used. Suitable examples of each type of enzyme are described above. These methods involve sialylating an acceptor for a sialyltransferase or a trans-sialidase by contacting the acceptor with the appropriate enzyme in the presence of an appropriate donor substrate. For sialyltransferases, CMP-sialic acid is a preferred donor substrate. Trans-sialidases, however, preferably use a donor substrate that includes a leaving group to which the trans-sialidase cannot add sialic acid.

Acceptor substrates of interest include, for example, Galβ-OR. In some embodiments, the acceptor substrates are contacted with a sialyltransferase in the presence of CMP-sialic acid under conditions in which sialic acid is transferred to the non-reducing end of the acceptor substrate to form the compound NeuAcα2,3Galβ-OR or NeuAcα2,6GalβOR. In this formula, R is an amino acid, a saccharide, an oligosaccharide or an aglycon group having at least one carbon atom. R is linked to or is part of a glycoprotein. An α2,8-sialyltransferase can also be used to attach a second or multiple sialic acid residues to the above structures.

To obtain an oligosaccharide moiety that is both sialylated and fucosylated, the sialylated acceptor is contacted with a fucosyltransferase as discussed above. The sialyltransferase and fucosyltransferase reactions are generally conducted sequentially, since most sialyltransferases are not active on a fucosylated acceptor. FT VII, however, acts only on a sialylated acceptor substrate. Therefore, FTVII can be used in a simultaneous reaction with a sialyltransferase.

If the trans-sialidase is used to accomplish the sialylation, the fucosylation and sialylation reactions can be conducted either simultaneously or sequentially, in either order. The protein to be modified is incubated with a reaction mixture that contains a suitable amount of a trans-sialidase, a suitable sialic acid donor substrate, a fucosyltransferase (capable of making an α1,3 or α1,4 linkage), and a suitable fucosyl donor substrate (e.g., GDP-fucose).

Galactosylated, Fucosylated and Sialylated Oligosaccharide Determinants

The invention also provides methods for enzymatically synthesizing oligosaccharide moieties that are galactosylated, fucosylated, and sialylated. Either a sialyltransferase or a trans-sialidase (for α2,3-linked sialic acid only) can be used in these methods.

The trans-sialidase reaction involves incubating the protein to be modified with a reaction mixture that contains a suitable amount of a galactosyltransferase (galβ1,3 or galβ1,4), a suitable galactosyl donor (e.g., UDP-galactose), a trans-sialidase, a suitable sialic acid donor substrate, a fucosyltransferase (capable of making an α1,3 or α1,4 linkage), a suitable fucosyl donor substrate (e.g., GDP-fucose), and a divalent metal ion. These reactions can be carried out either sequentially or simultaneously.

If a sialyltransferase is used, the method involves incubating the protein to be modified with a reaction mixture that contains a suitable amount of a galactosyltransferase (galβ1,3 or galβ1,4), a suitable galactosyl donor (e.g., UDP-galactose), a sialyltransferase (α2,3 or α2,6) and a suitable sialic acid donor substrate (e.g., CMP sialic acid). The reaction is allowed to proceed substantially to completion, and then a fucosyltransferase (capable of making an α1,3 or α1,4 linkage) and a suitable fucosyl donor substrate (e.g., GDP-fucose). If a fucosyltransferase is used that requires a sialylated substrate (e.g., FT VII), the reactions can be conducted simultaneously.

Sialyltransferase Reactions

As discussed above, in some embodiments, the present invention provides a H. pylori fucosyltransferase proteins and methods for fucosylating a glycoprotein following the sialylation of the glycoprotein. In a preferred embodiment, the fusion proteins and methods of the invention synthesize glycoproteins having a substantially uniform sialylation pattern. The sialylated glycoprotein is then fucosylated, thereby producing a population of fucosylated glycoproteins in which the members have a substantially uniform fucosylation pattern.

The glycoprotein can be contacted with a sialyltransferase and a sialic acid donor substrate for a sufficient time and under appropriate reaction conditions to transfer sialic acid from the sialic acid donor substrate to the saccharide groups. Sialyltransferases comprise a family of glycosyltransferases that transfer sialic acid from the donor substrate CMP-sialic acid to acceptor oligosaccharide substrates. In preferred embodiments, the sialyltransferases are recombinant sialyltransferase fusion proteins. Suitable sialyltransferase reactions are described in U.S. Provisional Application No. 60/035,710, filed Jan. 16, 1997 and U.S. nonprovisional application Ser. No. 09/007,741, filed Jan. 15, 1998.

In some embodiments, the saccharide moieties on a glycoprotein having sialylation patterns altered by the H. pylori fucosyltransferase proteins of the present invention have a greater percentage of terminal galactose residues sialylated than the unaltered glycoprotein. Preferably, greater than about 80% of terminal galactose residues present on the glycoprotein-linked oligosaccharides will be sialylated following use of the methods. More preferably, use of the H. pylori fucosyltransferase proteins and methods of the invention will result in greater than about 90% sialylation, and even more preferably greater than about 95% sialylation of terminal galactose residues. Most preferably, essentially 100% of the terminal galactose residues present on the glycoproteins in the composition are sialylated following modification using the methods of the present invention. The fusion proteins and methods of the inventions are typically capable of achieving the desired level of sialylation in about 48 hours or less, and more preferably in about 24 hours or less.

At least 15 different mammalian sialyltransferases have been documented, and the cDNAs of thirteen of these have been cloned to date (for the systematic nomenclature that is used herein, see, Tsuji et al. (1996) *Glycobiology* 6: v-xiv). These cDNAs can be used for making the recombinant sialyltransferase fusion proteins of the invention.

Preferably, for glycosylation of N-linked and/or O-linked carbohydrates of glycoproteins, the sialyltransferase transfer sialic acid to the terminal sequence Galβ1,4-OR or GalNAc-OR, where R is an amino acid, a saccharide, an oligosaccharide or an aglycon group having at least one carbon atom and is linked to or is part of a glycoprotein. Galβ1,4-GlcNAc is the most common penultimate sequence underlying the terminal sialic acid on fully sialylated carbohydrate structures. At least three of the cloned mammalian sialyltransferases meet this acceptor specificity requirement, and each of these have been demonstrated to transfer sialic acid to N-linked and O-linked carbohydrate groups of glycoproteins.

In some embodiments, the invention sialylation methods that have increased commercial practicality through the use of bacterial sialyltransferases, either recombinantly produced or produced in the native bacterial cells. Two bacterial sialyltransferases have been recently reported; an ST6Gal II from *Photobacterium damsela* (Yamamoto et al. (1996) *J. Biochem.* 120: 104-110) and an ST3Gal V from *Neisseria meningitidis* (Gilbert et al. (1996) *J. Biol. Chem.* 271: 28271-28276). The two recently described bacterial enzymes transfer sialic acid to the Galβ1,4GlcNAc sequence on oligosaccharide substrates.

A recently reported viral α2,3-sialyltransferase is also suitable for testing and possible use in the sialylation methods of the invention (Sujino et al. (2000) *Glycobiology* B10: 313-320). This enzyme, v-ST3Gal I, was obtained from Myxoma virus-infected cells and is apparently related to the mammalian ST3Gal IV as indicated by comparison of the respective amino acid sequences. v-ST3Gal I catalyzes the sialylation of Type I (Galβ1,3-GlcNAcβ1-R), Type II (Galβ1,4GlcNAcβ1-R) and III (Gal β1,3GalNAcβ1-R) acceptors. The enzyme can also transfer sialic acid to fucosylated acceptor substrates (e.g., Lewis-x and Lewis-a).

An example of a sialyltransferase that is useful in the claimed methods is ST3Gal III, which is also referred to as α(2,3)sialyltransferase (EC 2.4.99.6). This enzyme catalyzes the transfer of sialic acid to the Gal of a Galβ1,3GlcNAc, Galβ1,3GalNAc or Galβ1,4GlcNAc glycoside (see, e.g., Wen et al. (1992) *J. Biol. Chem.* 267: 21011; Van den Eijnden et al. (1991) *J. Biol. Chem.* 256: 3159). The sialic acid is linked to a Gal with the formation of an α-linkage between the two saccharides. Bonding (linkage) between the saccharides is between the 2-position of NeuAc and the 3-position of Gal. This particular enzyme can be isolated from rat liver (Weinstein et al. (1982) *J. Biol. Chem.* 257: 13845); the human cDNA (Sasaki et al. (1993) *J. Biol. Chem.* 268: 22782-22787; Kitagawa & Paulson (1994) *J. Biol. Chem.* 269: 1394-1401) and genomic (Kitagawa et al. (1996) *J. Biol. Chem.* 271: 931-938) DNA sequences are known, facilitating production of this enzyme by recombinant expression. In a preferred embodiment, the claimed sialylation methods use a rat ST3Gal III.

Other sialyltransferases, including those listed above, are also useful in an economic and efficient large scale process for sialylation of commercially important glycoproteins. As described above, a simple test to find out the utility of these other enzymes, is to react various amounts of each enzyme (1-100 mU/mg protein) with a readily available glycoprotein protein such as asialo-$\alpha_1$-AGP (at 1-10 mg/ml) to compare the ability of the sialyltransferase of interest to sialylate glycoproteins. The results can be compared to, for example, either or both of an ST6Gal I or an ST3Gal III (e.g., a bovine or human enzyme), depending upon the particular sialic acid linkage that is desired. Alternatively, other glycoproteins or glycoproteins, or N- or O-linked oligosaccharides enzymatically released from the peptide backbone can be used in place of asialo-$\alpha_1$ AGP for this evaluation, or one can use saccharides that are produced by other methods or purified from natural products such as milk. Preferably, however, the sialyltransferases are assayed using an oligosaccharide that is linked to a glycoprotein. Sialyltransferases showing an ability to, for example, sialylate N-linked or O-linked oligosaccharides of glycoproteins more efficiently than ST6Gal I are useful in a practical large scale process for glycoprotein sialylation.

The invention also provides methods of altering the sialylation pattern of a glycoprotein prior to fucosylation by adding sialic acid in an a2,6Gal linkage as well as the α2,3Gal linkage, both of which are found on N-linked oligosaccharides of human plasma glycoproteins. In this embodiment, ST3Gal III and ST6Gal I sialyltransferases are both present in the reaction and provide proteins having a reproducible ratio of the two linkages formed in the resialylation reaction. Thus, a mixture of the two enzymes may be of value if both linkages are desired in the final product.

An acceptor substrate for the sialyltransferase is present on the glycoprotein to be modified by the sialylation methods described herein. Suitable acceptors include, for example, galactosylated acceptors such as Galβ1,4GlcNAc, Galβ1,4GalNAc, Galβ1,3GalNAc, Galβ1,3GlcNAc, Galβ1,3Ara, Galβ1,6GlcNAc, Galβ1,4Glc (lactose), GalNAc-O-Ser, GalNAc-O-Thr, and other acceptors known to those of skill in the art (see, e.g., Paulson et al. (1978) *J. Biol. Chem.* 253: 5617-5624). Typically, the acceptors are included in oligosaccharide chains that are attached to asparagine, serine, or threonine residues present in a protein.

EXAMPLES

The following examples are offered to illustrate, but not to limit the claimed invention.

Example 1

Cloning of *Helicobacter pylori* Fucosyltransferases

Putative fucosyltransferase genes from the following strains of *Helicobacter pylori* were PCR amplified, cloned into vectors for expression in *E. coli:* strain 915 FutA, strain 1111 FutA, strain 19C2 FutB, strain 1182 FutB, strain 19C2 FutA, strain 26695 FutA, and strain 1218 FutB. Nucleic acid and amino acid sequences are provided in FIGS. 1-7. An amino acid sequence alignment is provided in FIG. 12; a nucleic acid sequence alignment is provided in FIG. 13.

The putative fucosyltransferase proteins were screened for α1,3/4-fucosyltransferase activity using LNnT and GDP-fucose substrates. The oligostructures of LNnT and one product, LNFPIII are shown in FIG. 14.

One hundred milliliter cultures of *E. coli* transformed with *H. pylori* fucosyltransferase were grown to OD600 of 0.8 and induced with IPTG, and harvested. Cell lysates were made using a french press. The fucosyltransferase enzymes were tested for enzymatic activity and acceptor specificity using the substrate LNnT. The reactions contained 3 mM GDP-fucose, 3 mM LNnT, 50 mM Tris pH 7.5, 20 mM $MnCl_2$, and 15% bacterial lysate. Reactions were incubated at 37° C. for twenty-four hours.

Reaction products were separated using the following TLC-buffer system: 7 IPA:2 $H_2O$:1 Acetic acid. The samples were methylated, hydrolyzed, reduced with sodium borodeuteride, acetylated and analyzed by GC/MS along with samples of LNnT and LNF3. Results are shown in FIG. 15. A Glc vs. Glc-NAc value close to 1 favors fucosylation of Glc-NAc. A Glc vs. Glc-NAc value close to 0 favors fucosylation of Glc. Fucosyltransferases from the following *H. pylori* strains transferred fucose to Glc-NAc: strain 915 FutA, strain 1111 FutA, strain 19C2 FutB, and strain 1182 FutB. The FutA gene product from *H. pylori* strain 19C2A transferred fucose to the reducing glucose of the LNnT acceptor, as did the FutB gene product from *H. pylori* strain 1218 FutB. A novel FutA gene product from *H. pylori* strain 26695 also catalyzed the transfer of fucose to glucose.

Example 2

Production of Oligosaccharides using *Helicobacter pylori* Fucosyltransferases

One liter cultures of *E. coli* expressing *H. pylori* fucosyltransferases were grown, induce and harvested. The lysates were used to synthesize LNFIII from LNnT. Two different ion exchange resins were tested for purification of LNFIII. Reaction mixtures were centrifuged at 5,000 RPM for thirty minutes. Samples were then processed by ultrafiltration using hollow fiber ultrafiltration membranes with a molecular weight cut off of 10 kD. Ion exchange chromatography was done using either MR3 $NH_4HCO_3$ column 1 ml resin per 1 ml synthesis (70%) or Dowexl/Dowex50 column 2 ml resin per 1 ml synthesis (82%). Samples were then run on a P2 Size Exclusion column and then lyophilized. Results are shown in FIG. 16. Yields using the Dowex resin approached 50%, while yields from the MR3 $NH_4HCO_3$ column approached 70%.

LNFIII was prepared from lactose using lysates from *E. coli* cells expressing *H. pylori* α-1,3/4-fucosyltranferases from strain 1182 described herein, in combination with *Neisseria gonococcus* β-1,3N-acetylglucosaminyltransferase (lgtA) and *Neisseria gonococcus* β-1,4-galactosyltransferase (lgtB) on a multigram scale. Those of skill will recognize that other β-1,3N-acetylglucosaminyltransferase and β-1,4-galactosyltransferase enzymes can be used in this embodiment of the invention.

Example 3

Production of Glycoproteins using *Helicobacter pylori* Fucosyltransferases

The ability of fucosyltransferase from *H. pylori* strain 1182B to add fucose to acceptor molecules on glycoprotein was tested using asialyltransferrin as a substrate. The 1182B fucosyltransferase was produced in *E. coli* cells as described above. The reactions were carried out in a buffer containing 50 mM Tris pH. 7.5, 20 mM $MnCl_2$, 200 µg asialyltransferrin, and 5 mM GDP-fucose. Reactions were started by adding 15% v/v of the bacterial lysate. The reaction was incubated overnight at 37° C. The samples were analyzed using GC/MS. Results are shown in FIG. 17.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

---

What is claimed is:

1. A method for producing a fucosylated glycoprotein, the method comprising: contacting a recombinant fucosyltransferase protein with a mixture comprising a donor substrate comprising a GDP-fucose residue, and an acceptor substrate on a glycoprotein, wherein the acceptor substrate comprises an N-acetylglucosamine residue, under conditions where the fucosyltransferase catalyzes the transfer of the fucose residue from the donor substrate to the acceptor substrate on the glycoprotein, thereby producing a fucosylated glycoprotein, wherein the recombinant fucosyltransferase protein comprises a polypeptide having greater than 95% identity to the amino acid sequence of SEQ ID NO: 4.

2. The method of claim 1, wherein the polypeptide comprises the amino acid sequence of SEQ ID NO: 4.

3. The method of claim 1, wherein the polypeptide further comprises an amino acid tag.

4. The method of claim 1, wherein the method further comprises a step of purifying the fucosylated glycoprotein.

5. The method of claim 1, wherein an acceptor substrate on the glycoprotein comprises Galβ,3/4GlcNAc-OR, NeuAcα2, 3Galβ,3/4GlcNAc-OR, wherein R is an amino acid, a saccharide, an oligosaccharide, or a radical group having at least one carbon atom.

6. A method of making a fucosylated oligosaccharide, the method comprising: contacting the recombinant fucosyltransferase with a mixture comprising a donor substrate comprising a GDP-fucose residue, and an acceptor substrate comprising a sugar or oligosaccharide, wherein the acceptor substrate comprises an N-acetylglucosamine residue, under conditions where the fusion protein catalyzes the transfer of a fucose residue from the donor substrate to the acceptor substrate, thereby producing a fucosylated oligosaccharide, wherein the recombinant fucosyltransferase protein comprises a polypeptide having greater than 95% identity to the amino acid sequence of SEQ ID NO:4.

7. The method of claim 6, wherein the method further comprises a step of purifying the fucosylated oligosaccharide.

8. The method of claim 6, wherein the fucosyltransferase comprises an amino acid tag.

9. The method of claim 6, wherein the acceptor substrate is Lacto-N-neo-Tetraose (LNnT).

10. The method of claim 9, wherein the fucosylated oligosaccharide is Lacto-N-Fucopentaose III (LNFP III).

11. The method of claim 6, wherein the mixture further comprises lactose, a β-1,3-N-acetylglucosaminyltransferase, and a β1,4-galactosyltransferase.

12. The method of claim 11, wherein the β-1,3-N-acetyiglucosaminyltransferase is a bacterial enzyme.

13. The method of claim 12, wherein the β-1,3-N-acetyiglucosaminyltransferase is from *Neisseria gonococcus*.

14. The method of claim 11, wherein the β-1,4-galactosyltransferase is a bacterial enzyme.

15. The method of claim 14, wherein the β-1,4-galactosyltransferase is from *Neisseria gonococcus*.

16. The method of claim 11, wherein the fucosylated oligosaccharide is Lacto-N-Fucopentaose III (LNFP III).

17. A method for producing a fucosylated glycolipid, the method comprising: contacting the recombinant fucosyltransferase protein of with a mixture comprising a donor substrate comprising a GDP-fucose residue, and an acceptor substrate on a glycolipid, wherein the acceptor substrate comprises an N-acetylglucosamine residue, under conditions where the fucosyltransferase catalyzes the transfer of the fucose residue from the donor substrate to the acceptor substrate on the glycolipid, thereby producing a fucosylated glycolipid, wherein the recombinant fucosyltransferase protein comprises a polypeptide having greater than 95% identity to the amino acid sequence of SEQ ID NO:4.

* * * * *